US008889394B2

(12) United States Patent
Chalasani

(10) Patent No.: US 8,889,394 B2
(45) Date of Patent: Nov. 18, 2014

(54) MULTIPLE DOMAIN PROTEINS

(75) Inventor: Sreekanth H. Chalasani, LA Jolla, CA (US)

(73) Assignee: Empire Technology Development LLC, Wilmington, DE (US)

( * ) Notice: Subject to any disclaimer, the term of this patent is extended or adjusted under 35 U.S.C. 154(b) by 389 days.

(21) Appl. No.: 12/554,949

(22) Filed: Sep. 7, 2009

(65) Prior Publication Data

US 2011/0059502 A1 Mar. 10, 2011

(51) Int. Cl.
*C12N 9/22* (2006.01)
*C12N 9/00* (2006.01)
*C07K 14/47* (2006.01)

(52) U.S. Cl.
CPC ......... *C07K 14/4702* (2013.01); *C07K 2319/09* (2013.01); *C07K 2319/00* (2013.01); *C07K 2319/81* (2013.01); *C07K 2319/71* (2013.01); *C12N 9/00* (2013.01); *C07K 2319/80* (2013.01); *C07K 2319/40* (2013.01); *C07K 2319/20* (2013.01); *C07K 2319/02* (2013.01); *C07K 2319/50* (2013.01); *C07K 2319/60* (2013.01)
USPC .......................... 435/199; 435/252.3; 435/325

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,935,357 A | 6/1990 | Szybalski | |
| 4,965,188 A | 10/1990 | Mullis et al. | |
| 5,096,815 A | 3/1992 | Ladner et al. | |
| 5,232,841 A | 8/1993 | Hashimoto et al. | |
| 5,268,273 A | 12/1993 | Buckholz | |
| 5,286,632 A | 2/1994 | Jones | |
| 5,389,529 A | 2/1995 | Panayotatos et al. | |
| 5,470,719 A | 11/1995 | Meng et al. | |
| 5,595,899 A | 1/1997 | Sato et al. | |
| 5,648,247 A | 7/1997 | Picataggio et al. | |
| 5,656,493 A | 8/1997 | Mullis et al. | |
| 5,708,154 A | 1/1998 | Smith et al. | |
| 5,712,114 A | 1/1998 | Mankovich et al. | |
| 5,716,780 A | 2/1998 | Edwards et al. | |
| 5,766,891 A | 6/1998 | Shuman | |
| 5,846,818 A | 12/1998 | Robinson et al. | |
| 5,888,732 A | 3/1999 | Hartley et al. | |
| 5,932,419 A | 8/1999 | Bauer et al. | |
| 5,932,474 A | 8/1999 | Tsien et al. | |
| 6,008,378 A | 12/1999 | Tsien et al. | |
| 6,054,271 A | 4/2000 | Tsien et al. | |
| 6,143,557 A | 11/2000 | Hartley et al. | |
| 6,171,861 B1 | 1/2001 | Hartley et al. | |
| 6,270,969 B1 | 8/2001 | Hartley et al. | |
| 6,277,608 B1 | 8/2001 | Hartley et al. | |
| 6,288,302 B1 | 9/2001 | Yu et al. | |
| 6,451,569 B1 | 9/2002 | Tsien et al. | |
| 6,627,424 B1 * | 9/2003 | Wang .............................. 435/194 |
| 6,720,140 B1 | 4/2004 | Hartley et al. | |
| 7,393,632 B2 | 7/2008 | Cheo et al. | |
| 7,670,823 B1 | 3/2010 | Hartley et al. | |
| 8,241,860 B2 * | 8/2012 | Ghosh et al. .................. 435/7.21 |
| 2002/0007051 A1 | 1/2002 | Cheo et al. | |
| 2003/0083373 A1 | 5/2003 | Tsien et al. | |
| 2004/0248299 A1 | 12/2004 | Jayasena et al. | |
| 2005/0112590 A1 | 5/2005 | Boom et al. | |
| 2005/0287592 A1 | 12/2005 | Kless | |
| 2006/0084136 A1 | 4/2006 | Kudlicki et al. | |
| 2006/0128020 A1 | 6/2006 | Calos | |
| 2007/0111228 A1 | 5/2007 | Jayasena et al. | |

FOREIGN PATENT DOCUMENTS

| | | |
|---|---|---|
| WO | WO-96/19497 | 6/1996 |
| WO | WO-98/56943 | 4/1999 |
| WO | WO-99/21013 | 4/1999 |

OTHER PUBLICATIONS

Tilsner et al. (The Plant Journal, vol. 57, pp. 758-770, Feburary 2009.*
Shehi et al. (Biochemistry, vol. 42, pp. 8362-8368, 2003.*
Shehi et al. (FEBS Lett., 497(2-3):131-6), 2001.*
Ngo et al., In The Protein Folding Problem and Tertiary Structure Prediction, 1994, Merz et al. (ed.), Birkhauser, Boston, MA, pp. 433 and 492-495.*
Cheong et al., "Engineering RNA sequence specificity of *Pumilio* repeats", PNAS, vol. 103, No. 37, pp. 13635-13639, Sep. 2006.*
Porteus et al., Nature Biotechnology 23(8):967-973, 2005.*
Zinc Finger Nuclease (ZFN)—CompoZr Zinc Finger Nuclease Technology. Functional Genomics & RNAi [online]. Sigma-Aldrich Co., 2011 [printed on Feb. 10, 2011]. Retrieved from the Internet: <URL: http://www.sigmaaldrich.com/life-science/functional-genomics-and-mai/zinc-finger-nuclease-technology.html>, 1 page.
Auweter, S.D. et al., "Sequence-specific binding of single-stranded RNA: is there a code for recognition?" Nucleic Acids Research, 2006, vol. 34, No. 17, pp. 4943-4959.
Dreyfuss, G. et al., "Messenger-RNA-Binding Proteins and the Messages They Carry," Nature Reviews, Mol. Cell. Biology, Mar. 2002, vol. 3, pp. 195-205.
Protein Databases [online]. European Molecular Biology Laboratory—European Bioinformatics Institute, 2011 [printed on Feb. 10, 2011]. Retrieved from the Internet: <URL: http://www.ebi.ac.uk/Databases/protein.html>, 1 page.
Search for dnmt1 in Protein Sequences [online]. European Molecular Biology Laboratory—European Bioinformatics Institute, 2011 [printed on Feb. 10, 2011]. Retrieved from the Internet: <URL: http://www.ebi.ac.uk/ebisearch/search.ebi?db=proteinSequences&t=dnmt1>, 2 pages.
Overview of the Expressway Cell-Free Expression System, Proteins, Expression, Isolation & Analysis [online]. Invitrogen by Life Technologies, 2011 [printed on Feb. 10, 2011]. Retrieved from the Internet: <URL: http://www.invitrogen.com/site/us/en/home/Products-and-Services/Applications/Protein-Expression-and-Analysis/Protein-Expression/Cell-Free-Expression.html>, 1 page.

(Continued)

*Primary Examiner* — Richard Hutson
(74) *Attorney, Agent, or Firm* — Foley & Lardner LLP

(57) ABSTRACT

Described herein are methods and compositions for generating and using fusion proteins.

4 Claims, 1 Drawing Sheet

(56) References Cited

OTHER PUBLICATIONS

P04390 (T2E5_ECOLX), Search for P04390 in Protein Knowledgebase (UniProtKB) [online], UniProt Consortium, 2002-2011 [printed on Feb. 10, 2011]. Retrieved from the Internet: <URL: http://www.uniprot.org/uniprot/P04390>, 6 pages.

Akbergenov, R. Zh. et al., "ARC-1, a sequence element complementary to an internal 18S rRNA segment, enhances translation efficiency in plants when present in the leader or intercistronic region of mRNAs", Nucleic Acids Research, 2004, vol. 32, No. 1, pp. 239-247.

Capone, J.P., et al., "Amber, ochre and opal suppressor tRNA genes derived from a human serine tRNA gene" The EMBO Journal, 1985, vol. 4, No. 1, pp. 213-221.

Eggertsson, G., and Soll, D., "Transfer Ribounucleic Acid-Mediated Suppression of Termination Codons in *Escherichia coli*" Microbiological Reviews, Sep. 1988, vol. 52, No. 3, pp. 354-374.

Engelberg-Kulka, H., and Schoulaker-Schwarz, R., "Suppression of termination condons," In *Escherichia coli* and *Salmonella*: Cellular and Molecular Biology, Chapter 60, pp. 909-921, Neidhardt, et al. eds., ASM Press, Washington, (1996).

Enzyme Nomenclature, from NC-IUBMB (http://web.archive.org/web/20110430172655/http://www.chem.qmul.ac.uk/iubmb/enzyme/) retrieved on Apr. 19, 2013, 7 pages.

Fukumori, T., et al., "Exo-Taq-based detection of DNA-binding protein for homogeneous and microarray format," J. Biochem, vol. 138, No. 4, pp. 473-478 (2005).

Gallie, D, R., "The 5032-leader of tobacco mosaic virus promotes translation through enhanced recruitment of eIF4F," Nucleic Acids Research, vol. 30, No. 15, pp. 3401-3411, Oxford University Press (2002).

Gallie, D, R., et al., "The 5'-leader sequence of tobacco mosaic virus RNA enhances the expression of foreign gene transcripts in vitro and in vivo," Nucleic Acids Research, vol. 15, No. 8, pp. 3257-3273, IRL Press Limited, England (1987).

Hill, C., "Automating nucleic acid amplification tests," IVDT Technology magazine, accessed at http://web.archive.org/web/20081201084254/http://www.devicelink.com/ivdt/archive/00/11/007.html, Nov./Dec. 2000, pp. 8.

Lakhiaeva, E., and Zwieb, C., "Characterization of protein-RNA complexes using QIAGEN Ni-NTA Magnetic Agarose Beads," QIAGEN News, 2007, pp. 1-3 accessed at http://www.qiagen.com/literature/qiagennews/weeklyarticle/07_11/e15/default.aspx.

Landy, A., "Mechanistic and structural complexity in the site-specific recombination pathways of Int and FLP," Current Opinion in Genetics & Development, vol. 3, No. 5, pp. 699-707 (1993).

Mignone, F., et al., "Untranslated regions of mRNAs," Genome Biology, vol. 3, No. 3, pp. 1-10, BioMed Central Ltd (2002).

Mignone, F., et al., "UTRdb and UTRsite: a collection of sequences and regulatory motifs of the untranslated regions of eukaryotic mRNAs," Nucleic Acids Research, vol. 33, pp. D141-D146, Oxford University Press (2005).

Myers, E. W., and Miller, W., "Optimal alignments in linear space," CABIOS, 1989, vol. 4, No. 1, pp. 11-17, IRL Press Limited, England (1988).

Needleman, S.B., and Wunsch. C.D., "A General Method Applicable to the Search for Similarities in the Amino Acid Sequences of Two Proteins," J. Mol. Biol, vol. 48, pp. 443-453 (1970).

Nelson, N. C., et al., "Simultaneous detection of multiple nucleic acid targets in a homogeneous format," Biochemistry, vol. 35, No. 25, pp. 8429-8438, American Chemical Society (1996).

Papanikolaou, S., and Aggelis, G., "Lipid production by *Yarrowia lipolytica* growing on industrial glycerol in a single-stage continuous culture," Bioresource Technology, vol. 82, Issue 1, pp. 43-49 (2002).

Paulous, S., et al., "Comparison of the capacity of different viral internal ribosome entry segments to direct translation initiation in poly(A)-dependent reticulocyte lysates," Nucleic Acids Research, vol. 31, No. 2, pp. 722-733, Oxford University Press (2003).

PCR Cloning with TOPO® Technology: Minimize planning, guarantee success, from Invitrogen.com (http://liveweb.archive.org/http://tools.invitrogen.com/downloads/F-13512_Topo_Flyer.pdf) retrieved on Apr. 19, 2013, 2 pages.

Sauer, B., "Site-specific recombination: developments and applications," Current Opinion in Biotechnology, vol. 5, Issue 5, pp. 521-527 (1994).

Sekiguchi, J., and Shuman, S., et al., "Requirements for noncovalent binding of vaccinia topoisomerase I to duplex DNA," Nucleic Acids Research, vol. 22, No. 24, pp. 5360-5365, Oxford University Press (1994).

Shaloiko, L, A., et al., "Effective non-viral leader for cap-independent translation in a eukaryotic cell-free system," Biotechnology and Bioengineering, vol. 88, No. 6, pp. 730-739 (2004).

Shuman, S., "Site-specific Interaction of Vaccinia Virus Topoisomerase I with Duplex DNA: minimal DNA substrate for strand cleavage in vitro," The Journal of Biological Chemistry, vol. 266, No. 17, pp. 11372-11379, The American Society for Biochemistry and Molecular Biology, In. (1991).

Strauss, W.M., "Current Protocols in Molecular Biology," Ausubel, F.M., et al., eds., John Wiley & Sons, New York, pp. 6.3.1-6.3.6 (1989).

Tag-On-Demand122 Gateway® Vectors, from Invritogen.com (http://liveweb.archive.org/http://tools.invitrogen.com/content/sfs/manuals/tagondemand_vectors_man.pdf) retrieved on Apr. 19, 2013, 44 pages.

Tjalsma, H., et al., "Signal Peptide-Dependent Protein Transport in *Bacillus subtilis*: a Genome-Based Survey of the Secretome," Microbiology and Molecular Biology Reviews, vol. 64, No. 3, pp. 515-547, American Society for Microbiology (2000).

Vincent, M., et al., "Helicase-dependent isothermal DNA amplification," EMBO reports, vol. 5, No. 8, pp. 795-800, European Molecular Biology Organization (2004).

MacRae I. J., and Doudna J. A., "Ribonuclease revisited: structural insights into ribonuclease III family enzymes", Current Opinion in Structural Biology, 2007, vol. 17, pp. 1-8.

* cited by examiner

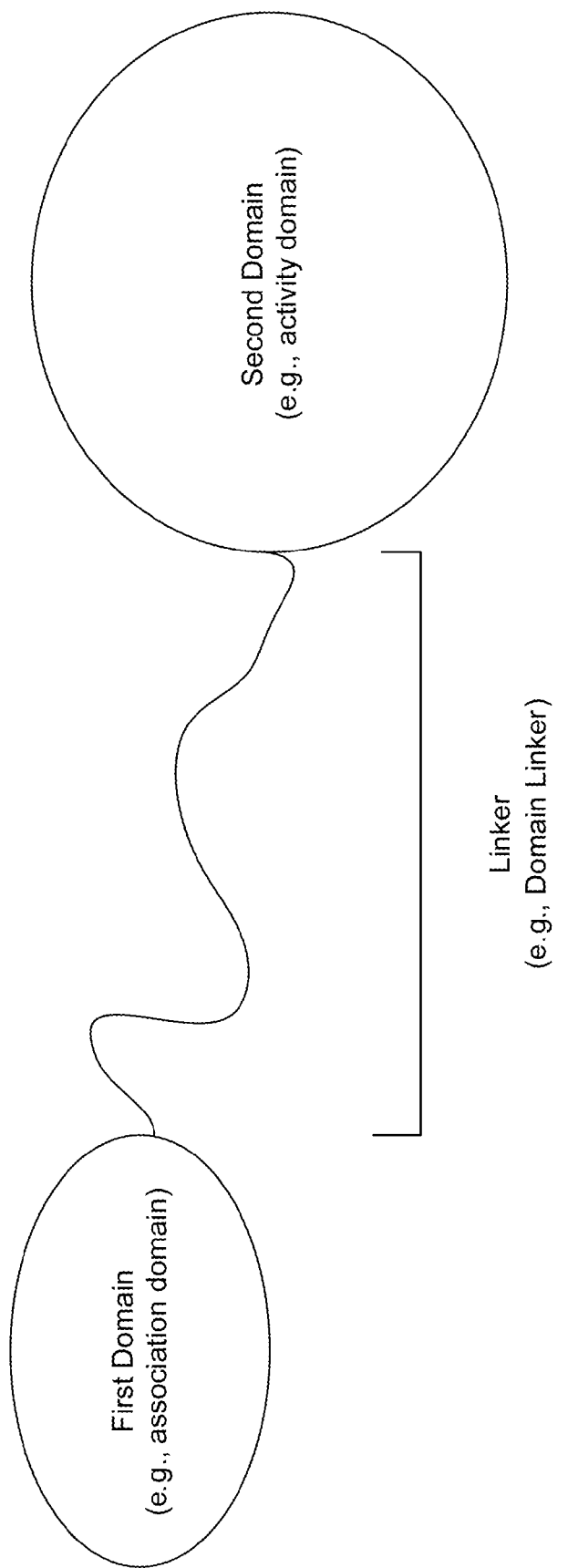

MULTIPLE DOMAIN PROTEINS

SEQUENCE LISTING

The instant application contains a Sequence Listing which has been submitted via EFS-Web and is hereby incorporated by reference in its entirety. Said ASCII copy, created on Dec. 17, 2009, is named IVA-1001-UT.txt, and is 102,557 bytes in size.

FIELD

The technology relates in part to fusion proteins and protein engineering.

BACKGROUND

Naturally occurring proteins sometimes have one or more domains, which can serve different functions. Domains can target the protein to a certain nucleic acid sequence or region of the cell. Domains also can posses an activity that is performed when the protein is targeted to a particular cellular region or nucleic acid sequence.

A fusion protein often is a protein engineered to combine a desired activity domain with a targeting or localization domain. Novel fusion proteins can be designed to carry out specific functions based on the various combinations of targeting and activity domains that can be combined. Fusion proteins are useful in laboratory, clinical and other settings.

SUMMARY

Provided herein are methods and compositions for generating novel fusion proteins that are useful for laboratory, clinical, industrial, or other applications. Fusion proteins described herein often comprise two domains, such as an association domain and an activity domain, for example. An association domain can provide increased specificity to the activity domain, and allow target localization of the activity to specific sequences or structures often found in nucleic acids. Fusion proteins generated using methods and compositions described herein can be used in vitro, in vivo, or ex vivo.

Thus, featured in some embodiments are fusion proteins that comprise two heterologous domains connected by a linker, where a first domain can be configured to associate with a nucleic acid and a second domain may have an activity selected from the group consisting of methylase activity, demethylase activity, transcription activation activity, transcription repression activity, transcription release factor activity, histone modification activity, RNA cleavage activity and nucleic acid association activity. In certain embodiments, the first domain may comprise one, two, four, five or more nucleic acid association regions.

In some embodiments, the first domain does not include a zinc finger association region. In certain embodiments, the first domain sometimes comprises a nucleic acid association region from a transcription factor, and the transcription factor can be a Bcl I controller protein, in some embodiments. In certain embodiments, the first domain can comprise a nucleic acid association region selected from the group consisting of helix-turn-helix region, leucine zipper region, winged helix region, winged helix-turn-helix region, helix-loop-helix region, immunoglobulin fold and B3 domain. In some embodiments, the first domain does not comprise a zinc-finger region.

In some embodiments, the first domain can comprise a nucleic acid association region that binds RNA. In certain embodiments, the nucleic acid association region that binds RNA can comprise a pumilio encoding nucleotide sequence. In some embodiments, the nucleic acid association region that binds RNA can comprise a TFIII zinc finger encoding nucleotide sequence. In certain embodiments, the nucleic acid association region that binds RNA can comprise a RRM, staufen, KH type I or KH type II encoding nucleotide sequence.

In certain embodiments, the activity of a second domain in a fusion protein can be about 25% to about 90% more specific than the activity of a second domain not in a fusion protein. In some embodiments, a second domain can comprise an endonuclease activity. In certain embodiments, a second domain can comprise a type II endonuclease activity, a type III endonuclease activity, a type IV endonuclease activity or a homing endonuclease activity. In some embodiments, a second domain does not substantially have a type IIs endonuclease activity (e.g., Fok I, Alw I).

In certain embodiments, a second domain can comprise a methylase activity. In some embodiments, a second domain can comprise a methylase activity of an enzyme having classification 2.1.1.1.37. The enzyme nomenclature and classification system used from time to time herein is from the Nomenclature Committee of the International Union of Biochemistry and Molecular Biology (IUBMB), in consultation with the IUPAC-IUBMB Joint Commission on Biochemical Nomenclature. The enzyme classification information used from time to time herein is from the nomenclature version update of Jul. 3, 2009. Enzyme classification designations may be subject to change. One of skill will be able to use the information listed here to identify a molecule referred to by a classification number changed in the future. The enzyme nomenclature designations can be located at World Wide Web uniform resource locator (URL) chem.qmul.ac.uk/iubmb/enzyme/.

In certain embodiments, a second domain can comprise a methylase activity that transfers a methyl group to DNA, RNA, protein, small molecule, cytosine or adenine. In certain embodiments, a second domain can comprise a demethylase activity.

In some embodiments, a second domain can comprise a transcription activator activity. In certain embodiments, the transcription activator activity can be a VP16, VP64 or p65 domain of NF kappa B transcription activator activity. In some embodiments, a second domain can comprise a transcription repressor activity. In certain embodiments, the transcription repressor activity can be a Kruppel associated box, ERF repressor domain, MadSID or TATA box binding protein activity.

In some embodiments, a second domain can comprise a transcription release factor. In certain embodiments, the transcription release factor can be a eukaryotic release factor 1 (ERF1) or eukaryotic release factor 3 (ERF3) activity.

In some embodiments, a second domain can comprise a histone modification activity. In certain embodiments, the histone modification activity can be a histone deacetylase, histone acetyltransferase or histone methyltransferase activity.

In some embodiments, a second domain can comprise a nucleic acid association activity. In certain embodiments, the nucleic acid association activity can be a RNA association activity. In some embodiments, the RNA association activity can be a RNA recognition motif (RRM) or ribonucleoprotein domain (RNP) activity.

In certain embodiments, the first domain comprises a DNA association activity. In some embodiments, a second domain can comprise a RNA cleavage activity. In certain embodiments the RNA cleavage activity is a Dicer activity.

In certain embodiments, the linker can be 70% to 100% of one or more amino acids selected from the group consisting of glycine, alanine, threonine and serine. In some embodiments, the linker can be about 5 amino acids to about 50 amino acids in length. In certain embodiments, the linker can be selected from the group consisting of GSGGGGSAAGASAS (SEQ ID NO: 1), STSGGSGGTGGS (SEQ ID NO: 2) and GGTG-GTGGSGGTG (SEQ ID NO: 3).

Also featured in some embodiments are methods for manufacturing a fusion protein, which comprises; (a) selecting a polynucleotide encoding an activity domain, (b) selecting a polynucleotide encoding an association domain that improves the specificity of the activity domain, (c) linking the selected activity and association domains via a polynucleotide encoded amino acid linker, and (d) operably linking the linked association and activity domains to a transcription promoter. In some embodiments, the nucleic acid encoding the operably linked activity and association domains can be replicated. In certain embodiments, the operably linked nucleic acids can be replicated by one or more methods selected from, amplification of the linked nucleic acids, insertion of the linked nucleic acids into a DNA expression construction, insertion of the linked nucleic acids into a DNA construct suitable for replication of nucleic acids. In some embodiments, the method can further comprise expressing the nucleic acids encoding a fusion proteins described herein. In certain embodiments, the method can further comprise testing the activity of the expressed fusion protein.

Also featured in some embodiments are methods useful for modifying a target nucleic acid, which method can comprise contacting the target nucleic acid with a fusion protein described herein, under modification conditions, where the target nucleic acid is modified by a fusion protein.

Also provided in some embodiments are isolated nucleic acids that can comprise a nucleotide sequence that encodes a fusion protein as described herein. Also provided in certain embodiments are cells that comprise a nucleic acid encoding a fusion protein and/or a fusion protein generated as described herein. Also provided in some embodiments are cell-free systems that can comprise a nucleic acid encoding a fusion protein and/or a fusion protein generated as described herein.

The foregoing summary illustrates certain embodiments and does not limit the disclosed technology. In addition to illustrative aspects, embodiments and features described above, further aspects, embodiments, and features will become apparent by reference to the drawings and the following detailed description and examples.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 1 shows a schematic representation of a fusion protein made in accordance with embodiments described herein.

DETAILED DESCRIPTION

In the following detailed description, reference is made to the accompanying drawings, which form a part hereof. In the drawings, similar symbols typically identify similar components, unless context dictates otherwise. Illustrative embodiments described in the detailed description, drawings, and claims do not limit the technology. Other embodiments may be utilized, and other changes may be made, without departing from the spirit or scope of the subject matter presented herein. It will be readily understood that aspects of the present disclosure, as generally described herein, and illustrated in the drawings, can be arranged, substituted, combined, separated, and designed in a wide variety of different configurations, all of which are explicitly contemplated herein.

Recent advances in molecular biology and protein engineering have enabled rational design of hybrid proteins comprising (i) a DNA and/or RNA binding polypeptide that can recognize and bind a target nucleic acid sequence, and (ii) a second polypeptide having a certain activity. These hybrid proteins, also referred to as fusion proteins, may deliver a desired activity to a target location by the combination of appropriate localization (e.g., nucleic acid association domain) and activity domains. Non-limiting examples of applications for which fusion proteins described herein can be used include targeted chromosomal cleavage, targeted mutagenesis, targeted chromatin modification, targeted gene activation, targeted gene silencing, genome editing, genome surgery, combinations thereof and the like.

In certain embodiments, fusion proteins generated as described herein can initiate a process that cellular DNA repair machinery can complete (e.g., in a cell-free system or in a host cell). A non-limiting example of such embodiments is a fusion protein that can be used for genome surgery by stimulating targeted homologous recombination. Using the appropriate association and activity domains, a fusion protein can provide initial targeting and double stranded break in the target nucleic acid sequences. The cell's DNA repair machinery can complete recombination repair in the presence of heterologous sequences the artisan may use to cause insertions or deletions from a host's genome.

FIG. 1 illustrates an embodiment of a fusion protein as described herein. In FIG. 1, a first domain (e.g., nucleic acid association domain), a second domain (e.g., activity domain) and a linker (e.g., amino acid linker used to functionally combine the first and second domain), are illustrated. A fusion protein embodiment presented in FIG. 1 is shown in a peptide or protein form. It is understood that one or more nucleic acids can be used to encode fusion proteins described herein. It is also understood that an activity may be provided by one or more domains and a fusion protein can have two or more domains. In some embodiments an activity may be provided by one or more domains (e.g., 1, 2, 3, 4, 5 or more domains; a domain may have binding activity and/or other activity), and a fusion protein can have two or more domains (e.g., 2, 3, 4, 5, 6, 7, 8, 9, 10 or more domains). Examples and descriptions of each domain type and the linker shown in FIG. 1 are provided herein.

The term "domain" as used herein refers to a polypeptide that includes an amino acid sequence of an entire polypeptide or a functional portion of a polypeptide. Certain functional subsequences are known, and if they are not known, can be determined by truncating a known sequence and determining whether the truncated sequence yields a functional polypeptide.

A domain may contain an amino acid sequence identical to a sequence or subsequence of a naturally occurring endogenous polypeptide in a cell, in some embodiments. In certain embodiments, an amino acid sequence in a domain may include one or more modifications relative to a corresponding sequence in a naturally occurring endogenous polypeptide (e.g., a deletion, an insertion, a modification). For example, a domain may include a functional amino acid sequence that is 80% or more identical to a an amino acid sequence or subsequence of a naturally occurring endogenous polypeptide (e.g., 81, 82, 83, 84, 85, 86, 87, 88, 89, 90, 91, 92, 93, 94, 95, 96, 97, 98, 99%, or greater than 99%, identical). The function of the modified amino acid sequence may be less than, equal to or greater than the function of the unmodified amino acid sequence. In some embodiments, a functional amino acid sequence in a domain includes 1, 2, 3, 4, 5, 6, 7, 8, 9, or 10 amino acid insertions, deletions and/or modifications relative to a naturally occurring endogenous amino acid sequence or subsequence of a polypeptide. The term "functional amino acid sequence" as used herein refers to an amino acid sequence of a domain that imparts a function to the domain.

A functional amino acid sequence in a domain also may have a different post-translational modification profile as compared to a corresponding naturally occurring amino acid sequence. A domain may include one of more portions other than the entire protein or functional region of a protein, including but not limited to a capture region and detection region.

In some embodiments described herein domains can be heterologous. The term "heterologous" as used herein refers to domains from different proteins. For example, the first domain in a fusion protein is from one protein and a second domain is from another protein, in some embodiments. Domains in a fusion protein can be from proteins in organisms of the same species or different taxonomic species, genus, order, class, phylum or kingdom, in certain embodiments (e.g., one domain is from a human and another domain is from a bacterium).

A first domain sometimes is a nucleic acid association domain. A second domain sometimes is an activity domain. Activity and recognition domains can be obtained from a organism and can include a types of targeting or activity domains (explained in further detail below). Domains can be functionally combined using a linker. Fusion proteins can be generated using recombinant DNA techniques and reagents known in the art, where suitable targeting domains and activity domains can be combined. Association and activity domains can be identified and selected using resources available to the artisan, such as Genbank; NCBI; Swissprot; EMBL; REBASE; databases accessed at World Wide Web URLs ebi.ac.uk/Databases/protein.html, dbd.mrc- and lmb-.cam.ac.uk/DBD/index.cgi?Home; and ifti.org/ootfd/ and the like. Fusion proteins can be made part of or encoded by a nucleic acid reagent. The nucleic acid reagent comprising a nucleotide sequence encoding a fusion protein, as described herein, can be expressed in a cell free system or in a host organism.

Types of Domains
Nucleic Acid Association Domains

A fusion protein can have a first domain comprising a nucleic acid association activity, in some embodiments. The association activity often can recognize or bind one or more types of nucleic acid. The terms "nucleic acid association domain", "nucleic acid recognition domain" or "nucleic acid binding domain" and grammatical equivalents thereof, as used herein refers to the ability of a peptide or protein to recognize nucleic acid structures or nucleotide sequences (e.g., target nucleic acids) and associate or bind at, or near, a target nucleic acid region. The terms "nucleic acid association domain", "nucleic acid recognition domain" or "nucleic acid binding domain" can be used interchangeably in embodiments described herein. The term "association" refers to an interaction in some embodiments, and an interaction sometimes is a covalent association, and often is a non-covalent association, between the association domain of a fusion protein and a target nucleic acid. An association sometimes is a binding association, and binding sometimes is non-reversible, and often is reversible. Binding often is effected by one or more intermolecular forces, including, but not limited to, ionic interactions, hydrogen bonds, hydrophobic interactions and Van der Waals forces. A fusion protein sometimes binds to one site in a target molecule or target molecules, and in certain embodiments, binds to two or more sites in a target molecule or target molecules. Binding sometimes is selective or specific (e.g., binds to one or a few binding sites with higher frequency than other sites), and at times is non-selective (e.g., binds to multiple binding sites).

Nucleic acid association activity can be DNA association and/or RNA association, in certain embodiments. In some embodiments, a first domain can bind DNA, and in certain embodiments, a first domain can bind RNA. In some embodiments, a first domain can bind RNA and/or DNA, depending on what target is available (e.g., a nucleic acid association domain sometimes can recognize a nucleic acid sequence or structure that forms in DNA or RNA). In certain embodiments, a first domain sometimes is 1, 2, 4, 5 or more nucleic acid association or recognition domains. Non-limiting examples of protein classes that can have nucleic acid association or binding domains include: transcription factors (e.g., transcriptional activators and transcriptional repressors), histones, RNA binding proteins and the like.

DNA Binding Activity

A nucleic acid association domain sometimes can have a DNA binding activity. In some embodiments, DNA recognition and/or association activity can target regions of DNA secondary structure (hairpins, zDNA, triplex DNA, chromatin, and the like, for example). In some embodiments, DNA recognition activity can target DNA sequences (TATA box, transcription factor binding sites, CAAT box, and the like, for example). In certain embodiments, the first domain is not or does not include a zinc finger domain. In some embodiments, the first domain does not include a zinc finger that associates with DNA (Type 1 or type 2 zinc fingers for example).

In certain embodiments, the first domain includes a nucleic acid association region from a transcription factor. Transcription factors generally are sequence-specific binding proteins that contain one or more DNA binding domains. Transcription factors sometimes can activate transcription of a gene, and sometimes can repress transcription of a gene. Transcription factors that activate transcription also can be referred to as transcriptional activators, while transcription factors that repress transcription also can be referred to as transcriptional repressors.

Transcription factors are often classified based on the sequence similarity and tertiary structure of their DNA binding domains. In some embodiments, the first domain includes a nucleic acid association region selected from the group consisting of helix-turn-helix region, leucine zipper region, winged helix region, winged helix-turn-helix region, helix-loop-helix region, immunoglobulin fold and B3 domain. Non-limiting examples of transcription factors that contain some of the association region motifs described above include TFIIA, TFIIB, TFIIE, TFIIH, TATA binding protein (also referred to as TFIID), HOX, HSF, HIF, SRY, MYC, Sp1, NF1, CCAAT, GATA, HNF, PIT-1, MyoD, CREB, G-Box, AP-1, STAT, C/EBP-like factors, RAV, ABI, AP2, pocket domains, copper first domains, RUNT, Cold shock factors (csd), SOX, p53, TUBBY, IRF, Homeo domain, Kruppel, TFIIIA, homologs thereof, and the like. Other non-limiting examples of transcription factors include GCN4 and related homeodomain transcription factors.

In certain embodiments, the transcription factor can be a Bcl I controller protein (e.g., C.Bcl I). C.Bcl I is involved in regulation of the Bcl I restriction-modification system (R-M system). A C.Bcl I polypeptide can bind to a 12 base pair (bp) inverted repeat sequence. A C.Bcl I polypeptide can act to repress the expression of DNA methyltransferases of the Bcl I R-M system of its host organism, thereby protecting the organism from invading nucleic acid pathogens (DNA and RNA bacteriophage, for example). A C.Bcl I polypeptide falls into the group of DNA binding proteins that contain helix-turn-helix DNA binding domains.

Transcription factor nucleic acid association domains suitable for use in embodiments described herein also can be selected based on binding to desired nucleic acid sequences or by secondary feature characteristics (e.g., frequency of appearance in genome, association with particular types of DNA, association with particular genes, or genes involved with a particular cellular function, combinations thereof and the like). Additional transcription factors and the nucleic acid sequence motifs they bind can be identified using resources available to the artisan including but not limited to Genbank and other nucleic acid and/or protein sequence databases.

Examples of databases and accession numbers for transcription factors include, without limitation:

for C.BclI, PDB (2B5A-D) and nucleotide (85544221-85544224);

for GCN4 PDB (P0369, P03068, Q70D88, Q70D91, Q70D96, Q70D99, Q70DA0, Q96UT3) and nucleotide (121066);

for helix-turn-helix, World Wide Web URL ebi.ac.uk/ebi-search/search.ebi?db=proteinSequences &t=helix-turn-helix;

for leucine zipper, World Wide Web URL ebi.ac.uk/ebi-search/search.ebi?db=proteinSequences &t=leucine+zippers;

for winged helix World Wide Web URL ebi.ac.uk/ebisearch/search.ebi?db=proteinSequences &t=winged+helix;

for winged helix-turn-helix, World Wide Web URL ebi.ac.uk/ebisearch/search.ebi?db=proteinSequences&t=winged+helix+turn+helix; and for helix-loop-helix, World Wide Web URL ebi.ac.uk/ebi-search/search.ebi? db=proteinSequences&t=helix+loop+helix, and ebi.ac.uk/interpro/IEntry?ac=IPR003340 (e.g., the latter protein is useful for plant fusion proteins).

Examples of a transcription factor polynucleotide and polypeptides include, without limitation, the following:

C.BclI 4 polypeptide chains 2B5A-D

```
Chain A
MINEIEIKRKFGRTLKKIRTQKGVSQEELADLAGLHRTYISEVERGDRNI
SLINIHKICAALDIPASTFFRKMEEEN (SEQ ID NO: 4)

Chain B
MINEIEIKRKFGRTLKKIRTQKGVSQEELADLAGLHRTYISEVERGDRNI
SLINIHKICAALDIPASTFFRKMEEEN (SEQ ID NO: 4)

Chain C
MINEIEIKRKFGRTLKKIRTQKGVSQEELADLAGLHRTYISEVERGDRNI
SLINIHKICAALDIPASTFFRKMEEEN (SEQ ID NO: 4)

Chain D
MINEIEIKRKFGRTLKKIRTQKGVSQEELADLAGLHRTYISEVERGDRNI
SLINIHKICAALDIPASTFFRKMEEEN (SEQ ID NO: 4)
```

Yeast GCN4

```
polypeptide:
MSEYQPSLFALNPMGFSPLDGSKSTNENVSASTSTAKPMVGQLIFDKFIKTEEDPIIKQD

TPSNLDFDFALPQTATAPDAKTVLPIPELDDAVVESFFSSSTDSTPMFEYENLEDNSKEW

TSLFDNDIPVTTDDVSLADKAIESTEEVSLVPSNLEVSTTSFLPTPVLEDAKLTQTRKVK

KPNSVVKKSHHVGKDDESRLDHLGVVAYNRKQRSIPLSPIVPESSDPAALKRARNTEAAR

RSRARKLQRMKQLEDKVEELLSKNYHLENEVARLKKLVGER (SEQ ID NO: 5)

polynucleotide:
atcttcggggatataaagtgcatgagcatacatcttgaaaaaaaagatgaaaaatttcc gactttaaatacggaagataaatactccaaccttttttccaattccgaaattttagtct tcttttaaagaagtttcggctcgctgtcttacctttttaaaatcttctacttcttgacagta cttatcttcttatataatagatatacaaaacaaaacaaaacaaaaactcacaacacaggt tactctccccctaaattcaaattttttttgcccatcagtttcactagcgaattatacaa ctcaccagccacacagctcactcatctacttcgcaatcaaaacaaaatattttattttag ttcagtttattaagttattatcagtatcgtattaaaaaattaaagatcattgaaaaatgg cttgctaaaccgattatattttgtttttaaagtagattattattagaaaattattaagag aattatgtgttaaatttattgaaagagaaaatttatttttcccttattaattaaagtccctt tacttttttttgaaaactgtcagtttttttgaagagttatttgttttgttaccaattgctat catgtacccgtagaattttattcaagatgtttccgtaacggttacctttctgtcaaatta tccaggtttactcgccaataaaaatttccctatactatcattaattaaatcattattatt actaaagttttgtttaccaatttgtctgctcaagaaaataaattaaatacaaataaaatg tccgaatatcagccaagtttatttgctttaaatccaatgggtttctcaccattggatggt tctaaatcaaccaacgaaaatgtatctgcttccacttctactgccaaaccaatggttggc
```

```
caattgattttgataaattcatcaagactgaagaggatccaattatcaaacaggatacc ccttcgaaccttgattttgattttgctcttccacaaacggcaactgcacctgatgccaag accgttttgccaattccggagctagatgacgctgtagtggaatctttcttttcgtcaagc actgattcaactccaatgtttgagtatgaaaacctagaagacaactctaaagaatggaca tccttgtttgacaatgacattccagttaccactgacgatgtttcattggctgataaggca attgaatccactgaagaagtttctctggtaccatccaatctggaagtctcgacaacttca ttcttacccactcctgttctagaagatgctaaactgactcaaacaagaaaggttaagaaa ccaaattcagtcgttaagaagtcacatcatgttggaaaggatgacgaatcgagactggat catctaggtgttgttgcttacaaccgcaaacagcgttcgattccactttctccaattgtg cccgaatccagtgatcctgctgctctaaaacgtgctagaaacactgaagccgccaggcgt tctcgtgcgagaaagttgcaaagaatgaaacaacttgaagacaaggttgaagaattgctt tcgaaaaattatcacttggaaaatgaggttgccagattaaagaaattagttggcgaacgc tgatttcatttacctttatttatattttttatttcattctcgtgtataacgaaataga tacattcacttagataagaatttaatctttttatgccaattttcttaagtagaatttta caccacgcatttataatctgccgtatgttctggtatttactggttaggaatagataaaaa aaacactcacgatgggggtcgaac (SEQ ID NO: 6)
```

DNA binding activity can be assayed using standard techniques and protocols known to the artisan and available in laboratory manuals such as Maniatis, T., E. F. Fritsch and J. Sambrook (1982) *Molecular Cloning: a Laboratory Manual*; Cold Spring Harbor Laboratory, Cold Spring Harbor, N.Y. One such protocol is a "gel-shift" or "electrophorectic mobility shift" assay. Gel shift assays are a common affinity electrophoresis technique commonly used to investigate protein-DNA or protein-RNA interactions. Migration of DNA alone, or migration of DNA associated with protein are examined using polyacrylamide or agarose gel electrophoresis. Protein associated with a nucleic acid typically shows a greater retardation in the gel matrix than DNA alone.

To detect or visualize the migration of the DNA, a nucleic acid fragment monitored in gel shift assays can be labeled with a label (e.g., radioactive, fluorescent or biotin label). Standard ethidium bromide staining sometimes can be used but often is less sensitive than the aforementioned methods of visualization, and sometimes can lack the sensitivity to detect the nucleic acid if small amounts are used in the assays. In some embodiments, streptavidin conjugated to an enzyme such as horseradish peroxidase can be used to detect the DNA fragment, when using a biotin label. Gel shift assays sometimes are performed in vitro concurrently with DNase footprinting, primer extension, and/or promoter-probe experiments when studying transcription initiation, DNA replication, DNA repair or RNA processing and maturation.

In certain embodiments, DNA binding activity is assessed by an exonuclease protection assay. For example, (i) a fusion protein can be incubated with probe DNA, (ii) the probe is digested with Exo III and (iii) the mixture of (ii) is extended with Taq polymerase using one or more detectable nucleotides (e.g., fluorescent dye-labeled dUTP as a substrate; Fukumori et al., J. Biochem. 138, 473-478 (2005)). A fusion protein having DNA binding activity protects the probe from digestion by the exonuclease. Exonuclease protection assays can be conducted using nucleic acid arrays (e.g., stem and loop ds-DNA array formats).

DNA binding activity also can be assessed, in certain embodiments, by using microarrays to identify DNA fragments that bind the fusion protein. In some embodiments, a fusion protein is linked to a solid support and nucleic acid targets are contacted with the support for assessing DNA binding activity (e.g., a fusion protein may be tagged with a binding pair and the other binding pair member can be linked to the solid support (e.g., polyhistidine tag/divalent metal binding pair)).

RNA Binding Activity

A nucleic acid association domain sometimes can have a RNA binding activity. In certain embodiments, the nucleic acid recognized by the nucleic acid association domain is RNA or includes RNA or a structural equivalent thereof. In some embodiments RNA recognition activity can target regions of RNA secondary structure (hairpins, RNA duplexes, other RNA secondary structure and the like, for example). In some embodiments, RNA recognition activity can target RNA nucleotide sequences. The artisan can select suitable RNA structure or sequence motif targets as described above using available nucleotide and/or sequence databases (e.g., Auweter et al, "Sequence-specific binding of single-stranded RNA: is there a code for recognition", Nucleic Acids Research, 34(17):4943-4959, October 2006 and others). Non-limiting examples of proteins or peptides that contain RNA binding domains include Puf family of proteins (e.g., pumilio), RRM (e.g., RNA recognition motif) proteins, staufen family of proteins, KH type I and type II family of proteins, hnRNP family of proteins and the like, and others. In some embodiments, the first domain does not include a zinc finger that associates with RNA (a type 3 zinc finger for example).

In certain embodiments, the nucleic acid association region includes a pumilio nucleotide sequence. Pumilio is a member of the Puf family of proteins, which regulate expression of mRNA by binding the 3' UTRs of their mRNA targets. Pumilio has been found to repress translation of certain mRNA's in *Drosophila*. Homologs of the Puf proteins and in particular Pumilio have been identified in other organisms. Puf proteins contain a sequence specific RNA binding domain comprising eight sequence repeats and N and C terminal flanking regions, collectively known as the Pumilio homology domain. Pumilio RNA binding domains bind to specific sequence motifs or portions thereof of the consensus UGUANAUA (where N is a nucleotide, for example). A "pumilio nucleotide sequence" as used herein refers to a nucleotide sequence identical to, or 80% or more identical to, a naturally occurring nucleotide sequence that encodes a pumilio protein, or a subsequence thereof, that binds to RNA. A pumilio nucleotide sequence may include nucleotide modifications that encode amino acid modifications in the helix alpha 2 of the pumilio protein.

In some embodiments the RNA recognizing nucleic acid association region includes a RRM, Staufen, KH type I or KH type II activity. RNA recognition motifs (e.g., RRM), also referred to as RNA-binding domains are among the most abundant protein domains found in eukaryotic organisms. RRMs can be found in a variety of RNA binding proteins, including various ribonucleoproteins (RNP's), hnRNP proteins, proteins implicated in regulation of alternative splicing, and protein components of snRNPs. Proteins containing RRM's sometimes are involved in RNA splicing, and/or RNA maturation. RRM's can bind double stranded RNA (dsRNA) or single stranded RNA (ssRNA). The motif also appears in some single stranded DNA binding proteins.

Certain common elements of RRM structure include two conserved ribonucleoprotein (RNP) motifs that lie in the center of the RRM beta-sheet, two external beta-strands, loops, the C- and N-termini, and in some examples, a second RRM domain. The aforementioned elements can contribute to high RNA-binding affinity and specific recognition by RRM's. The many RRM's identified can independently associate with a wide variety of RNA secondary structures and nucleotide sequences, therefore these RNA association domains can be used to develop a wide variety of novel fusion proteins using the embodiments described herein. A "RRM encoding nucleotide sequence" as used herein refers to a nucleotide sequence identical to a naturally occurring nucleotide sequence that encodes a RRM containing protein, 80% or more identical to the foregoing, or a subsequence thereof, that binds to RNA. A RRM encoding nucleotide sequence may include nucleotide modifications that encode amino acid modifications in the RNA binding domain of a RRM containing protein.

Staufen is a protein thought to be involved in anterior-posterior axis formation in *Drosophila*. It is particularly notable because it contains five copies of a double stranded RNA binding domain (dsRBD). Double stranded binding domains are among the most common RNA binding motifs and typically are found in single or multiple copies in many eukaryotic and prokaryotic proteins involved in RNA processing, maturation and localization. Staufen is thought to play a role in localization of certain mRNA's in *Drosophila* eggs. The role staufen plays in localization of specific mRNA's indicates that the RNA binding domain of staufen and related or homologous proteins has a certain degree of sequence and/or structure specificity by which it selects the correct mRNA's for localization. The sequence and/or structure specificity of staufen and homologous binding domains can be used to increase the specificity of a functionally linked activity domains in a fusion protein generated using embodiments described herein. A "staufen encoding nucleotide sequence" as used herein refers to a nucleotide sequence identical to a naturally occurring nucleotide sequence, or 80% or more identical to the foregoing, that encodes a staufen RNA binding domain containing protein, or a subsequence thereof that binds to RNA. A staufen encoding nucleotide sequence may include nucleotide modifications that encode amino acid modifications in the RNA binding domain of a staufen domain containing protein.

K homology (KH) domains were first identified in human heterogeneous nuclear ribonucleoproteins (hnRNP's). KH domains can be around 70 amino acids and often are present in a wide variety of quite diverse nucleic acid-binding proteins. KH domains also have been shown to bind RNA. Like many other RNA-binding motifs, KH motifs are found in one or multiple copies. KH domains can be separated in two groups. The first group or type-1 can contain a beta-alpha-alpha-beta-beta-alpha structure, whereas in the type-2 the two last beta-sheets are located in the N-terminal part of the domain (alpha-beta-beta-alpha-alpha-beta). Non-limiting examples of proteins known to contain KH domain include: bacterial polyribonucleotide nucleotidyltransferases (EC: 2.7.7.8); vertebrate fragile X mental retardation protein 1 (FMR1); eukaryotic heterogeneous nuclear ribonucleoprotein K (hnRNP K), one of at least 20 major proteins that are part of hnRNP particles in mammalian cells; mammalian poly(rC) binding proteins; Artemia saline glycine-rich protein GRP33; yeast PAB1-binding protein 2 (PBP2); vertebrate vigilin; and human high-density lipoprotein binding protein (HDL-binding protein). The sequence and or structure specificity of these RNA binding domains can be used to generate fusion proteins using embodiments described herein. A "KH domain encoding nucleotide sequence" as used herein refers to a nucleotide sequence identical to a naturally occurring nucleotide sequence, or 80% or more identical to the foregoing, that encodes a KH domain containing protein, or a subsequence thereof that binds to RNA. A KH domain encoding nucleotide sequence may include nucleotide modifications that encode amino acid modifications in the RNA binding domain of a KH domain containing protein.

In some embodiments, the first domain can include a DNA binding zinc finger and/or an RNA binding zinc finger. In certain embodiments, the first domain can include one or more types of zinc fingers in a suitable combination. Zinc finger polypeptides and polynucleotides are known in the art (e.g., World Wide Web URL sigmaaldrich.com/life-science/functional-genomics-and-rnai/zinc-finger-nuclease-technology.html). In some embodiments the first domain can include a TFIII zinc finger encoding nucleotide sequence. Transcription factor TFIIIA is a RNA polymerase III transcription factor that binds to the internal control region of the 5S RNA gene as the first step in the assembly of a transcription complex. TFIIIA contains an alpha helix that contains a number of zinc-finger motifs (e.g., 9 zinc-finger motifs in *Xenopus* and *Saccharomyces*) that recognize RNA nucleotide sequences. TFIIIA RNA binding motifs from different organisms may exhibit different RNA nucleotide sequence recognition specificity. Therefore additional RNA sequence specificity can be harnessed by the use of TFIIIA RNA binding motifs from different organisms. In some embodiments, the zinc-finger encoding nucleotide sequence, fragments, subsequences and rearrangements of the zinc-finger motifs can be used to generate fusion proteins using methods and compositions described herein. The zinc-finger encoding nucleotide sequence may include nucleotide modifications that encode amino acid modifications in the RNA binding domain of the zinc-finger containing alpha helix of TFIIIA.

Non-limiting examples of RNA binding regions that could be utilized, include (accession numbers listed): Pumilio (CAA44474 and nucleotide X62589.1); TFIIIA (PDB1UN6); RRM (PDB1URN); KH type I (PDB 1EC6);

Type II (PDB 2ASB); Staufen (PDB 1EKZ). Non-limiting examples of RNA binding regions that could be utilized also include those shown in the table hereafter (e.g., Dreyfuss et al., Nature Reviews, Mol. Cell. Biol. 3: 195-205 (2002)).

TABLE

Characteristics of representative hnRNP and mRNP proteins

| Polypeptide | Domain Structure |
| --- | --- |
| A1 | 2XRBD, RGG |
| A2/B1 | 2XRBD, RGG |
| C1/C2 | 1XRBD |
| D (AUF1) | 2XRBD, RGG |
| E1/E2* | 3XKH |
| F | 3XRBD |
| H/H' (DSEF-1) | 3XRBD |
| I (PTB) | 4XRBD |
| K | 3XKH, RGG |
| L | 4XRBD |
| Q | 3XRBD, RGG |
| U | RGG |
| PABPI | 4XRBD |
| HuR | 3XRBD |
| Yra1 | 1XRBD |
| Npl3/Nop3 | 2XRBD, RGG |
| Hrp1/Nab4 | 2XRBD, RGG |
| Squid/hrp40 | 2XRBD, RGG |
| ASF/SF2 (SRp30a) | 2XRBD, RS domain |
| SC35 (SRp30b) | 1XRBD, RS domain |
| SRp20 | 1XRBD, RS domain |
| 9G8 | 1XRBD, RS domain |
| magoh | N/H |
| Y14 | 1XRBD |
| Aly/REF | 1XRBD |
| RNPS1 | 1XRBD, RS domain |
| DEK | N/H |
| Upf3 | 1XRBD |
| SRm160 | RS domain |

*alpha CP1,2 or PCBP1,2 (Although alpha CP1/PCBP1 and alpha CP2/PCBP2 have been identified as hnRNP E1/E2 proteins, it has not been verified that these proteins are identical to hnRNP E proteins in the human hnRNP complexes.
N/H: no significant homology to other known motif Non-limiting examples of a RNA binding region polynucleotide and polypeptides are provided hereafter:
Pumilio

```
polypeptide:
MKFLGGNDDRNGRGGVGVGTDAIVGSRGGVSQDAADAAGAAAAAAVGYVF

QQRPSPGGVGVGVGGVGGGVPGVGAVGSTLHEAAAAEYAAHFAQKQQQTR

WACGDDGHGIDNPDKWKYNPPMNPANAAPGGPPGNGSNGGPGAIGTIGMG

SGLGGGGGGAGGGNNGGSGTNGGLHHQSMAAAAANMAAMQQAAALAKHN

HMISQAAAAVAAQQQHQHPHQQHPQQQQQQQQAQNQGHPHHLMGGGNGLG

NGNGLGIQHPGQQQQQQQQQQQQQHPGQYNANLLNHAAALGHMSSYAQSG

GSMYDHHGGAMHPGMNGGMPKQQPLGPPGAGGPQDYVYMGGQTTVPMGAA

MMPPQNQYMNSAAVAAANRNAAITTSTAKKLWEKSDGKGVSSSTPGGPLH

PLQIPGIGDPSSVWKDHTWSTQGENILVPPPSRAYAHGGASDTSNSGNAG

ILSPRDSTCAKVVEYVFSGSPTNKDSSLSGLEPHLRNLKFDDNDKSRDDK

EKANSPFDTNGLKKDDQVTNSNGVVNGIDDDKGFNRTPGSRQPSPAEESQ

PRPPNLLFPPLPFNHMLMDHGQGMGGGLGGVVGSGNGVGGGSGGGGAGGA

YAAHQQMAAQMSQLQPPMMNGVGGGMPMAAQSPMLNHQAAGPNHMESPGN

LLQQQNFDVQQLFRSQNPGLAAVATNAAAAAAAAAATSAASAAAAVGAP
```

```
-continued
PVPNGSLQQSQQQQQQQQQQQQQQQMHMAAASQQFLAAQQQAQNAAYAAQ

QATSYVINPGQEAAPYMGMIAAAQMPYYGVAPWGMYPGNLIPQQGTQPRR

PLTPSQQGAENQPYQVIPAFLDHTGSLLMGGPRTGTPMRLVSPAPVLVPP

GATRAGPPPPQGPQLYQPQPQTAQQNLYSQQNGSSVGGLALNTSSLTGRR

DSFDRSTSAFSPSTMDYTSSGVAAAANAVNSTVAQAAAAAAAAAARGKW

PGAMSGAASGAYGALGAGNASASPLGAPITPPPSAQSCLLGSRAPGAESR

QRQQQQQQLAAVGLPATAAAAQAAVAAAANNMFGSNSSIFSNPLAIPGTA

AVAAAAAAAAAANSRQVAATAAAAAAVAAAAGGVGGAPQPGRSRLLEDFR

NQRYPNLQLRDLANHIVEFSQDQHGSRFIQQKLERATAAEKQMVFSEILA

AAYSLMTDVFGNYVIQKFFEFGTPEQKNTLGMQVKGHVLQLALQMYGCRV

IQKALESISPEQQQEIVHELDGHVLKCVKDQNGNHVVQKCIECVDPVALQ

FIINAFKGQVYSLSTHPYGCRVIQRILEHCTAEQTTPILDELHEHTEQLI

QDQYGNYVIQHVLEHGKQEDKSILINSVRGKVLVLSQHKFASNVVEKCVT

HATRGERTGLIDEVCTFNDNALHVMMKDQYANYVVQKMIDVSEPTQLKKL

MTKIRKNMAALRKYTYGKHINAKLEKYYMKITNPITVGTGAGGVPAASSA

AAVSSGATSASVTACTSGSSTTTTSTTNSLASPTICSVQENGSAMVVEPS

SPDASESSSSVVSGAVNSSLGPIGPPTNGNVVL (SEQ ID NO: 7)
```

```
polynucleotide:
agtgttgcaaaacgcgcgtgtggttccttgtgctgcaagttaaaatacaa ttcaagttggcaatacgcgcaaaattgtcagctgcgatagctaggaaaag cctccaaaattgagctcctaaccgcgcccacaattgccatatcgacgccc tcgccgcagcagcaacaccaacagcagcagcagcagcagcagcagcaact ctatcagcaacatcaacagcagcagcaacattacggtccaccaccgc cctactttcaacagctacaccagcaacaccaacagcagcagcaacaacag cagcagcagcaacaccagcaacacatgaagttttttgggtggtaacgatga tcgcaatggccgcggaggcgtcggcgttggcacggatgccattgtaggat ctcgaggtggcgtctctcaggatgccgccgatgcagctggtgccgccgca gccgccgccgtcggctatgtcttccagcagcgtccatcgcctggtgggggt tggcgtcggcgtgggcggagtgggtggcggtgtgccaggggtcggagccg taggctcgaccttgcacgaggccgccgccgccgagtacgccgcccacttt gcccagaagcaacagcagacccgatgggcgtgcggcgacgacggccatgg gatcgataacccgacaaatggaagtacaatccgccgatgaatccggcca atgccgctcctggcggtccaccgggaaatggcagtaatggtgggcccggc gccattggaaccattggcatgggcagcggattgggtggtggtggcggcgg cggagctggcggcggaaataatggcggctctggtacgaatggcggtctgc atcatcaatcgatggccgctgcagctgcgaatatggcagccatgcaacag gcggcggcgttggccaagcacaatcacatgatatcacaggcagcagccgc agttgcagcccagcaacaacatcagcatccacaccagcagcatcccagc agcagcagcaacagcagcaggcgcagaaccaggggcatccacatcaccttt atgggcggtggcaatggactgggcaacggcaatggattgggcatacaaca tcccggccagcaacagcagcagcagcagcaacaacagcagcagcaacatc
```

-continued

```
ccggccagtacaacgcgaatctgcttaaccatgcggctgccttgggtcac
atgtcatcttatgcccaatcgggtggcagcatgtacgaccatcatggtgg
agccatgcacccgggaatgaacggcggcatgcccaagcaacagccattgg
gtccacccggagccggaggaccccaggactatgtctacatgggtggccag
accactgtgcccatgggagccgcaatgatgccgccacagaatcaatatat
gaacagcgctgctgttgcagctgccaatcggaatgcagcgattaccacat
ccactgccaagaaattgtgggagaaatccgatggcaagggcgtatcctcg
agcactcccggtggaccgttgcatccctgcagatccccggcatcgggga
tccctcctccgtgtggaaggatcacacctggtccacacagggcgagaata
tattggtgccgccccctcgcgagcctacgcccatggaggcgcctccgat
acttcaaacagcggcaatgcgggcatactgagtccccgcgattcgacttg
cgccaaagtggttgaatatgttttcagtggctcgcccaccaacaaagata
gctcgctttccggattggaaccgcatttgcggaatctaaagtttgacgac
aacgataagtcacgcgacgataaggagaaagcaaactctccgtttgacac
aaacggtttgaagaaagacgatcaggtcacaaactcaaatggtgttgtca
acggcattgacgatgacaagggcttcaatcgcactcctggttcacgtcaa
ccatcacctgcagaggagtcccagccacgtccccccaatctactcttcc
tccactgcccttcaatcacatgctcatggatcatggccaaggcatgggag
gcggcttgggcgagttgttggatctggcaacggagtcggcggtggcagc
ggcggaggcggggcaggcggcgcttatgcggcccaccagcagatggccgc
ccagatgagtcaattgcaaccgccgatgatgaacggcgttggcggcgaa
tgccaatggcagcacagtcaccaatgttgaatcaccaggcagctggaccc
aatcacatggaatctcccggaaatctcttgcagcagcaaaattttgatgt
tcagcaactgtttcgctcgcagaatccgggcctagcagcagttgccacaa
atgcagcggccgcagcagcagccgcagcagctgccacatcggcagcgagt
gctgcggcagcggtgggcgcaccacccgttcccaacggatcgctgcagca
gtcgcagcagcaacagcagcagcagcaacaacagcagcagcaacaacaga
tgcacatggcggccgcgtcgcaacaatttttggccgcccagcagcaggcg
caaaatgcggcctatgccgcccaacaggccacgtcctacgtcatcaatcc
gggccaggaggctgccccgtatatgggcatgattgccgccgcccagatgc
cgtactatggcgtagccatggggcatgtatccgggcaatctgattccg
caacagggaacgcagccgcgccgcccctcacccctcgcagcagggtgc
cgagaatcagccgtatcaggtcatcccggcattcctcgatcacacgggct
ccttgctgatggaggacctcgcacccgggacgccgatgcgtctggttagc
cccgccccgttctggtgccccgggcgctacccgtgccggcccccgcc
cccgcagggcccacagctgtatcagccgcagccgcagacggccaacaga
atctctactcgcagcagaatggatccagtgtcggaggcctcgccttgaac
acgagctcgttgacgggtcgccgcgactccttcgaccgcagcacctccgc
cttcagtccctcgaccatggactacaccagcagcggtgtggcagcggccg
ccaatgcggtgaacagcacagtggcccaggcagcagcagctgccgcagca
```

-continued

```
gccgccgcagcgcgtggcaagtggccgggagcgatgtcgggagcggccag
tggagcctacggagccctgggagcgggcaatgcttcggccagtcccctgg
gcgcaccaatcacgccgccgccatcggcgcaatcctgtctcctgggcagt
cgggcacctggagccgagtcccgccagcggcagcagcaacaacagcagct
ggccgccgttggtctgccggcgactgcagcagctgctcaggcagcggtgg
ccgcggctgccaacaatatgttcggatccaacagctcgatcttctcgaat
cccctggccattccgggtaccgcagctgtggcagctgcagcggcagcagc
agcggccgccaactcgcgtcaggtggctgccacggcagcggcagcagcgg
cggtggcagcagcagccggcggagtgggaggtgccccacagccaggaaga
tctcgccttctcgaagatttccgcaaccagcggtatccaaatcttcagct
acgcgatctcgctaaccacattgtggagttctcacaggatcagcacggct
cgcggtttatccaacagaagttggagcgggccaccgccgccgagaagcaa
atggtgttcagcgagatcctggcggcagcctatagcctgatgaccgatgt
ctttggcaactatgtcatccagaagttctctttgagttcggcactcccgagc
agaagaacacgctgggcatgcaggtcaagggtcatgtgctgcagctggcg
ctgcaaatgtatggctgccgagtgattcagaaggctctggagagcatctc
gccggagcagcagcaggaaatcgtccacgaactggacggacatgtgctga
aatgcgtcaaggatcagaatggcaatcatgtggtgcaaaagtgcattgag
tgcgtggaccccgtggcgctgcagttcatcatcaatgctttcaagggtca
ggtttactcgctaagcacccatccgtatggatgccgggtgatccagagaa
tccttgagcattgcactgccgaacagaccacgcccatttggacgaactg
catgagcacaccgaacagttgattcaggaccaatatggcaactatgttat
tcagcatgtgcttgaacacggcaagcaggaggataagtcgattcttatca
acagcgtgcgcggcaaagttctggtgctatcacagcacaagttcgcctca
aacgttgtggagaaatgtgttacccatgccactcgcggagaacgcactgg
tctcatagacgaggtctgcaccttcaacgacaacgcgttgcacgtgatga
tgaaggatcagtatgccaactatgtggtccaaaaaatgatcgatgtatcg
gagccgacgcagctcaagaagctgatgaccaagatccggaaaaacatggc
cgccttgcgcaagtacacctacggcaagcacatcaatgccaagttggaga
agtactacatgaagataaccaatcccattacggtgggcacaggagctgga
ggagtgccggcagcctcgtcggcggccgcagtcagcagtggtgccacctc
ggcatcggtaaccgcctgcaccagtggcagcagcaccaccacgaccagca
ctaccaacagcctggcctcacccaccattttgttcggtgcaggagaacggc
agcgccatggttgtggagcctcctccccggacgcctccgagtcctcgtc
ctcggtggtgtcaggcgctgtcaacagcagcttgggtcccattggacccc
cgaccaacggcaacgttgtgctgtaaaggaaataacaaattaagccaggc
agtcaaaggaaacttccttctcgaatcgcagtatagttttttagaagctgt
agagcttaacataaacaacaagtacatataaatgtaatcttatttattgg
aaaagcagcgataaatggagctgcactcgaagatttgcaaagaggatagt
aaaacacacatgcgccaatctagagaaacaaatagcaaacaaagaagcac
```

-continued

```
actggcaagcaaaaaagcaaaagagcttaacagctaaaactaaaagaaat ttgtatttttacgaacaaaactaataacgttctcatgaaaaaagatttca aaatatttgtaaaatgcgctcgcataattaatttgtaaaaaaaaggcatg aaccgcaaagatgaaagaaaacaaaaatgcgtagtaaatcgcgatcaaga aaaaaaataatgaatgtaatgtaaaatgtcaatgaaacagatttgtctgc gtacattttcgttgtaactttgtataaattaattattatatagcaagtct atctgtaaatgattaatgtttcgactgtaaattaataagaagacaactga agagccggcgagctgaaaaaaaataaagtaaaaagagcgggctgcatgaa ttagcctacgatttataagttcagacagaggaaccatttctaatatacaa acatatatcgagggataacagcagaagccgcacttagtgtagaatgtag
```

-continued

```
agtaataatgttttttggagccagcagctacaaagacacaatgaaaacaga gacacacgagacacgcccacgcccccctcacgcacactcggttgcatacac ccacacaatgaacgactcttcagcccattcacgttgcttttgcactatgt aaaaattttgtataaaaaaaaaccccaaacaacaaaccatgtaaaccatg taattttcaaatgtttcactgtaaaatgtatacatactttatttttgtaaa ttttttttaagtcgcaagtaactcatacatattctattctaaacctcacg catgtatttataattttatacacattagctggtgaccaccgatcgacgat ctgcatggatgttggtcagctggtggccagctaaaagaacctgttagcca agtaagccaaaaatgataataattggattttaaaacaataaccatcaaaa taaaccaatttttttcaaaa (SEQ ID NO: 8)
```

TFIIIA

>1UN6:F|PDBID|CHAIN|SEQUENCE
GCCGGCCACACCUACGGGGCCUGGUUAGUACCUGGGAAACCUGGGAAUAC
CAGGUGCCGGC (SEQ ID NO: 9)

>1UN6:E|PDBID|CHAIN|SEQUENCE
GCCGGCCACACCUACGGGGCCUGGUUAGUACCUGGGAAACCUGGGAAUAC
CAGGUGCCGGC (SEQ ID NO: 9)

>1UN6:D|PDBID|CHAIN|SEQUENCE
MYVCHFENCGKAFKKHNQLKVHQFSHTQQLPYECPHEGCDKRFSLPSRLK
RHEKVHAGYPCKKDDSCSFVGKTWTLYLKHVAECHQD (SEQ ID NO: 10)

>1UN6:C|PDBID|CHAIN|SEQUENCE
MYVCHFENCGKAFKKHNQLKVHQFSHTQQLPYECPHEGCDKRFSLPSRLK
RHEKVHAGYPCKKDDSCSFVGKTWTLYLKHVAECHQD (SEQ ID NO: 10)

>1UN6:B|PDBID|CHAIN|SEQUENCE
MYVCHFENCGKAFKKHNQLKVHQFSHTQQLPYECPHEGCDKRFSLPSRLK
RHEKVHAGYPCKKDDSCSFVGKTWTLYLKHVAECHQD (SEQ ID NO: 10)

RRM

>1URN:A|PDBID|CHAIN|SEQUENCE
AVPETRPNHTIYINNLNEKIKKDELKKSLHAIFSRFGQILDILVSRSLKM
RGQAFVIFKEVSSATNALRSMQGFPFYDKPMRIQYAKTDSDIIAKMK (SEQ ID NO: 11)

>1URN:B|PDBID|CHAIN|SEQUENCE
AVPETRPNHTIYINNLNEKIKKDELKKSLHAIFSRFGQILDILVSRSLKM
RGQAFVIFKEVSSATNALRSMQGFPFYDKPMRIQYAKTDSDIIAKMK (SEQ ID NO: 11)

>1URN:C|PDBID|CHAIN|SEQUENCE
AVPETRPNHTIYINNLNEKIKKDELKKSLHAIFSRFGQILDILVSRSLKM
RGQAFVIFKEVSSATNALRSMQGFPFYDKPMRIQYAKTDSDIIAKMK (SEQ ID NO: 11)

>1URN:P|PDBID|CHAIN|SEQUENCE
AAUCCAUUGCACUCCGGAUUU (SEQ ID NO: 12)

>1URN:Q|PDBID|CHAIN|SEQUENCE
AAUCCAUUGCACUCCGGAUUU (SEQ ID NO: 12)

>1URN:R|PDBID|CHAIN|SEQUENCE
AAUCCAUUGCACUCCGGAUUU (SEQ ID NO: 12)

KH Type I

>1EC6:B|PDBID|CHAIN|SEQUENCE
MKELVEIAVPENLVGAILGKGGKTLVEYQELTGARIQISKKGEFLPGTRN
RRVTITGSPAATQAAQYLISQRVTYEQGVRASNPQKV (SEQ ID NO: 13)

>1EC6:A|PDBID|CHAIN|SEQUENCE
MKELVEIAVPENLVGAILGKGGKTLVEYQELTGARIQISKKGEFLPGTRN
RRVTITGSPAATQAAQYLISQRVTYEQGVRASNPQKV (SEQ ID NO: 13)

>1EC6:D|PDBID|CHAIN|SEQUENCE
GAGGACCUAGAUCACCCCUC (SEQ ID NO: 14)

>1EC6:C|PDBID|CHAIN|SEQUENCE
GAGGACCUAGAUCACCCCUC (SEQ ID NO: 14)

KH TypeII

>2ASB:A|PDBID|CHAIN|SEQUENCE
GEFSTREGEIVAGVIQRDSRANARGLVVVRIGTETKASEGVIPAAEQVP
GESYEHGNRLRCYVVGVTRGAREPLITLSRTHPNLVRKLFSLEVPEIAD
GSVEIVAVAREAGHRSKIAVRSNVAGLNAKGACIGPMGQRVRNVMSELS
GEKIDIIDYDDDPARFVANALSPAKVVSVSVIDQTARAARVVVPDFQLS
LAIGKEGQNARLAARLTGWRIDIRGDAPPPPPGQPEPGVSRGMAHDRLE
HHHHHH (SEQ ID NO: 15)

>2ASB:B|PDBID|CHAIN|SEQUENCE
GAACUCAAUAG (SEQ ID NO: 16)

Staufen

>1EKZ:A|PDBID|CHAIN|SEQUENCE
MDEGDKKSPISQVHEIGIKRNMTVHPKVLREEGPAHMKNFITACIVGSI
VTEGEGNGKKVSKKRAAEKMLVELQKL (SEQ ID NO: 17)

>1EKZ:B|PDBID|CHAIN|SEQUENCE
GGACAGCUGUCCCUUCGGGACAGCUGUCC (SEQ ID NO: 18)

As noted above for assaying DNA binding activity, RNA binding activity can be assayed and visualized using standard techniques and protocols known to the artisan and available in laboratory manuals such as Maniatis, T., E. F. Fritsch and J. Sambrook (1982) *Molecular Cloning: a Laboratory Manual*; Cold Spring Harbor Laboratory, Cold Spring Harbor, N.Y. Gel shift assays are commonly used to investigate protein-RNA interactions. Modifications to techniques for RNA gel electrophoresis and visualization can be found in laboratory manuals such as the one described above, or other manuals known in the art. A non-limiting example of an assay for assessing RNA-binding activity can be found at World Wide Web URL qiagen.com/literature/qiagennews/weeklyarticle/07_11/e15/default.aspx.

Nucleotide sequences encoding association activities, like those described herein or others known to the artisan suitable for use in embodiments described herein can be identified and selected using various nucleotide and protein sequence database tools available to the artisan. The association domains of nucleic acid binding proteins can be operably or functionally linked to an activity domain to generate novel fusion proteins with a high degree of sequence or structure specificity. Additionally, one of skill can use the binding domains of the proteins to select or identify sequences capable of being bound by the binding domain of a particular nucleic acid binding protein, thus identifying possible sequence motifs recognized by a given nucleic acid binding domain.

Nucleic acid sequence motifs can be selected by binding the protein with the nucleic acid binding domain of interest to a solid support (e.g., column matrix or resin, affinity chip and the like) and a mixture of oligonucleotides (random or non-random sequences, for example) can be passed over or contacted with the immobilized nucleic acid binding protein. Sequences recognized and capable of associating with the immobilized protein containing the nucleic acid binding domain of interest may be retained under appropriate conditions (e.g., binding conditions). The bound oligonucleotides can be collected and analyzed to determine the sequences of the bound oligonucleotides. Comparison of the bound sequences to nucleotide sequence databases can aid the artisan in determining the frequency with which a novel fusion protein comprising one or more of the bound sequences will associate with nucleic acids (e.g., genomic DNA) from a given organism.

Activity Domains

A fusion protein described herein generally includes a second domain that provides a specific activity, such as a nucleic acid modifying activity in certain embodiments (e.g., referred to as an "activity domain"). In certain fusion proteins, an activity domain (also referred to as a "second domain") sometimes is a portion of a fusion protein that carries out a desired modification to a nucleic acid when positioned in a targeted location by the association domain. Activity domains sometimes have enzymatic function (e.g., endonuclease, methylase, ligase, demethylase, glycosylase, exonuclease, recombinase, polymerase and the like). Activity domains sometimes perform an action (e.g., bind to a complementary sequence, silence genes, act as a template for enzymatic function (e.g., as a recombination intermediate for recombination and repair enzymes, knock ins and knock outs), act as a scaffold for assembly of other components and the like).

Activity domains can provide a variety of activities. An activity sometimes is conversion of a substrate to an intermediate or product (e.g., catalytic conversion by an enzyme) and sometimes can refer to the binding of a molecule or ligand. Non-limiting examples of protein classes that can have activities useful for nucleic acid manipulation or modification include: endonucleases, ligases, methylases, demethylases, histone modifiers, polymerases, transcriptional activators, transcriptional repressors, transcription release factors, nucleic acid recombination and repair enzymes, and the like. A non-limiting example of an activity not associated with an enzymatic function is a nucleic acid binding activity (e.g., DNA-DNA, DNA-RNA, RNA-RNA), in certain embodiments.

Effective specificity of an activity domain can be modulated when the activity domain is linked to an association domain in a fusion protein. In some embodiments, the specificity of the fusion protein is increased relative to the unlinked activation domain, as the fusion protein often interacts with a fewer number of sites in a target molecule relative to the unlinked activation domain. An activity domain, when not linked to an association domain, has a certain specificity for a target molecule. An unlinked activity domain may bind to and/or modify a certain number of sites of a target, which sites of the target are referred to in this paragraph as sites A, B and C, by way of example. An association domain often has a particular specificity for the target molecule, and also by way of example, can bind to or near site A in the target molecule, but does not significantly bind to or near site B or site C. When the activity domain is linked to the association domain in a fusion protein, the specificity of the fusion protein is modulated as compared to the free, unlinked activity domain: relative to the free, unlinked association domain, the fusion protein binds to or near site A, and/or modifies site A, with a higher frequency than it binds to or near site B or site C, and/or modifies site B or site C, due to the influence of the association domain. In this example, the fusion protein more specifically interacts with a certain site on the target molecule than the unlinked activation domain. Also in this example, the fusion protein more specifically interacts with one site in the target, and in certain embodiments, a fusion protein may interact more specifically with two or more sites in a target as compared with other sites in the target. Modulating the specificity of an activation domain activity by linkage to an association domain in a fusion protein can be applicable to a number of activation domains described herein.

In some embodiments, an activity of a second domain in a fusion protein is about 25% to about 90% more specific than the activity of a second domain not in a fusion protein. In such embodiments, the activity of a second domain in a fusion protein ($A_{Fusion}$) and the activity of a second domain not in a fusion protein ($A_{Free}$) are measured separately in a suitable manner known for a particular target molecule (e.g., nucleic acid, polypeptide, protein, peptide molecule). Activity can be measured using one or more portions of a target molecule, portions of two or more target molecules, an entire target molecule, or two or more target molecules, in some embodiments. Activity at one or more sites, or one or more predetermined sites, of one or more target molecules, or portions thereof, sometimes is measured. The ratio of $A_{Fusion}$ to $A_{Free}$ multiplied by one-hundred generally equates to the percent a fusion protein activity is more specific (hereafter "percent increased specificity"). For example, where a second domain includes methylase activity, the number of nucleotide positions methylated in a given nucleic acid target are measured under particular reaction conditions for a fusion protein and under the same conditions for a second domain not in a fusion protein. For the latter measurements, a second domain often is not fused to another peptide or protein. If $A_{Fusion}$ is two methylated sites and $A_{Free}$ is ten methylated sites, then the percent increased specificity is 20%, for example. In certain embodiments, the percent increased specificity is about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99%, or greater than 99%. In some embodiments, the target nucleic acid is genomic DNA or endogenous RNA from a cell or cells.

Endonuclease Activity

A second domain can include an endonuclease activity, in some embodiments. Endonucleases are enzymes that cleave a phosphodiester bond within a polynucleotide chain, usually at or near a target or specific nucleic acid sequence. In certain embodiments, an endonuclease can be a restriction endonuclease. In some embodiments, the restriction endonuclease can have double-stranded cleavage activity. In certain embodiments, the restriction endonuclease can have single-stranded cleavage activity (e.g., nicking enzyme). In some embodiments, the restriction endonuclease can be a thermostable restriction endonuclease.

Novel restriction endonuclease fusion proteins can be generated by the combination of an association domain, a linker and an activity domain (e.g., endonuclease activity), as described in embodiments presented herein. Fusion proteins described herein, comprising an endonuclease activity second domain, can be used for many laboratory or clinical applications. Non-limiting examples of uses to which fusion proteins with endonuclease activity can be applied, include novel restriction enzymes, homologous recombination stimulators (e.g., creating double stranded breaks in the presence of heterologous DNA to allow generation of knock in and knock out mutants), genome editing or genome surgery (e.g., in vivo correction of genetic mutations using targeted homologous recombination, ex vivo introduction, removal or modification of sequences associated with a condition or treatment of a condition (disease or cancer, for example) in stem cells or other totipotent or pluripotent cells, followed by reintroduction of the manipulated cells into an organism exhibiting a condition), and the like.

In some embodiments, endonuclease activity can be a type I endonuclease activity, a type II endonuclease activity, a type III endonuclease activity, a type IV endonuclease activity, a homing endonuclease activity, a nicking endonuclease activity and the like. Examples of endonuclease activity domains for use in fusion protein embodiments include, without limitation, the activity domains of endonucleases (e.g., DNase (e.g., DNase I, II); RNase (e.g., RNase E, F, H, P); Cleavase™ enzyme; eukaryotic structure-specific endonucleases; murine FEN-1 endonucleases; type I, II or III restriction endonucleases such as Acc I, Afl III, Alu I, Alw44 I, Apa I, Asn I, Ava I, Ava II, BamH I, Ban II, Bcl I, Bgl I. Bgl II, Bln I, Bsm I, BssH II, BstE II, Cfo I, Cla I, Dde I, Dpn I, Dra I, EcIX I, EcoR I, EcoR I, EcoR II, EcoR V, Hae II, Hae II, Hind III, Hind III, Hpa I, Hpa II, Kpn I, Ksp I, Mlu I, MluN I, Msp I, Nci I, Nco I, Nde I, Nde II, Nhe I, Not I, Nru I, Nsi I, Pst I, Pvu I, Pvu II, Rsa I, Sac I, Sal I, Sau3A I, Sca I, ScrF I, Sfi I, Sma I, Spe I, Sph I, Ssp I, Stu I, Sty I, Swa I, Taq I, Xba I, Xho I); glycosylases (e.g., uracil-DNA glycolsylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1,N6-etheno-adenine DNA glycosylase); ribozymes, endonucleases with RNA activity (e.g., endoribonucleases, such as Dicer), and DNAzymes. In certain embodiments, an endonuclease activity is not a type IIs endonuclease (e.g., not Fok I or Alw I).

Additional endonuclease activities not listed above also may be suitable for use with embodiments described herein, with the proviso they do not have type IIs activity, in certain embodiments. The artisan can identify and select an endonuclease activity suitable for use in embodiments by using the available nucleic acid or amino acid sequence database tools described herein (e.g., World Wide Web URL .neb.com/nebecomm/tech_reference/restriction_enzymes/defaultasp, or rebase.neb.com/cgi-bin/msublist).

Examples of endonuclease sequences described herein can be accessed at World Wide Web URLs ebi.ac.uk/Databases/protein.html and ncbi.nlm.nih.gov/sites/entrez?db=gene. A non-limiting example of an endonuclease sequence for Eco RV can be accessed using accession number P04390 at World Wide Web URL uniprot.org/uniprot/P04390. A non-limiting example of an endonuclease polypeptide and polynucleotide sequence is provided hereafter.

EcoRV polypeptide:
MSLRSDLINALYDENQKYDVCGIISAEGKIYPLGSDTKVLSTIFELFSRP

IINKIAEKHGYIVEEPKQQNHYPDFTLYKPSEPNKKIAIDIKTTYTNKEN

EKIKFTLGGYTSFIRNNTKNIVYPFDQYIAHWIIGYVYTRVATRKSSLKT

YNINELNEIPKPYKGVKVFLQDKWVIAGDLAGSGNTTNIGSIHAHYKDFV

EGKGIFDSEDEFLDYWRNYERTSQLRNDKYNNISEYRNWIYRGRK (SEQ ID NO: 19)

polynucleotide:
atgagtcttcgttctgatttaattaatgcactatatgatgaaaatcaaaa atatgatgtatgcggaataatatctgcagaaggaaaaatatacccattgg gaagtgacacaaaagttctaagcacaatatttgagttattctcaagacca ataataaataaaatagcagaaaaacatgggtatattgtagaagaacctaa acaacaaaatcattatcctgactttactctttacaaaccaagcgaaccaa ataaaaaattgcaatagatataaaaacaacatatacaaacaaagaaaac gaaaaaatcaagttcactcttggtgggtataccagctttatacgaaacaa cacaaaaaatattgtttatccatttgaccaatatatcgcccattggataa tcggatatgtatatacaagagttgccacaagaaaatcatctttaaaaaca tataatataaatgaactcaatgaaatccctaaaccatacaaaggcgtaaa ggttttcttacaagataaatgggttattgctggagatttggcaggatctg gaaacacaacaaatataggtagcattcatgcccactataaagactttgta gaaggaaaaggaatatttgactcagaggatgagttttttagactattggag aaattatgaaagaaccagtcaattaagaaatgacaagtataataatataa gcgaatacagaaactggatataccgaggaagaaaataa (SEQ ID NO: 20)

Assays for endonuclease activity can be performed using techniques and procedures known in the art. For example, an endonuclease activity of a second domain can be assayed by performing DNA or RNA cleavage reactions under appropriate conditions for the novel fusion protein. The term "appropriate condition" as used herein refers to the salt, buffer, temperature and/or nucleotide sequence conditions necessary to allow partial or full functionality of the second or activity domain (e.g., endonuclease activity domain). The results of the assay can be visualized using common methods, such as separation of cleaved nucleic acids by size using electrophorectic techniques, for example.

Methylase Activity

In some embodiments, a second domain can include a methylase activity (e.g., DNA methyltransferase or RNA methyltransferase activity). Methylase activities can be found in prokaryotic and eukaryotic organisms. Methylase activities in prokaryotes (e.g., Dam methylase, Dcm methylase and the like) are most often associated with the restriction-modification system (e.g., R-M system) that protects bacteria from invading pathogens. The genome of the host bacteria often is methylated by its own R-M system, while the nucleic acids of invading pathogens often are not. Unmethylated or incorrectly (as determined by host restriction enzymes) methylated nucleic acids in bacteria often are subject to cleavage by the host restriction enzymes, while the correctly methylated host nucleic acids generally are protected. Methylase activity in eukaryotes (e.g., CpG methylases such as Dnmt1) generally transfers a methyl group to the C5 position of cytosine residues. Patterns of CpG methylation are heritable, tissue specific and often correlate with gene expression. Consequently, CpG methylation may play a role in differentiation and gene expression.

Novel fusion proteins comprising a methylase activity domain can be generated by the combination of an association domain, a linker and an activity domain (e.g., methylase activity), as described in embodiments presented herein. Fusion proteins described herein, comprising a methylase activity second domain, can be used for many laboratory or clinical applications. Non-limiting examples of uses to which fusion proteins with methylase activity can be applied, include gene silencing (turning off gene expression by methylating sequences involved in expression, for example), gene activation (turning on gene expression by methylating sequences involved in repression of a target gene or turning off gene expression of the repressor and the like, for example), targeted methylation of sequences to protect certain sequences from cleavage by restriction enzymes, combinations thereof and the like.

In some embodiments, a second domain can include a methylase activity of an enzyme having a classification 2.1.1, methyltransferases, and in certain embodiments, the methyltransferase may have a classification of 2.1.1.29 to 2.1.1.74, inclusive. In some embodiments, a second domain can include a methylase activity of an enzyme having a classification 2.1.1.37. In certain embodiments, a second domain includes a methylase activity that transfers a methyl group to DNA, RNA, protein, small molecule, cytosine or adenine. Additional methylase activities suitable for use in embodiments described herein can be identified and selected as known in the art (e.g., World Wide Web URL neb.com/nebecomm/tech_reference/restriction_enzymes/defaultasp, or rebase.neb.com/cgi-bin/msublist).

In certain embodiments, a second domain can include a demethylase activity. Demethylases are enzymes that remove methyl groups from protein substrates. Non-limiting examples of demethylase activity are histone demethylases (LSD1, PAD 14 and Jumonji C (JmjC) domain family proteins, for example), which can remove methyl groups from specific lysines in histone proteins. In some embodiments, a second domain can include a demethylase activity of an enzyme having a classification 1.14.11.27. Histone demethylase activity may play a role in gene regulation. Novel fusion proteins with demethylase activity, generated as described herein, may prove useful for laboratory or clinical applications, similar to those described above for methylase activities. Methylase and demethylase sequences (e.g., sequences for a histone demethylase) can be accessed at World Wide Web URL ebi.ac.uk/ebisearch/search.ebi ?db=proteinSequences&t=dnmt1.

Non-limiting examples of methylase and demethylase polynucleotides and polypeptides are described hereafter:
DNA methylase Dnmt1 (from *Bos Taurus*, sequences are also known of from other sources)

```
polypeptide:
MPARTAPARVPALASRAFSLPDDVRRRLKDLERDSLTEKECVKEKLNLLHEFLRTEIKNQ

LCDLETKLHKEELSEEGYLAKVKSLLNKDLSLENGAHAFSREANGCLENGSQTSGEDCRV

VMAEKGKPPKPVSRLYTPRRSKSDGETKSEVSSSPRITRKTTRQTTITSHFPRGPAKRKP

EEEPEKVKSDDSVDEEKDQEEKRRRVTSRERVAGLLPAEEPGRVRPGTHMEEEGRDDKEE

KRLRSQTKEPTPKHKAKEEPDRDVRPGGAQAEMNEGEDKDEKRHRSQPKDLASKRRPEEK

EPERVKPQVSDEKDEDEKEEKRRRTTYRELTEKKMTRTKIAVVSKTNPPKCTECLQYLDD

PELRYEQHPPDAVEEIQILTNERLSIFDANESGFESYEDLPQHKLTCFSVYCKRGHLCPI

DTGLIEKDVELLFSGSAKPIYEDDPSPEGGINGKNFGPINEWWIAGFDGGEKALLGFSTS

FAEYILMDPSPEYAPLFSVMQEKIYISKIVVEFLQSNPDSTYEDLINKIETTVPPCMLNL

NRFTEDSLLRHAQFVVEQVESYDRAGDSDEQPIFLSPCMRDLIKLAGVTLGKRRAERRQT

IRQPAKEKDKGPTKATTTKLVYQIFDTFFAEQIEKDDKEDKENAFKRRRCGVCEICQQPE

CGKCKACKDMVKFGGSGRSKQACQKRRCPNMAMKEADDDEEVDDNIPEMPSPKKMHQGKK

KKQNKNRISWVGDAVKTDGKKSYYKKVCIDSETLEVGDCVSVIPDDSSKPLYLARVTALW

EDSSNGQMFHAHWFCAGTDTVLGATSDPLELFLVDECEDMQLSYIHSKVQVIYKAPSENW
```

-continued

AMEGGVDPEALMSEDDGKTYFYQLWYDQDYARFESPPKTQPTEDNKYKFCASCARLAEMR

QKEIPRVVEQLQDLEGRVLYSLATKNGVQYRVGDGVYLPPEAFTFNIKLSSPVKRPRKEP

VDEALYPEHYRKYSDYIKGSNLDAPEPYRIGRIKEIFCSKKSNGRPNETDIKIRVNKFYR

PENTHKSTPASYHADINLLYWSDEEAVVDFKAVQGRCTVEYGEDLPQCLQDFSAGGPDRF

YFLEAYNAKSKSFEDPPNHARSTGNKGKGKGKGKNRTKSQTCEPSELETEIKLPKLRTLD

VFSGCGGLSEGFHQAGISETLWAIEMWDPAAQAFRLNNPGSTVFTEDCNVLLKLVMAGEV

TNSRGQKLPQKGDVEMLCGGPPCQGFSGMNRFNSRTYSKFKNSLVVSFLSYCDYYRPRYF

LLENVRNFVSFKRSMVLKLTLRCLVRMGYQCTFGVLQAGQYGVAQTRRRAIILAAAPGEP

LPLFPEPLHVFAPRACQLSVVVDDKKFVSNITRLSSGPFRTITVRDTMSDLPEIRNGASA

LEISYNGEPQSWFQRQLRGSQYQPILRDHICKDMSALVAARMRHIPLAPGSDWRDLPNIE

VRLSDGTLARKLRYNYHDKKNGCSSSGALRGVCSCVEGKPCEPAARQFNTLIPWCLPHTG

NRHNHWAGLYGRLEWDGFFSTTVTNPEPMGKQGRVLHPEQHRVVSVRECARSQGFPDTYR

LFGNILDKHRQVGNAVPPPLAKAIGLEIKRCMLAKARESASAKIKEEAAKD
(SEQ ID NO: 21)

polynucleotide:
aagatgcctgcccgaaccgccccggcgcgggtgcctgcgctggcctcccgggccttctca ctgcctgacgatgtccgcaggcggctcaaagatttggaaagagatagtttgacagaaaag gaatgtgtgaaggagaaactgaatctcttgcacgaatttctgcggacagaaataaagaat cagttatgtgatttggaaaccaaattgcataaagaagaattatctgaggagggctacctg gctaaagtcaaatccctttttaaataaagatttgtccttggagaacggagctcatgctttc agtcgggaagcgaatggatgtctagagaacgggagccagacaagtggtgaggattgcaga gtggtaatggcagagaaaggcaagccccccaaacctgtctccagactttacacgcccagg agaagcaagtctgatggagaaacaaagtctgaagtctcttctagccccaggattacaagg aagactaccaggcagaccaccatcacatctcatttcccacggggccctgccaaacgaaaa cctgaggaagaacctgaaaaagtgaagtcagacgattctgttgatgaagaaaagaccag gaggaaaagagacgtcgagttacatccagagaacgagttgctgggctgctccctgcagaa gaaccaggaagagtaagaccaggaacacacatggaagaagaaggaagagatgataaagaa gaaaagagactcagaagtcaaaccaaagaaccgacacctaaacacaaagctaaggaggag ccagacagagatgtgaggcctggaggagctcaggctgaaatgaatgaaggagaagacaaa gatgaaaagaggcacagaagtcaacccaaagatctagctagcaaacggagaccagaagaa aaagaacctgaaagagtaaagccacaagtttctgatgagaaagatgaagatgaaaaggag gagaagagacgcagaactacatacagagaactaaccgagaagaaaatgactcgaaccaaa atagccgtagtgtccaagaccaatcctccgaagtgcaccgagtgcttgcagtacctggac gaccctgagctgagatacgagcagcaccccccgatgcggtggaagagatacagatactg accaacgagaggttgtccatctttgatgccaacgaatctggctttgagagttacgaggat ttgcctcagcacaaactaacctgcttcagcgtgtactgtaaacgcggtcacctttgcccg atcgacaccggcctcattgagaaggatgtcgagctcctcttttctggttcagcaaagccg atatatgaggatgacccatctcccgaaggtggtattaatggcaaaaattttggccccata aacgaatggtggattgctggttttgatggaggtgaaaaggctcttcttggctttagcacc tcatttgccgagtatatcttgatggatcccagcccagagtacgcaccactattcagcgtg atgcaggagaagatctatataagtaagatagtggttgagttcctgcagagcaaccctgac tccacctacgaagacctgatcaataagattgagaccaccgttcctccttgtatgctcaac -continued ttgaatcgattcacagaggattctctcctgcggcatgcccagttcgtggtggagcaagta gagagttatgatcgggctggggacagtgacgagcagcccatcttcctgagccctgcatg agagacctcatcaagctggccggggtcaccctgggaaaaaggcgagccgagaggcggcag accatccggcaacccgccaaagagaaggacaagggccccaccaaggccaccaccaccaag ctggtctaccagatctttgacactttctttgcggagcaaattgaaaaagatgacaaggaa gacaaggagaatgccttcaagcgccggcgctgtggcgtctgtgagatttgtcaacagccc gagtgtggaaagtgtaaggcctgtaaggatatggttaaatttggtggtagcggacggagc aagcaggcttgccaaaagaggaggtgtcccaacatggccatgaaggaggcagacgatgac gaggaagtggatgacaatattccagagatgccatcacccaaaaagatgcatcaggggaag aaaaagaagcagaataagaatcggatctcttggttggcgatgccgtcaagactgacggg aagaagagttactacaagaaggtatgcatcgactcggaaaccctggaagtgggggactgt gtttctgtaattccagacgactcttcaaaaccactgtatctagcaagggtcacggcgctg tgggaggacagcagcaatgggcagatgttccatgcccactggttctgtgctgggacggac acggtcctcggggccacatcggaccccctggagctgttcctggttgacgagtgtgaggac atgcagctctcgtacatccacagcaaggtgcaggtcatttataaggcgccctcagagaac tgggccatggagggaggcgtggaccccgaggccctgatgtcagaggacgacgggaagacc tacttctaccagctgtggtacgaccaagactacgcgagatttgagtcccctccgaaaact cagccgacggaggacaacaagtacaagttctgcgcaagctgtgcacgtctggccgaaatg aggcagaaggaaatccccagggtcgtggagcagctccaggacctggaaggccgcgtcctc tacagcctcgccaccaagaacggcgtccagtaccgggtgggcgatggcgtgtacctccct cccgaggccttcaccttcaacatcaagctgtccagtcctgtgaaacgcccccggaaggag cctgtggacgaagctctgtatccagaacactaccggaagtactctgactacatcaagggc agcaacctggatgcccctgagccctaccgtattggccgcataaaggagatcttctgcagc aagaagagcaacggccggcccaatgagacagacatcaagatcagggtcaacaagttctac aggccggagaacacacacaagtctaccccagccagttaccacgcagacatcaacctgctt tactggagcgatgaggaggccgtggtggacttcaaggccgtgcagggccgctgcaccgtg gagtacggagaggacctgcctcagtgcctccaggacttctccgctggtggccccgatcgc ttctattttctcgaggcctataacgccaagagcaaaagctttgaagatcctccgaaccac gcccggagcaccggaaataaagggaaaggaaggggaaaggaaaaaacaggacgaaatct cagacgtgtgagccgagtgaactggagacagaaatcaaactgccgaagctgcggacccctg gacgtgttttccggctgtggggggattgtcggaaggcttccaccaagcaggcatctcggaa acactttgggccatcgagatgtgggaccctgcggcccaggcgttccggttcaacaaccct gggtccacggtgttcacaaaggactgcaacgtcctggtgaagctggtcatggccggggag gtgaccaactcccgcggccagaagctgcttcaaaagggagatgtggagatgttgtgcggc gggccgccctgccagggctttagcggcatgaaccgcttcaactctcgaacctactccaaa ttcaagaactccctggtggtctcttttcctcagctactgtgactactaccggccccgctac ttcctcttggagaacgttcggaacttcgtctccttcaagcgctccatggtcctgaagctg acgctgcgctgcctggtccgcagggggtaccagtgcacctttggcgtgctgcaggctggt cagtacggcgtggcccagactcggaggcgagccatcatcctggctgcagcccctggggag ccactcccgctgttcccggagccgttgcatgtgttcgcaccccgggcctgccagctgagc -continued
```
gtcgtagtggacgacaagaagtttgtcagcaacatcaccaggttgagctcgggtcccttc cgaaccatcaccgtgcgggacaccatgtctgacctccctgagatccggaacggggcctcg gcactggagatttcatacaaccgggagccccagtcctggttccagaggcagctccggggc tcgcagtaccagcccatcctcagggatcatatttgcaaggacatgagcgccttggtggct gcccgcatgcggcacatcccctggccccgggctcggactggcgtgacctgcccaacatt gaggtgcggctctctgacggcaccctggcccggaagctgcggtacaactaccacgacaag aagaacggctgcagcagcagcggcgccctccgtggggtctgctcctgtgtggaaggcaag ccctgtgagcctgcggcccgacagtttaacacccttatccctggtgcctgccccacact gggaacaggcacaaccactgggccggcctctacgggcgtctcgagtgggacggcttcttc agcacaactgtcaccaaccccgagcccatgggcaagcagggccgcgtgctccaccccgag cagcaccgagtggtgagcgtccgggagtgcgcccgctcccagggcttccccgacacctat cggctgttcggcaacatcctagacaagcaccggcaggtgggtaatgctgtgccgccgcca ctggccaaagccatcggcttggagatcaagcgctgcatgttggccaaagcgcgcgagagc gcctcagctaaaatcaaggaggaggctgccaaggactagttctctcctcctatcacccat gtttctgccaccagagatccccaacgtgcactgatattggtgtattttcacatgtcaat cagtcaattcagatgtgtcgtatgcggtgtttgtggccttggctgacatgaaactcttca gtgagatttgcctatcggctaatttggacttantgatcaaactgtgcagtactttgtcca ttctggattttaaaagttttttttttacgcattatatnaaatttaccactgtttgagtggn aattaagactttatgtagnttttatatgttgnaatatttcttcaaaaaatctcttcttaa aaacaaaaaaaaaaaaaaaaaaaaaaaaaaaaaa (SEQ ID NO: 22)
```

Histone demethylase (from Micromonas, other enzymes are also known and many have been isolated from other species)

```
polypeptide:
MWHKDTRAPLTIERCLSSMPSDTADLARESHAWLQKHGAINYGAIDVPPPKPPTPEPEPA

PENAEPEDASPPTTITDELLTERTVAYLRTADMNTTTEKQIRKAIEAELGADLTEKKLVV

RAIVTGFLEDPDKYRDVGKGKGAEERREDAAKAKAAVAKAKAEIEAAKPKPTKPVIIVGA

GPAGLAAARMLTSHGHACVVLEARDRVGGRVHTDSSSLSVPVDMGASIITGCAADAKRRT

GLPWLGVRADPSATIAAQLGLGLKTLGNKLPLYDGVTGELVSDELDARVERHRDALMDRA

RLRVDREGDDATAKMSLAEVIEDELEQAFGENVAPSPAAAAAADGAGEGEEDGEKREKVT

LTARERRLLGWHWANLEYGCSAPLSKISMAHWNQDEPYGGFGGPHCMVRGGYGQITDALA

AGLEIRFKIVVKKVEHFGGEGDAGGVVVHVANGERFEGSACIVTAPLGCLKSGDIEFVPR

LSEAKSVAIQRLGFGRLNKVVMEFEKSFWDDGVDYFGAAREHYAPDAQATGDDPIGGRGR

MFMFWNLKEACGGASVLVALVAGSAAEAMESGDESESSLVASAMGVLRRIFSDRASDVTT

PKKVAVSRWGSDPYAKGSYSYVAVGASADDYDELGRPEESSGGRLLFAGEHTCKEHPDTV

GGAMLTGWRAARHALHVMNGASGLPFDEVFKLVSLEDIAGSDDSEDSDVSGSSDDSDDED

DADRGKKRKKETKKETKKRRGKKGRRVDGEDGPEDDEKARERVRRRLEKEKQERMEQLAR

EQKEMTDGKEEVKRVLRLVSACPDGASAPVDAVTFDGMLEMMPSLETASGRGAFCQCAVA

KMPRAQLASLALKDEGACLAVLATWLEQVPSKPSGKELSSKMLKLLLALDTDAVDARALK

ESGVARVVADRFNAHAIPEIRLLARRCAHHWSKAASAAKARRDAQSSKAGLAPEDTPLGD

FIDDDDASMDDSDSEREYDPDGKRRKKRAEQKPPPKPMTVEEIIESAAGLQEGFAAAEAQ
```

```
RLKLEADAALAAAHAAAADAKAEAIRAEEVAKERLRGVWDAAPRVGKKQKLRMKTFEDFA

KHKTAKREHKKRQRLEREREDAEDARMEAEEAAAAERGAGGSPGGGDTAGGGGVDLAAAA

AEAARVASLGPEERYRENVKKAVRFYVRKQLKQGIKEKKLRGLNKELCGKIEEKIAAKVV

EGSTSLGAPGDSVEAFLSKQRREKVKKMVESYAASYAKAKK  (SEQ ID NO: 23)
```

Assays for methylase or demethylase activity can be performed using techniques and procedures known in the art. For example, methylase activity of a second domain can be assayed by performing DNA or RNA methylation reactions under appropriate conditions for the novel fusion protein, followed by restriction endonuclease digestion of the methylated nucleic acid and non-methylated control nucleic acid to determine if the nucleic acid was protected from cleavage. Demethylase activity can be assayed using a similar technique, where increased cleavage of previously methylated nucleic acid may be the expected result. Assay results can be visualized using common methods, such as separation of cleaved or uncleaved nucleic acids by size using electrophorectic techniques, for example. The term "appropriate conditions" as used herein refers to assay conditions such as salt, buffer, temperature and/or nucleotide sequence conditions necessary to allow partial or full functionality of the second or activity domain (e.g., methylase or demethylase activity domain), for example.

Transcription Factor Activity (Transcription Activator and Repressor Activities)

A second domain sometimes includes a transcription activator activity, in some embodiments. In certain embodiments, a second domain includes a transcription repressor activity. Transcription often is influenced or regulated by a number of factors that allow for a regulated process of transcribing DNA into RNA. An activator can be a DNA-binding protein that can regulate one or more genes by increasing the level of transcription. A repressor can be a DNA-binding protein that can regulate one or more genes by decreasing the level of transcription. The activator may increase transcription via a connected domain which can assist in the formation of the RNA polymerase holoenzyme, or may operate through a coactivator. A coactivator can bind the DNA-binding activator and can contain the domain assisting holoenzyme formation. A particular activator may bind one or more specific coactivators. A repressor may decrease transcription via a connected domain which can block formation of the RNA polymerase by blocking access to sequences in the promoter. A repressor may decrease transcription through a co-repressor. A co-repressor may bind the DNA-binding repressor, or may bind the DNA directly in conjunction with the repressor. Transcription activators and repressors sometimes are referred to as transcription factors.

Novel transcription activator or transcription repressor fusion proteins can be generated by the combination of an association domain, a linker and an activity domain, as described in embodiments presented herein. Fusion proteins described herein, comprising a transcription activator or transcription repressor activity second domain, can be used for many laboratory or clinical applications. Non-limiting examples of transcription factors that contain activator or repressor activity domains for use in embodiments described herein can include: TFIIA, TFIIB, TFIIE, TFIIH, TATA binding protein (also referred to as TFIID), HOX, HSF, HIF, SRY, MYC, Sp1, NF1, CCAAT, GATA, HNF, PIT-1, MyoD, CREB, G-Box, AP-1, STAT, C/EBP-like factors, RAV, AB1, AP2, pocket domains, copper first domains, RUNT, Cold shock factors (csd), SOX, p53, TUBBY, IRF, Homeo domain, Kruppel, TFIIIA, VP16, VP64, p65, ERF repressor domain, MadSID, TATA box binding protein, homologs thereof, and the like.

Non-limiting examples of uses to which fusion proteins with transcription activator activity can be applied, include: targeted gene activation (turning on target genes directly or turning off repressor genes, for example), targeted gene repression (turning on a gene that produces a repressor of other genes, or turning off a gene directly for example). For example, a fusion protein with an association domain that recognizes nucleic acid sequences in erythropoietin or vesicular endothelial growth factor genes functionally coupled to a transcription activator could be useful as specific transcription activators of these genes.

In certain embodiments, the transcription activator activity is a VP16, VP64 or p65 domain of NF kappa B transcription activator activity. In some embodiments, the transcription repressor activity is a Kruppel associated box, ERF repressor domain, MadSID or TATA box binding protein activity. Additional transcription activator activities or transcription repressor activities suitable for use in embodiments described herein can be identified and selected by the artisan using the available nucleic acid or amino acid sequence database tools described above. Examples of transcription activator/repressor sequences described herein can be accessed at World Wide Web URLs ebi.ac.uk/Databases/protein.html and ncbi.nlm.nih.gov/sites/entrez?db=gene.

Non-limiting examples of transcription activator polypeptides and polynucleotides are provided hereafter:

VP16 (TFIID From *Drosophila*)

```
polypeptide:
MSAEKSDKAKISAQIKHVPKDAQVIMSILKELNVQEYEPRVVNQLLEFTFRYVTCILDDA

KVYANHARKKTIDLDDVRLATEVTLDKSFTGPLERHVLAKVADVRNSMPLPPIKPHCGLR

LPPDRYCLTGVNYKLRATNQPKKMTKSAVEGRPLKTVVKPVSSANGPKRPHSVVAKQQVV

TIPKPVIKFTTTTTTKTVGSSGGSGGGGGQEVKSESTGAGGDLKMEVDSDAAAVGSIAGA

SGSGAGSASGGGGGGGSSGVGVAVKREREEEEFEFVTN  (SEQ ID NO: 24)
``` polynucleotide:
ccgatatgtacgtgcacaatttcaatggaataaacaatcttcttgcagcaaagccgacgt aaacataataactatagaagtatgagcgcagagaagtccgataaggccaagatcagtgcc caaatcaagcacgtgccgaaggacgcgcaggtgatcatgtccatcctgaaggagctgaat gtccaggagtacgagccgcgcgtggtcaaccaactgctggagttcaccttccgctatgtc acctgcattctggacgacgccaaggtatacgccaaccatgcgcgcaagaagaccatcgac ttggacgacgtgcgtctggccaccgaggttacgctggacaagagcttcaccgggccgttg gagcgccacgttctagccaaggtggccgacgtgcgcaacagcatgcccctgccacccatt aagccgcactgcggtctccgactgccgcccgaccgctactgtctcaccggcgtcaactac aaactgcgggccactaatcagcccaagaaaatgaccaagtcggcggtggagggccgtcca ctgaagaccgtcgttaagcccgtctccagcgccaatggtccgaagaggccacactccgtg gtggccaagcagcaggtggtgaccattcccaagcccgtcatcaagtttaccaccactacg acaacgaaaacggtgggcagctccggcggatctggggcggcggtggtcaggaggttaag agcgagagcaccggcgccggcggagatctcaagatggaggtggacagcgatgcggcggcc gtgggcagcatcgctggcgcatccggttcgggagcaggaagtgccagcggaggaggagga ggaggaggatcatctggcgttggagtggccgtcaagcgggaacgtgaggaggaggagttt gagtttgtgaccaactagcgaaacgacatcatttaccttaaattaatattcttaaatcag accaaagcacttgcatttggttgagcgaactgggggtctaaatttcaactcgaatgtgaa gtcccaaaaaccttagtatagattcgcccgttaatcattatgaaatctacgttttataca caaatacaactaccagattttcatatt (SEQ ID NO: 25)

VP16 (TFIID from Human)

polypeptide:
MESGKTASPKSMPKDAQMMAQILKDMGITEYEPRVINQMLEFAFRYVTTI

LDDAKIYSSHAKKATVDADDVRLAIQCRADQSFTSPPPRDFLLDIARQRN

QTPLPLIKPYSGPRLPPDRYCLTAPNYRLKSLQKKASTSAGRITVPRLS

VGSVTSRPSTPTLGTPTPQTMSVSTKVGTPMSLTGQRFTVQMPTSQSPA

VKASIPATSAVQNVLINPSLIGSKNILITTNMMSSQNTANESSNALKRK

REDDDDDDDDDDYDNL (SEQ ID NO: 26)

NF Kappa B (p65 domain from Human)

polypeptide:
MDELFPLIFPAEPAQASGPYVEIIEQPKQRGMRFRYKCEGRSAGSIPGERSTDTTKTHPT

IKINGYTGPGTVRISLVTKDPPHRPHPHELVGKDCRDGFYEAELCPDRCIHSFQNLGIQC

VKKRDLEQAISQRIQTNNNPFQVPIEEQRGDYDLNAVRLCFQVTVRDPSGRPLRLPPVLS

HPIFDNRAPNTAELKICRVNRNSGSCLGGDEIFLLCDKVQKEDIEVYFTGPGWEARGSFS

QADVHRQVAIVFRTPPYADPSLQAPVRVSMQLRRPSDRELSEPMEFQYLPDTDDRHRIEE

KRKRTYETFKSIMKKSPFSGPTDPRPPPRRIAVPSRSSASVPKPAPQPYPFTSSLSTINY

DEFPTMVFPSGQISQASALAPAPPQVLPQAPAPAPAPAMVSALAQAPAPVPVLAPGPPQA

VAPPAPKPTQAGEGTLSEALLQLQFDDEDLGALLGNSTDPAVFTDLASVDNSEFQQLLNQ

GIPVAPHTTEPMLMEYPEAITRLVTGAQRPPDPAPAPLGAPGLPNGLLSGDEDFSSIADM

DFSALLSQISS (SEQ ID NO: 27)

polynucleotide:
gaattccggcgaatggctcgtctgtagtgcacgccgcgggcccagctgcgaccccggccc cgccccgggaccccggccatggacgaactgttccccctcatcttcccggcagagccagc ccaggcctctggccctatgtggagatcattgagcagcccaagcagcggggcatgcgctt -continued

```
ccgctacaagtgcgaggggcgctccgcgggcagcatcccaggcgagaggagcacagatac caccaagacccaccccaccatcaagatcaatggctacacaggaccagggacagtgcgcat ctccctggtcaccaaggaccctcctcaccggcctcaccccacgagcttgtaggaaagga ctgccgggatggcttctatgaggctgagctctgcccggaccgctgcatccacagtttcca gaacctgggaatccagtgtgtgaagaagcgggacctggagcaggctatcagtcagcgcat ccagaccaacaacaaccccttccaagttcctatagaagagcagcgtggggactacgacct gaatgctgtgcggctctgcttccaggtgacagtgcgggacccatcaggcaggcccctccg cctgccgcctgtccttcctcatccatctttgacaatcgtgcccccaacactgccgagct caagatctgccgagtgaaccgaaactctggcagctgcctcggtggggatgagatcttcct actgtgtgacaaggtgcagaaagaggacattgaggtgtatttcacgggaccaggctggga ggcccgaggctccttttcgcaagctgatgtgcaccgacaagtggccattgtgttccggac ccctccctacgcagaccccagcctgcaggctcctgtgcgtgtctccatgcagctgcggcg gccttccgaccgggagctcagtgagcccatggaattccagtacctgccagatacagacga tcgtcaccggattgaggagaaacgtaaaaggacatatgagaccttcaagagcatcatgaa gaagagtcctttcagcggacccaccgaccccggcctccacctcgacgcattgctgtgcc ttcccgcagctcagcttctgtccccaagccagcaccccagccctatcccctttacgtcatc cctgagcaccatcaactatgatgagtttcccaccatggtgtttccttctgggcagatcag ccaggcctcggccttggccccggccctccccaagtcctgcccaggctccagcccctgc ccctgctccagccatggtatcagctctggcccaggccccagccctgtcccagtcctagc cccaggccctcctcaggctgtggcccacctgcccccaagcccacccaggctggggaagg aacgctgtcagaggccctgctgcagctgcagtttgatgatgaagacctggggggccttgct tggcaacagcacagacccagctgtgttcacagacctggcatccgtcgacaactccgagtt tcagcagctgctgaaccagggcatacctgtggcccccccacacaactgagcccatgctgat ggagtaccctgaggctataactcgcctagtgacaggggcccagaggcccccccgacccagc tcctgctccactgggggccccggggctccccaatggcctcctttcaggagatgaagactt ctcctccattgcggacatggacttctcagccctgctgagtcagatcagctcctaagggg tgacgcctgccctccccagagcactgg (SEQ ID NO: 28)
```

Assays for transcription activator activity or transcription repressor activity can be performed using techniques and procedures known in the art. For example, transcription activation activity of a second domain can be assayed by determining transcription levels (e.g., in vivo or in vitro) in the presence and absence of a fusion protein comprising the transcription activator activity domain. Under similar conditions, transcription would be expected to be greater in the presence of a functional activator activity. Transcription repressor activity of a second domain can be assayed using a similar technique, where the expected result would be a decrease in the amount of transcript produced. The amount of transcript produced can be determined using hybridization or annealing based methodologies (PCR using a limited number of cycles, saturation hybridization, primer extension and the like, for example).

Release Factor Activity

A second domain can include a release factor activity, in some embodiments. In certain embodiments, a release factor can be a transcription release factor. In some embodiments a release factor can be a translation release factor. A transcription release factor (e.g., Polymerase I transcript release factor (PTRF), transcript release factors 1 and 2 (found in human, mouse and *Drosophila*), vaccinia virus A18R DNA helicase and the like) can act to cause the release of RNA polymerase from template DNA, when the polymerase pauses (e.g., at a lesion such as a thymine dimer) or encounters a transcription termination signal. Some transcription release factors have been shown to increase transcription initiation by freeing the promoter region of a gene to allow reinitiation of transcription. Thus, fusion proteins comprising a transcription release factor activity domain could be useful for targeted gene silencing when operably linked to a nucleic acid association domain that targets specific nucleic acid sequences or structures, by promoting the release of polymerase prior to the completion of transcription. In certain embodiments, a release factor can also stimulate transcription and thus act as a gene activator by allowing increased reinitiation of transcription (e.g., as in the case of PTRF).

In certain embodiments, a transcript release factor can be a translation release factor. A translation release factor can be a class I type (e.g., RF1 in eukaryotes (eRF1), and RF1 and RF2 in prokaryotes), or a class II type release factor (e.g., RF3). Class I translation transcript release factors can participate in termination of protein synthesis by recognizing three stop codons in the mRNA via conserved amino acid motifs and by interactions between a conserved tripeptide (GGQ) and the peptidyltransferase center of the ribosome. Class II release factors can act in conjunction with class I release factors, and have been shown to stimulate the activity of class I release factors in the presence of GTP. RF3 is also postulated to regulate termination coupled events such as interaction with poly(A)-binding protein and interaction with activities responsible for decay of normal and nonsense mRNA.

Transcription and translation are functionally coupled in prokaryotes. Thus, translation release factors that cause termination (premature or normal translation termination, for example) can act to increase transcription termination as well. Without being limited to a particular theory, it is believed that the disruption of transcription, when translation is paused or terminated, may be due to the appearance of secondary structures in the newly transcribed RNA that can act as transcription terminators (e.g., Rho dependent terminators). Thus, fusion proteins comprising a translation release factor activity domain could act to terminate translation by allowing the formation and action of inadvertent transcription terminators in RNA. Therefore, fusion proteins with ER1, EF2, or EF3 translation release factor activity domains may terminate or inhibit transcription.

Novel release factor (e.g., transcription or translation release factor) fusion proteins can be generated by the combination of an association domain, a linker and an activity domain (e.g., release factor activity), as described in embodiments presented herein. Fusion proteins described herein, comprising a release factor activity second domain, can be used for many laboratory or clinical applications. Non-limiting examples of uses to which fusion proteins with release factor activity can be applied, include: gene silencing (turning off gene expression by releasing polymerase or by prematurely terminating translation, which can allow transcription termination in prokaryotes, for example), gene activation (turning on gene expression by allowing reinitiation at the promoter and the like, for example). Examples of release factor sequences described herein can be accessed at World Wide Web URLs ebi.ac.uk/Databases/protein.html and ncbi.nlm.nih.gov/sites/entrez?db=gene.

Assays for release factor activity can be performed using techniques and procedures known in the art. For example, release factor activity of a second domain can be assayed by determining transcription levels (e.g., in vivo or in vitro) in the presence and absence of a fusion protein comprising the release factor activity domain. Under similar conditions, RNA polymerase II transcription would be expected to be decreased in the presence of a functional transcription release factor activity, while RNA polymerase I transcription levels may increase or decrease depending on the level of promoter reinitiation. The length of transcripts also can be determined, where shorter transcripts are expected in the presence of fusion proteins with transcription release factor activity domains. Translation release factor activity domain fusion proteins are expected to show decreased levels of transcription in prokaryotes, due to the uncoupling of transcription and translation. The amount and length of transcript produced can be determined using hybridization or annealing based methodologies (PCR using a limited number of cycles, saturation hybridization, primer extension and the like, for example).

Histone Modification Activity

A second domain sometimes includes a histone modification activity, in some embodiments. Histone proteins are involved in DNA folding and packing to form chromatin. The packing of DNA into chromatin, via winding around histone octamers, can effect gene expression, development and the like. Histones undergo posttranslational modifications that can alter their interaction with DNA. Non-limiting examples of the types of modification that histones may undergo include: methylation, acetylation, phosphorylation, ubiquitination, sumoylation, citrullination, ADP-ribosylation, deamination, and proline isomerization. Combinations of modifications are thought to constitute a code (e.g., "histone code"). Histone modifications act in diverse biological processes such as gene regulation, DNA repair and chromosome condensation (e.g., mitosis). Posttranslational modification of histones sometimes can result in chromatin remodeling, which in turn can play a role in silencing or activating genes or groups of genes that may be coordinately regulated.

Histone modifiers also are thought to be involved in neoplastic transformation. Clinical and experimental evidence has implicated some histone modifier proteins in human malignancies. Histone modifiers also are thought to interact with non-histone proteins to acetylate or deacetylate proteins that may interact with nucleic acids, including, but not limited to transcription factors and co-regulators of transcription. For example, acetylation of PTEN (e.g., a human tumor suppress gene) by the histone acetyltransferase p300/CBP-associated factor (PCAF) can stimulate its activity; conversely, deacetylation of PTEN by SIRT1 (e.g., Sirtuin 1) deacetylase and also by HDAC1 (e.g., histone deacetylase 1) can repress its activity. Additionally, transcription factor and effector molecule, NF kappa B, which is involved in responses to cell stress, is a p50/p65 heterodimer, whose p65 subunit is controlled by acetylation via PCAF and by deacetylation via HDAC3 and HDAC6 (e.g., Histone deacetylase 3 and 6, respectively). Thus, novel fusion proteins with histone modification activity, as described herein, are expected to prove useful for altering gene expression, in chromosome remodeling, in or as part of anti-cancer agents or therapies, and the like or combinations thereof.

Novel fusion proteins, comprising histone modification activity second domains, can be generated by the combination of an association domain, a linker and an activity domain (e.g., histone modification activity), as described in embodiments presented herein. Fusion proteins described herein, comprising a histone modification activity second domain, can be used for many laboratory or clinical applications. Non-limiting examples of uses to which fusion proteins with histone modification activity can be applied, include: chromatin remodeling, gene silencing (turning off gene expression by modification of histones such that genes are no longer accessible to transcription machinery or by posttranscriptional modification of transcription factors or coregulators, for example), gene activation (turning on gene expression by modification of histones such that genes are accessible to transcription machinery, or by posttranscriptional modification of transcription factors or coregulators, for example) developmental regulation (through coordinated chromatin remodeling and gene activation or silencing, for example), anti-cancer agents, anti-cancer therapies (using the ability of histone modifier activity to posttranscriptionally modify transcription factors or coregulators), and the like.

In certain embodiments, a histone modification activity can be a histone deacetylase activity (e.g., enzymes of the classification 3.5.1). Histone deacetylases are classified as Class I (e.g., HDAC's 1, 2, 3 and 8), Class II (e.g., HDAC's 4, 5, 6, 7A, 9 and 10), Class III (e.g., homologs of Sir2 (from yeast) and homologs of Sirtuins (e.g., from humans, SIRT1-6)) and Class IV (e.g., HDAC 11). Histone deacetylases remove acetyl groups from a ε-N-acetyl lysine amino acid on a histone. Removal of acetyl groups from lysine amino acids can increase the positive charge of histone tails and promote high-affinity binding between the histones and DNA backbone. The increased DNA binding condenses DNA structure, sometimes preventing transcription. As noted above, deacetylation of non-histone proteins also may play a role in transcription.

In some embodiments, a histone modification activity can be a histone acetyltransferase activity (e.g., enzymes of the classification 2.3.1). In certain embodiments, the histone modification activity is a histone acetyltransferase enzyme of the classification 2.3.1.48. Non-limiting examples of histone acetyltransferase activities include; CBP/p300, Esa1, Gcn5, HAT1, p160 family, PCAF, TAFII250 and Tip60. Histone acetyltransferases acetylate conserved lysine amino acids on histone proteins. Histone acetylation is generally linked to transcriptional activation. Acetylation of lysines may decrease the positive charge of histone tails, thus allowing DNA unpacking and expansion, which in turn may make genes more accessible to transcription machinery. Acetylation of lysines also may generate binding sites for specific protein-protein interaction domains. As noted above, acetylation of non-histone proteins also may play a role in transcription.

In certain embodiments, a histone modification activity can be a histone methyltransferase activity (e.g., enzymes of the classification 2.1.1). In some embodiments, the histone modification activity is a histone methyltransferase enzyme of the classification 2.1.1.43. Histone methyltransferases fall into two types, histone-lysine N-methyltransferases and histone-arginine N-methyltransferases. Histone methyltransferases catalyze the transfer of one to three methyl groups from S-adenosyl methionine (e.g., SAM) to lysine or Arginine residues of histone proteins. Histone methylation may play a role in epigenetic gene regulation. As noted above methylated histones may play a role in transcription regulation. Methylated histones bind DNA more tightly and, thus, may inhibit transcription. Examples of histone modifier sequences described herein can be accessed at World Wide Web URLs ebi.ac.uk/Databases/protein.html and ncbi.nlm.nih.gov/sites/entrez?db=gene.

Functional assays for histone modification activity can be performed using techniques and procedures known in the art. For example, histone modification activity by a second domain of a fusion protein can be assayed by monitoring transcription activation or repression of reporter genes engineered to be responsive to modification by a fusion protein, in some embodiments. In certain embodiments, in vivo or in vitro chromatin remodeling can be assessed after treatment with a fusion protein comprising a histone modification activity second domain. Assay results can be visualized using common chromatin visualization methods or by assaying the product of a reporter gene engineered to be responsive to modification by a fusion protein.

Nucleic Acid Association Activity in a Second Domain

A second domain can include a nucleic acid association activity, in some embodiments. In some embodiments, a nucleic acid association activity includes an RNA association activity. In certain embodiments, the RNA association activity can be a RNA recognition motif (RRM) or ribonucleoprotein domain (RNP) activity. Nucleic acid association domains and activities are described herein for first domain activities, and certain embodiments described for a first domain often are applicable to a second domain. First domain nucleic acid association motifs, sequences and structures, discussed above, also can be used as a second domain activity, in certain embodiments. In some embodiments, the first domain can include a DNA association activity. Fusion proteins with a first and second nucleic acid association domain could prove useful for gene silencing, enzymatic action of an independent molecule on sequences held in juxtaposition, scaffolding for chromatin remodeling, genome editing, combinations thereof and the like.

In some embodiments, a second domain includes an RNA cleavage activity, in addition to a RNA association activity. In certain embodiments, the RNA cleavage activity is a Dicer activity. Dicer is an endoribonuclease in the RNase III family. Dicer cleaves double stranded RNA (dsRNA) and pre-microRNA (miRNA) into short double stranded fragments, sometimes referred to as small interfering RNA (siRNA). miRNA's regulate mRNA translation, whereas siRNAs direct RNA destruction via the RNA interference (RNAi) pathway. Dicer contains two RNase III domains and a PAZ domain. Dicer catalyzes the first step in the RNA interference pathway and initiates formation of the RNA-induced silencing complex (RISC). RISC has an endonuclease catalytic component that may play a role in degrading mRNA whose sequence is complementary to that of the siRNA strand guide. siRNAs and miRNAs then direct a RISC to cleave mRNA or block its translation (RNAi).

Novel fusion proteins, comprising nucleic acid association activity second domains, can be generated by the combination of an association domain, a linker and an activity domain (e.g., a second nucleic acid association domain), as described in embodiments presented herein. Fusion proteins described herein, comprising a nucleic acid association activity second domain, can be used for many laboratory or clinical applications. Non-limiting examples of uses to which fusion proteins with nucleic acid association activity can be applied, include: message stabilization (e.g., protect the message from degradation, thereby allowing more protein to be made from the same message), RNA cleavage or attachment (e.g., each nucleic acid association domain (the first domain and second domain, for example) associates with a RNA, holding them in juxtaposition such that, a catalytic activity of one of the nucleic acids can function, or a function provided by an independent activity can act on the nucleic acids held in each domain), and the like. Examples of nucleic acid association second domain sequences can be found at World Wide Web URL ebi.ac.uk/Databases/protein.html. Nucleic acid association polypeptides described herein that bind RNA can be utilized in the second domain. As noted above, nucleic acid association activity can be assayed and visualized using standard techniques and protocols known to the artisan and available in laboratory manuals such as Maniatis, T., E. F. Fritsch and J. Sambrook (1982) *Molecular Cloning: a Laboratory Manual*; Cold Spring Harbor Laboratory, Cold Spring Harbor, N.Y. Gel shift assays can be used to investigate DNA-DNA, RNA-DNA and RNA-RNA association interactions. Nuclease digestion assays (e.g., S1, T1, P1 and the like) also can be used to detect the presence or absence of associated nucleic acids. Primer extension, or amplification methods also can be used to detect the presence of absence of associated nucleic acids.

Functional assays for nucleic acid association activity can be performed using techniques and procedures known in the art. For example, nucleic acid association activity that also includes a catalytic activity associated with the nucleic acid (e.g., ribozyme) can be assayed by detecting the desired cleavage reaction in the presence or absence of a fusion protein. Dicer activity can be assayed by initiation of specific mRNA degradation. The results of the assays can be visualized using various electrophorectic, reporter gene, or molecular beacon assay systems.

Linkers

A first domain and second domain may be joined to one another in a fusion protein via a bond in some embodiments. Thus, in certain embodiments, a first domain and a second domain are not joined by a multi-atom linker. In some embodiments, however, a fusion protein includes a first domain operably or functionally linked to a second domain via a linker. The term "linker" as used herein refers to a suitable connector for linking domains in a fusion protein. The linker may be associated with a domain by a direct attachment, indirect attachment, covalent attachment or non-covalent attachment, in some embodiments. A linker can include a suitable arrangement of atoms, and sometimes is a polymer or small molecule linker. In certain embodiments, a linker includes amino acids. A linker also may be a polynucleotide that separates polynucleotides that encode polypeptides in a fusion protein. That is, a linker sometimes can refer to the nucleic acid sequence that encodes an amino acid linker sequence that separates the first domain from a second domain.

A linker sometimes includes neutral amino acids (e.g., serine, threonine, alanine, glycine, valine, leucine, isoleucine, cysteine, methionine). In some embodiments, a linker is about 70% to about 100% of one or more amino acids selected from the group consisting of glycine, alanine, threonine and serine (e.g., 70% or more, 75% or more, 80% or more, 85% or more, 90% or more, 95% or more, 99% or more, or 100%). The length of the linker between the first and second domain can play a role in the ability of a second domain to successfully perform its function. In some embodiments, the linker can be about 5 amino acids to about 50 amino acids in length (e.g., about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58 or 59 amino acids in length). In some embodiments, a linker includes one or more of the following amino acid sequences: GSGGGGSAAGASAS (SEQ ID NO: 1), STSGGSGGTGGS (SEQ ID NO: 2), GGTGGTGGSGGTG (SEQ ID NO: 3), fragments thereof, concatemers thereof or combinations thereof, and the like. A linker can be a polynucleotide that encodes one of the foregoing, in some embodiments.

A nucleic acid encoding a linker can be combined with polynucleotides encoding a first domain and a second domain using standard recombinant DNA techniques (e.g., cloning, ligation, amplification of overlapping nucleic acid fragments, and the like), in certain embodiments. A linker also can be included in a synthesized nucleic acid which encodes a first domain, the linker and a second domain. In some embodiments, a linker can be a bifunctional linker with binding pair groups. A suitable binding pair can be utilized to link a first and second domain, including, but not limited to, antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, nucleic acid/complementary nucleic acid (e.g., DNA, RNA, PNA). Covalent linkages also can be effected by a binding pair, such as a chemical reactive group/complementary chemical reactive group (e.g., sulfhydryl/maleimide, sulfhydryl/haloacetyl derivative, amine/isotriocyanate, amine/succinimidyl ester, and amine/sulfonyl halides). Methods for attaching such binding pairs to reagents and effecting binding are known to the artisan.

Methods and Compositions

In some embodiments, an isolated nucleic acid can include a nucleotide sequence that encodes a fusion protein as described in embodiments presented herein. A fusion protein often is a polypeptide or protein resulting from the operable or functional joining of a first domain and a second domain via a linker, or a nucleotide sequence, nucleotide sequences or nucleic acid reagents encoding said polypeptide or protein. As noted above, and described in further detail herein, nucleic acid sequences encoding fusion proteins described herein can include all or part of a nucleic acid reagent.

A nucleic acid (e.g., synthesized nucleic acids, isolated nucleic acids, nucleic acid reagents and the like) encoding a fusion protein can be expressed to produce the fusion protein. Expression can be in vivo, or in vitro (e.g., cell-free system). In certain embodiments, a cell can include a nucleic acid and/or a fusion protein as described in embodiments presented herein. In some embodiments, a cell-free system can include a nucleic acid and/or a fusion protein as described in embodiments presented herein. Nucleic acids described herein can be introduced into cells using methods readily known in the art. Cell-free systems can be prepared using known methods, or the artisan can purchase commercially available cell-free systems (e.g., Expressway™, Invitrogen, Carlsbad Calif., World Wide Web URL invitrogen.com/site/us/en/home/Products-and-Services/Applications/Protein-Expression-and-Analysis/Protein-Expression/Cell-Free-Expression.html).

A fusion protein can be used in methods for modifying a target nucleic acid, in some embodiments. Methods for modifying a target nucleic acid can include: contacting the target nucleic acid with a fusion protein under modification conditions, where the target nucleic acid is modified by a fusion protein. Fusion proteins described herein with transcription factor or histone modifying activity domains are non-limiting examples of fusion proteins useful for modifying target nucleic acids. Modification conditions are known in the art, and often are a set of conditions that permit a detectable level of modification.

A fusion protein can be manufactured using a method comprising: (a) selecting an activity domain; (b) selecting an association domain; and (c) joining the selected activity domain and association domain or linking the activity domain and the association domain via a linker. In some embodiments, the peptides or proteins comprising the domains can be prepared with an activated N terminal and/or C terminal group suitable for conjugation to other molecules. For example, an association domain can be prepared with an activated carboxy terminal group that can be conjugated to the N terminus of a linker peptide or protein. Fusion proteins described herein can be assembled using peptides or proteins conjugated to a linker, in some embodiments. In certain embodiments, the order of steps (a) and (b) can be reversed.

A fusion protein can be manufactured using a method comprising: (a) selecting a first polynucleotide encoding an activity domain; (b) selecting a second polynucleotide encoding an association domain that improves the specificity of the activity domain; (c) joining the first polynucleotide and the second polynucleotide; and (d) operably linking the joined first polynucleotide and second polynucleotide to a transcription promoter. The first polynucleotide and the second polynucleotide may be joined via a third polynucleotide encoding a linker (e.g., the first polynucleotide and the second polynucleotide are linked). In certain embodiments, one or two of the following are in a nucleic acid and the omitted components are cloned into the nucleic acid: first polynucleotide, second polynucleotide and third polynucleotide. In some embodiments, the third polynucleotide is in a nucleic acid, and the first polynucleotide and/or the second polynucleotide are inserted into the nucleic acid. In certain embodiments, the third polynucleotide and one of the first polynucleotide or second polynucleotide are in a nucleic acid, and the remaining first polynucleotide or second polynucleotide is inserted into the nucleic acid. The term "selected" as used herein refers to the act of identifying and/or choosing a domain or activity from amino acid/protein or nucleotide sequence databases for inclusion in a fusion protein. The term "joining or linking the selected activity and association domains via a linker" refers to combination of selected domains with an amino acid connector (e.g., linker), which may or may not have a function other than connection of the first and second domain. In some embodiments, a first and second domain can be linked via a linker in a single nucleic acid synthesized by amplification of nucleic acid fragments or by nucleic acid synthesizers.

A nucleic acid can include one or more suitable polynucleotides, which may facilitate one or more functions, which can include, without limitation, insertion of a polynucleotide, replication of a nucleic acid or portion thereof and transcription of a nucleic acid or portion thereof. A nucleic acid can contain, in certain embodiments, one or more of the following components: (i) association domain polynucleotide and/or insertion site for association domain polynucleotide; (ii) activity domain polynucleotide and/or insertion site for an activity domain polynucleotide; (iii) linker polynucleotide (e.g., encodes an amino acid linker between the association domain and activity domain); and (iv) intron. Components (i) and (ii) may include sites that facilitate insertion (i.e., cloning) of an association domain polynucleotide or activity domain polynucleotide, which in some embodiments, can have one or more restriction enzyme sites and/or topoisomerase sites (e.g., att sites). A set of nucleic acids may be provided in some embodiments, each of which include a linker component (iii) of a different length and/or base composition. An intron (i.e., component (iv)) sometimes is a synthetic intron, which can be useful for expression in eukaryotic cells or systems. A nucleic acid also may include one or more selection markers (e.g., antibiotic resistance marker), one or more UTRs and/or one or more promoters, in some embodiments. A polynucleotide in a nucleic acid (e.g., activity domain polynucleotide and/or association domain polynucleotide) may be mutated by a suitable mutation method, including, without limitation PCR mediated site-directed mutagenesis optionally followed by restriction enzyme treatment (e.g., Dpn I treatment), for example.

In certain embodiments, a nucleic acid encoding a fusion protein can be replicated. In some embodiments, a nucleic acid is replicated by one or more methods selected from amplification, insertion into a DNA expression construction, insertion into a DNA construct suitable for replication of a nucleic acid and the like.

In certain embodiments, the method of manufacture further includes expressing a fusion protein. In some embodiments, a fusion protein can be expressed in a cell free system. In certain embodiments, the fusion protein can be expressed in a cell. In some embodiments, the method further includes testing the activity of the expressed fusion protein.

Polynucleotides and Polypeptides

A nucleic acid (e.g., also referred to herein as nucleic acid reagent, target nucleic acid, target nucleotide sequence, nucleotide sequence of interest or nucleic acid region of interest) can be from a suitable source or composition. A nucleic acid can be a suitable type, including, for example, DNA, cDNA, gDNA (genomic DNA), RNA, siRNA (short inhibitory RNA), RNAi, tRNA (transfer RNA) or mRNA (messenger RNA), for example, and can be in a suitable form (e.g., linear, circular, supercoiled, single-stranded, double-stranded, and the like). A nucleic acid can also include DNA or RNA analogs (e.g., containing base analogs, sugar analogs and/or a non-native backbone and the like). It is understood that the term "nucleic acid" does not refer to or infer a specific length of the polynucleotide chain, thus polynucleotides and oligonucleotides are also included in the definition. It is also understood that the term "nucleic acid" does not refer to or infer an origin of the polynucleotide chain, thus nucleic acids obtained from an organism or synthesized chemically are also included in the definition. Deoxyribonucleotides include deoxyadenosine, deoxycytidine, deoxyguanosine and deoxythymidine. For RNA, the uracil base is uridine.

In some embodiments, nucleic acids can be used to make nucleic acid libraries and/or combinatorial nucleic acid libraries (e.g., libraries of association domains, and activity domains joined by linker sequences). In some embodiments, the methods described herein can include inserting nucleic acid of the library into an expression construct or nucleic acid reagent. In certain embodiments, the nucleic acid libraries described herein can be combined with or made part of a nucleic acid reagent using standard recombinant DNA methods available to one of skill in the art, or as described herein. In some embodiments, each nucleic acid of the nucleic acid library can include polynucleotide species linked in series. In certain embodiments, the polynucleotide species can be separated from one another by linkers.

A nucleic acid sometimes is a plasmid, phage, autonomously replicating sequence (ARS), centromere, artificial chromosome, yeast artificial chromosome (e.g., YAC) or other nucleic acid able to replicate or be replicated in a host cell. In certain embodiments a nucleic acid can be from a library or can be obtained from enzymatically digested, sheared or sonicated genomic DNA (e.g., fragmented) from an organism of interest. In some embodiments, nucleic acid subjected to fragmentation or cleavage may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000 or 10000 base pairs. Fragments can be generated by a suitable method in the art, and the average, mean or nominal length of nucleic acid fragments can be controlled by selecting an appropriate fragment-generating procedure by the person of ordinary skill. In some embodiments, the fragmented DNA can be size selected to obtain nucleic acid fragments of a particular size range. In some embodiments, a nucleic acid library as described herein can be inserted into an expression construct. In certain embodiments, a nucleic acid library as described herein can be inserted to yeast artificial chromosomes.

Nucleic acid can be fragmented by various methods known to the person of ordinary skill, which include without limitation, physical, chemical and enzymic processes. Examples of such processes are described in U.S. Patent Application Publication No. 20050112590 (published on May 26, 2005, entitled "Fragmentation-based methods and systems for sequence variation detection and discovery," naming Van Den Boom et al.). Certain processes can be selected by the person of ordinary skill to generate non-specifically cleaved fragments or specifically cleaved fragments. Examples of processes that can generate non-specifically cleaved fragment sample nucleic acid include, without limitation, contacting sample nucleic acid with apparatus that expose nucleic acid to shearing force (e.g., passing nucleic acid through a syringe needle; use of a French press); exposing sample nucleic acid to irradiation (e.g., gamma, x-ray, UV irradiation; fragment sizes can be controlled by irradiation intensity); boiling nucleic acid in water (e.g., yields about 500 base pair fragments) and exposing nucleic acid to an acid and base hydrolysis process.

Nucleic acid may be specifically cleaved by contacting the nucleic acid with one or more specific cleavage agents. The term "specific cleavage agent" as used herein refers to an agent, sometimes a chemical or an enzyme that can cleave a nucleic acid at one or more specific sites. Specific cleavage agents often will cleave specifically according to a particular nucleotide sequence at a particular site. Examples of enzymic specific cleavage agents include, without limitation, endonucleases (e.g., DNase (e.g., DNase I, II); RNase (e.g., RNase E, F, H, P); Cleavase™ enzyme; Taq DNA polymerase; *E. coli* DNA polymerase I and eukaryotic structure-specific endonucleases; murine FEN-1 endonucleases; type I, II or III restriction endonucleases such as Acc I, Afl III, Alu I, Alw44 I, Apa I, Asn I, Ava I, Ava II, BamH I, Ban II, Bcl I, Bgl I. Bgl II, Bln I, Bsm I, BssH II, BstE II, Cfo I, Cla I, Dde I, Dpn I, Dra I, EcIX I, EcoR I, EcoR I, EcoR II, EcoR V, Hae II, Hae II, Hind III, Hind III, Hpa I, Hpa II, Kpn I, Ksp I, Mlu I, MluN I, Msp I, Nci I, Nco I, Nde I, Nde II, Nhe I, Not I, Nru I, Nsi I, Pst I, Pvu I, Pvu II, Rsa I, Sac I, Sal I, Sau3A I, Sca I, ScrF I, Sfi I, Sma I, Spe I, Sph I, Ssp I, Stu I, Sty I, Swa I, Taq I, Xba I, Xho I); glycosylases (e.g., uracil-DNA glycolsylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1,N6-etheno-adenine DNA glycosylase); exonucleases (e.g., exonuclease III); ribozymes, and DNAzymes. Sample nucleic acid may be treated with a chemical agent, or synthesized using modified nucleotides, and the modified nucleic acid may be cleaved. In non-limiting examples, sample nucleic acid may be treated with (i) alkylating agents such as methylnitrosourea that generate several alkylated bases, including N3-methyladenine and N3-methylguanine, which are recognized and cleaved by alkyl purine DNA-glycosylase; (ii) sodium bisulfite, which causes deamination of cytosine residues in DNA to form uracil residues that can be cleaved by uracil N-glycosylase; and (iii) a chemical agent that converts guanine to its oxidized form, 8-hydroxyguanine, which can be cleaved by formamidopyrimidine DNA N-glycosylase. Examples of chemical cleavage processes include, without limitation, alkylation, (e.g., alkylation of phosphorothioate-modified nucleic acid); cleavage of acid lability of P3'-N5'-phosphoroamidate-containing nucleic acid; and osmium tetroxide and piperidine treatment of nucleic acid.

As used herein, the term "complementary cleavage reactions" refers to cleavage reactions that are carried out on the same nucleic acid using different cleavage reagents or by altering the cleavage specificity of the same cleavage reagent such that alternate cleavage patterns of the same target or reference nucleic acid or protein are generated. In certain embodiments, nucleic acids of interest may be treated with one or more specific cleavage agents (e.g., 1, 2, 3, 4, 5, 6, 7, 8, 9, 10 or more specific cleavage agents) in one or more reaction vessels (e.g., nucleic acid of interest is treated with each specific cleavage agent in a separate vessel).

A nucleic acid suitable for use in the embodiments described herein sometimes is amplified by an amplification process known in the art (e.g., PCR, RT-PCR and the like). Nucleic acid amplification may be particularly beneficial when using organisms that are typically difficult to culture (e.g., slow growing, require specialize culture conditions and the like). In some embodiments, amplification and/or PCR can be used to add linkers or "sticky-ends" to nucleotide sequences to be joined to create a novel fusion protein as described herein and/or facilitate inserting assembled nucleotide sequences into expression constructions of nucleic acid reagents. Amplification is discussed in further detail below.

In some embodiments, a nucleic acid reagent sometimes can be stably integrated into the chromosome of the host organism. In certain embodiments, a nucleic acid reagent sometimes can be used to stably integrate an accessory nucleic acid into the chromosome of the host organism, or a nucleic acid reagent can be used to delete of a portion of the host chromosome, in certain embodiments (e.g., knock in or knock outs using fusion proteins with a specific nucleic acid association domain and an endonuclease activity domain, in the presence of an accessory nucleic acid). Such nucleic acid reagents (e.g., nucleic acids or genetically modified organisms whose altered genome confers a selectable trait to the organism) can be selected for their ability to guide production of a desired protein or nucleic acid molecule. When desired, the nucleic acid reagent can be altered such that codons encode for (i) the same amino acid, using a different tRNA than that specified in the native sequence, or (ii) a different amino acid than is normal, including unconventional or unnatural amino acids (including detectably labeled amino acids). As described herein, the term "native sequence" refers to an unmodified nucleotide sequence as found in its natural setting (e.g., a nucleotide sequence as found in an organism).

A nucleic acid or nucleic acid reagent can include certain elements often selected according to the intended use of the nucleic acid. One or more of the following elements can be included in or excluded from a nucleic acid reagent. A nucleic acid reagent, for example, may include one or more or all of the following nucleotide elements: one or more promoter elements, one or more 5' untranslated regions (5'UTRs), one or more regions into which a target nucleotide sequence may be inserted (an "insertion element"), one or more target nucleotide sequences, one or more 3' untranslated regions (3'UTRs), and one or more selection elements. A nucleic acid reagent can be provided with one or more of such elements and other elements may be inserted into the nucleic acid before the nucleic acid is introduced into the desired organism. In some embodiments, a provided nucleic acid reagent includes a promoter, 5'UTR, optional 3'UTR and insertion element(s) by which a target nucleotide sequence is inserted (i.e., cloned) into the nucleotide acid reagent. In certain embodiments, a provided nucleic acid reagent includes a promoter, insertion element(s) and optional 3'UTR, and a 5' UTR/target nucleotide sequence is inserted with an optional 3'UTR. The elements can be arranged in a suitable order for expression in the chosen expression system (e.g., expression in a chosen organism, or expression in a cell free system, for example), and in some embodiments a nucleic acid reagent includes the following elements in the 5' to 3' direction: (1) promoter element, 5'UTR, and insertion element(s); (2) promoter element, 5'UTR, and target nucleotide sequence; (3) promoter element, 5'UTR, insertion element(s) and 3'UTR; and (4) promoter element, 5'UTR, target nucleotide sequence and 3'UTR.

A promoter element often is required for DNA synthesis and/or RNA synthesis. A promoter element often includes a region of DNA that can facilitate the transcription of a particular gene, by providing a start site for the synthesis of RNA corresponding to a gene. Promoters generally are located near the genes they regulate, are located upstream of the gene (e.g., 5' of the gene), and are on the same strand of DNA as the sense strand of the gene, in some embodiments.

A promoter often interacts with a RNA polymerase. A polymerase is an enzyme that catalyses synthesis of nucleic acids using a preexisting nucleic acid reagent. When the template is a DNA template, an RNA molecule is transcribed before protein is synthesized. Enzymes having polymerase activity suitable for use in the present methods include a polymerase that is active in the chosen system with the chosen template to synthesize protein. In some embodiments, a promoter (e.g., a heterologous promoter) also referred to herein as a promoter element, can be operably linked to a nucleotide sequence or an open reading frame (ORF). Transcription from the promoter element can catalyze the synthesis of an RNA corresponding to the nucleotide sequence or ORF sequence operably linked to the promoter, which in turn leads to synthesis of a desired peptide, polypeptide or protein. The term "operably linked" as used herein with respect to promoters refers to a nucleotide sequence (e.g., a coding sequence) present on the same nucleic acid molecule as a promoter element and whose expression is under the control of said promoter element.

Promoter elements sometimes exhibit responsiveness to regulatory control. Promoter elements also sometimes can be regulated by a selective agent. That is, transcription from promoter elements sometimes can be turned on, turned off, up-regulated or down-regulated, in response to a change in environmental, nutritional or internal conditions or signals (e.g., heat inducible promoters, light regulated promoters, feedback regulated promoters, hormone influenced promoters, tissue specific promoters, oxygen and pH influenced promoters, promoters that are responsive to selective agents (e.g., kanamycin) and the like, for example). Promoters influenced by environmental, nutritional or internal signals frequently are influenced by a signal (direct or indirect) that binds at or near the promoter and increases or decreases expression of the target sequence under certain conditions.

Non-limiting examples of selective or regulatory agents that can influence transcription from a promoter element used in embodiments described herein include, without limitation, (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotics (e.g., β-lactamase), β-galactosidase, green fluorescent protein (GFP), yellow fluorescent protein (YFP), red fluorescent protein (RFP), cyan fluorescent protein (CFP), and cell surface proteins); (5) nucleic acid segments that bind products that are otherwise detrimental to cell survival and/or function; (6) nucleic acid segments that otherwise inhibit the activity of a nucleic acid segment described in Nos. 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, and the like). In some embodiments, the regulatory or selective agent can be added to change the existing growth conditions to which the organism is subjected (e.g., growth in liquid culture, growth in a fermentor, growth on solid nutrient plates and the like for example).

In some embodiments, regulation of a promoter element can be used to alter (e.g., increase, add, decrease or substantially eliminate) the activity of a peptide, polypeptide or protein (e.g., enzyme activity for example). For example, a microorganism can be engineered by genetic modification to express a nucleic acid reagent that can add a novel activity (e.g., an activity not normally found in the host organism) or increase the expression of an existing activity by increasing transcription from a homologous or heterologous promoter operably linked to a nucleotide sequence of interest (e.g., homologous or heterologous nucleotide sequence of interest), in certain embodiments. In some embodiments, a microorganism can be engineered by genetic modification to express a nucleic acid reagent that can decrease expression of an activity by decreasing or substantially eliminating transcription from a homologous or heterologous promoter operably linked to a nucleotide sequence of interest, in certain embodiments.

In some embodiments, a polynucleotide species, as described herein, can be in operable linkage with one or more promoters. In certain embodiments, the polynucleotide species are in operable linkage with one promoter. In some embodiments, the promoter can be a constitutive promoter suitable for expression of the polynucleotide encoding a fusion protein. The term "constitutive promoters suitable for expression" as used herein refers to the strength of the promoter and the ability of the promoter to initiate sufficient rounds of transcription that an activity or nucleic acid encoding the activity can be detected (e.g., mRNA from the gene and/or the activity associated with the gene, for example). Thus, the promoter or promoters chosen are chosen due to their ability to initiate sufficient rounds of transcription that the desired activities are present in sufficient quantity to produce acceptable levels of the desired result. In some embodiments, promoters responsive to changes in the growth medium or environment (e.g., regulatable promoters or conditionally regulated promoters for example) can be used to express nucleic acids from nucleic acid reagents encoding fusion proteins constructed according to methods described herein.

A nucleic acid reagent may include a polynucleotide sequence 80% or more identical to nucleic acid sequences encoding domains or activities described herein, as found in nucleic acid sequence databases available to the artisan (or to the complementary sequences). That is, a nucleotide sequence that is at least 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical to a nucleotide sequence described herein can be utilized. The term "identical" as used herein refers to two or more nucleotide sequences having substantially the same nucleotide sequence when compared to each other. One test for determining whether two nucleotide sequences or amino acids sequences are substantially identical is to determine the percent of identical nucleotide sequences or amino acid sequences shared.

Calculations of sequence identity can be performed as follows. Sequences are aligned for optimal comparison purposes (e.g., gaps can be introduced in one or both of a first and a second amino acid or nucleotide sequence for optimal alignment and non-homologous sequences can be disregarded for comparison purposes). The length of a reference sequence aligned for comparison purposes is sometimes 30% or more, 40% or more, 50% or more, often 60% or more, and more often 70% or more, 80% or more, 90% or more, or 100% of the length of the reference sequence. The nucleotides or amino acids at corresponding nucleotide or polypeptide positions, respectively, are then compared among the two sequences. When a position in the first sequence is occupied by the same nucleotide or amino acid as the corresponding position in the second sequence, the nucleotides or amino acids are deemed to be identical at that position. The percent identity between the two sequences is a function of the number of identical positions shared by the sequences, taking into account the number of gaps, and the length of each gap, introduced for optimal alignment of the two sequences.

Comparison of sequences and determination of percent identity between two sequences can be accomplished using a mathematical algorithm. Percent identity between two amino acid or nucleotide sequences can be determined using the algorithm of Meyers & Miller, CABIOS 4: 11-17 (1989), which has been incorporated into the ALIGN program (version 2.0), using a PAM120 weight residue table, a gap length penalty of 12 and a gap penalty of 4. Also, percent identity between two amino acid sequences can be determined using the Needleman & Wunsch, J. Mol. Biol. 48: 444-453 (1970) algorithm which has been incorporated into the GAP program in the GCG software package (available at the http address www.gcg.com), using either a Blossum 62 matrix or a PAM250 matrix, and a gap weight of 16, 14, 12, 10, 8, 6, or 4 and a length weight of 1, 2, 3, 4, 5, or 6. Percent identity between two nucleotide sequences can be determined using the GAP program in the GCG software package (available at http address www.gcg.com), using a NWSgapdna.CMP matrix and a gap weight of 40, 50, 60, 70, or 80 and a length weight of 1, 2, 3, 4, 5, or 6. A set of parameters often used is a Blossum 62 scoring matrix with a gap open penalty of 12, a gap extend penalty of 4, and a frameshift gap penalty of 5.

Sequence identity can also be determined by hybridization assays conducted under stringent conditions. As use herein, the term "stringent conditions" refers to conditions for hybridization and washing. Stringent conditions are known to those skilled in the art and can be found in Current Protocols in Molecular Biology, John Wiley & Sons, N.Y., 6.3.1-6.3.6 (1989). Aqueous and non-aqueous methods are described in that reference and either can be used. An example of stringent hybridization conditions is hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Often, stringent hybridization conditions are hybridization in 6× sodium chloride/sodium citrate (SSC) at about 45° C., followed by one or more washes in 0.2×SSC, 0.1% SDS at 65° C. More often, stringency conditions are 0.5M sodium phosphate, 7% SDS at 65° C., followed by one or more washes at 0.2×SSC, 1% SDS at 65° C.

As noted above, nucleic acid reagents may also include one or more 5' UTR's, and one or more 3'UTR's. A 5' UTR may include one or more elements endogenous to the nucleotide sequence from which it originates, and sometimes includes one or more exogenous elements. A 5' UTR can originate from a suitable nucleic acid, such as genomic DNA, plasmid DNA, RNA or mRNA, for example, from a suitable organism (e.g., virus, bacterium, yeast, fungi, plant, insect or mammal). The artisan may select appropriate elements for the 5' UTR based upon the chosen expression system (e.g., expression in a chosen organism, or expression in a cell free system, for example). A 5' UTR sometimes includes one or more of the following elements known to the artisan: enhancer sequences (e.g., transcriptional or translational), transcription initiation site, transcription factor binding site, translation regulation site, translation initiation site, translation factor binding site, accessory protein binding site, feedback regulation agent binding sites, Pribnow box, TATA box, -35 element, E-box (helix-loop-helix binding element), ribosome binding site, replicon, internal ribosome entry site (IRES), silencer element and the like. In some embodiments, a promoter element may be isolated such that 5' UTR elements necessary for proper conditional regulation are contained in the promoter element fragment, or within a functional subsequence of a promoter element fragment.

A 5'UTR in the nucleic acid reagent can include a translational enhancer nucleotide sequence. A translational enhancer nucleotide sequence often is located between the promoter and the target nucleotide sequence in a nucleic acid reagent. A translational enhancer sequence often binds to a ribosome, sometimes is an 18S rRNA-binding ribonucleotide sequence (i.e., a 40S ribosome binding sequence) and sometimes is an internal ribosome entry sequence (IRES). An IRES generally forms an RNA scaffold with precisely placed RNA tertiary structures that contact a 40S ribosomal subunit via a number of specific intermolecular interactions. Examples of ribosomal enhancer sequences are known and can be identified by the artisan (e.g., Mignone et al., Nucleic Acids Research 33: D141-D146 (2005); Paulous et al., Nucleic Acids Research 31: 722-733 (2003); Akbergenov et al., Nucleic Acids Research 32: 239-247 (2004); Mignone et al., Genome Biology 3(3): reviews0004.1-0001.10 (2002); Gallie, Nucleic Acids Research 30: 3401-3411 (2002); Shaloiko et al., http address www.interscience.wiley.com, DOI: 10.1002/bit.20267; and Gallie et al., Nucleic Acids Research 15: 3257-3273 (1987)).

A translational enhancer sequence sometimes is a eukaryotic sequence, such as a Kozak consensus sequence or other sequence (e.g., hydroid polyp sequence, GenBank accession no. U07128). A translational enhancer sequence sometimes is a prokaryotic sequence, such as a Shine-Dalgarno consensus sequence. In certain embodiments, the translational enhancer sequence is a viral nucleotide sequence. A translational enhancer sequence sometimes is from a 5' UTR of a plant virus, such as Tobacco Mosaic Virus (TMV), Alfalfa Mosaic Virus (AMV); Tobacco Etch Virus (ETV); Potato Virus Y (PVY); Turnip Mosaic (poty) Virus and Pea Seed Borne Mosaic Virus, for example. In certain embodiments, an omega sequence about 67 bases in length from TMV is included in the nucleic acid reagent as a translational enhancer sequence (e.g., devoid of guanosine nucleotides and includes a 25 nucleotide long poly (CAA) central region).

A 3' UTR may include one or more elements endogenous to the nucleotide sequence from which it originates and sometimes includes one or more exogenous elements. A 3' UTR may originate from a suitable nucleic acid, such as genomic DNA, plasmid DNA, RNA or mRNA, for example, from a suitable organism (e.g., a virus, bacterium, yeast, fungi, plant, insect or mammal). The artisan can select appropriate elements for the 3' UTR based upon the chosen expression system (e.g., expression in a chosen organism, for example). A 3' UTR sometimes includes one or more of the following elements known to the artisan: transcription regulation site, transcription initiation site, transcription termination site, transcription factor binding site, translation regulation site, translation termination site, translation initiation site, translation factor binding site, ribosome binding site, replicon, enhancer element, silencer element and polyadenosine tail. A 3' UTR often includes a polyadenosine tail and sometimes does not, and if a polyadenosine tail is present, one or more adenosine moieties may be added or deleted from it (e.g., about 5, about 10, about 15, about 20, about 25, about 30, about 35, about 40, about 45 or about 50 adenosine moieties may be added or subtracted).

In some embodiments, modification of a 5' UTR and/or a 3' UTR can be used to alter (e.g., increase, add, decrease or substantially eliminate) the activity of a promoter. Alteration of the promoter activity can in turn alter the activity of a peptide, polypeptide or protein (e.g., enzyme activity for example), by a change in transcription of the nucleotide sequence(s) of interest from an operably linked promoter element comprising the modified 5' or 3' UTR. For example, a microorganism can be engineered by genetic modification to express a nucleic acid reagent comprising a modified 5' or 3' UTR that can add a novel activity (e.g., an activity not normally found in the host organism) or increase the expression of an existing activity by increasing transcription from a homologous or heterologous promoter operably linked to a nucleotide sequence of interest (e.g., homologous or heterologous nucleotide sequence of interest), in certain embodiments. In some embodiments, a microorganism can be engineered by genetic modification to express a nucleic acid reagent comprising a modified 5' or 3' UTR that can decrease the expression of an activity by decreasing or substantially eliminating transcription from a homologous or heterologous promoter operably linked to a nucleotide sequence of interest, in certain embodiments.

A nucleotide reagent sometimes can include a target nucleotide sequence. A "target nucleotide sequence" as used herein encodes a nucleic acid, peptide, polypeptide or protein of interest, and may be a ribonucleotide sequence or a deoxyribonucleotide sequence. A target nucleic acid sometimes is an untranslated ribonucleic acid and sometimes is a translated ribonucleic acid. An untranslated ribonucleic acid may include, but is not limited to, a small interfering ribonucleic acid (sRNA), a short hairpin ribonucleic acid (shRNA), microRNA (miRNA), other ribonucleic acid capable of RNA interference (RNAi), an antisense ribonucleic acid, or a ribozyme. A translatable target nucleotide sequence (e.g., a target ribonucleotide sequence) sometimes encodes a peptide, polypeptide or protein, which are sometimes referred to herein as "target peptides," "target polypeptides" or "target proteins."

A peptide, polypeptide or protein, or an activity catalyzed by one or more peptides, polypeptides or proteins, may be encoded by a target nucleotide sequence and may be selected by a person of ordinary skill in the art. Representative proteins include enzymes (e.g., endonuclease, acetyltransferase, and the like), proteins with nucleic acid association domains (e.g., transcription factors, receptors, and the like), antibodies, serum proteins (e.g., albumin), membrane bound proteins, hormones (e.g., growth hormone, erythropoietin, insulin, etc.), cytokines, etc., and include naturally occurring and exogenously expressed polypeptides. Representative activities (e.g., enzymes or nucleic acid association activity) include a suitable activity associated with a desired nucleic acid modification (e.g., chromatin remodeling, genome editing, and the like), or expression regulation (e.g., transcription repression, transcription activation). The term "enzyme" as used herein refers to a protein which can act as a catalyst to induce a chemical change in other compounds, thereby producing one or more products from one or more substrates.

The term "protein" as used herein refers to a molecule having a sequence of amino acids linked by peptide bonds. This term includes fusion proteins, oligopeptides, peptides, cyclic peptides, polypeptides and polypeptide derivatives, whether native or recombinant, and also includes fragments, derivatives, homologs, and variants thereof. A peptide sometimes is in the range of about 5 amino acids to about 70 amino acids in length (e.g., about 5 amino acids, about 10, about 15, about 20, about 25, about 30, about 35, about 40, about 45, about 50, about 55, about 60, about 65 and about 70 amino acids in length). A protein or polypeptide sometimes is of intracellular origin (e.g., located in the nucleus, cytosol, or interstitial space of host cells in vivo) and sometimes is a cell membrane protein in vivo. In some embodiments (described above, and in further detail below in Engineering and Alteration Methods), a genetic modification can result in a modification (e.g., increase, substantially increase, decrease or substantially decrease) of a target activity.

A translatable nucleotide sequence generally is located between a start codon (AUG in ribonucleic acids and ATG in deoxyribonucleic acids) and a stop codon (e.g., UAA (ochre), UAG (amber) or UGA (opal) in ribonucleic acids and TAA, TAG or TGA in deoxyribonucleic acids), and sometimes is referred to herein as an "open reading frame" (ORF). A nucleic acid reagent sometimes includes one or more ORFs. An ORF may be from a suitable source, sometimes from genomic DNA, mRNA, reverse transcribed RNA or complementary DNA (cDNA), synthesized oligonucleotide, or a nucleic acid library comprising one or more of the foregoing, and is from a suitable organism species that contains a nucleotide sequence of interest, protein of interest, or activity of interest. Non-limiting examples of organisms from which an ORF can be obtained include: algae, bacteria, yeast, fungi, plant (e.g., corn, wheat, barley, rice), human, insect, nematode, bovine, equine, canine, feline, rat or mouse, for example.

A nucleic acid reagent sometimes includes a nucleotide sequence adjacent to an ORF that is translated in conjunction with the ORF and encodes an amino acid tag. The tag-encoding nucleotide sequence is located 3' and/or 5' of an ORF in the nucleic acid reagent, thereby encoding a tag at the C-terminus or N-terminus of the protein or peptide encoded by the ORF. A tag that does not abrogate in vitro transcription and/or translation may be utilized and may be appropriately selected by the artisan. Tags may facilitate isolation and/or purification of the desired ORF product from culture or fermentation media.

A tag sometimes specifically binds a molecule or moiety of a solid phase or a detectable label, for example, thereby having utility for isolating, purifying and/or detecting a protein or peptide encoded by the ORF. In some embodiments, a tag includes one or more of the following elements: FLAG (e.g., DYKDDDDKG (SEQ ID NO: 29)), V5 (e.g., GKPIPNPLLGLDST (SEQ ID NO: 30)), c-MYC (e.g., EQKLISEEDL (SEQ ID NO: 31)), HSV (e.g., QPELAPEDPED (SEQ ID NO: 32)), influenza hemaglutinin, HA (e.g., YPY- DVPDYA (SEQ ID NO: 33)), VSV-G (e.g., YTDIEMNR-LGK (SEQ ID NO: 34)), bacterial glutathione-S-transferase, maltose binding protein, a streptavidin- or avidin-binding tag (e.g., pcDNA™6 BioEase™ Gateway® Biotinylation System (Invitrogen)), thioredoxin, β-galactosidase, VSV-glycoprotein, a fluorescent protein (e.g., green fluorescent protein or one of its many color variants (e.g., yellow, red, blue)), a polylysine or polyarginine sequence, a polyhistidine sequence (e.g., His6 (SEQ ID NO: 35) or other sequence that chelates a metal (e.g., cobalt, zinc, copper), and/or a cysteine-rich sequence that binds to an arsenic-containing molecule. In certain embodiments, a cysteine-rich tag includes the amino acid sequence CC-Xn-CC (SEQ ID NO: 36), wherein X is an amino acid and n is 1 to 3, and the cysteine-rich sequence sometimes is CCPGCC (SEQ ID NO: 37). In certain embodiments, the tag includes a cysteine-rich element and a polyhistidine element (e.g., CCPGCC (SEQ ID NO: 37) and His6 (SEQ ID NO: 35)).

A tag often conveniently binds to a binding partner. For example, some tags bind to an antibody (e.g., FLAG) and sometimes specifically bind to a small molecule. For example, a polyhistidine tag specifically chelates a bivalent metal, such as copper, zinc and cobalt; a polylysine or polyarginine tag specifically binds to a zinc finger; a glutathione S-transferase tag binds to glutathione; and a cysteine-rich tag specifically binds to an arsenic-containing molecule. Arsenic-containing molecules include LUMIO™ agents (Invitrogen, California), such as FlAsH™ (EDT2[4',5'-bis(1,3,2-dithioarsolan-2-yl)fluorescein-(1,2-ethanedithiol)2]) and ReAsH reagents (e.g., U.S. Pat. No. 5,932,474 to Tsien et al., entitled "Target Sequences for Synthetic Molecules;" U.S. Pat. No. 6,054,271 to Tsien et al., entitled "Methods of Using Synthetic Molecules and Target Sequences;" U.S. Pat. Nos. 6,451,569 and 6,008,378; published U.S. Patent Application 2003/0083373, and published PCT Patent Application WO 99/21013, all to Tsien et al. and all entitled "Synthetic Molecules that Specifically React with Target Sequences"). Such antibodies and small molecules sometimes are linked to a solid phase for convenient isolation of the target protein or target peptide.

A tag sometimes includes a sequence that localizes a translated protein or peptide to a component in a system, which is referred to as a "signal sequence" or "localization signal sequence" herein. A signal sequence often is incorporated at the N-terminus of a target protein or target peptide, and sometimes is incorporated at the C-terminus. Examples of signal sequences are known to the artisan, are readily incorporated into a nucleic acid reagent, and often are selected according to the organism in which expression of the nucleic acid reagent is performed. A signal sequence in some embodiments localizes a translated protein or peptide to a cell membrane. Examples of signal sequences include, but are not limited to, a nucleus targeting signal (e.g., steroid receptor sequence and N-terminal sequence of SV40 virus large T antigen); mitochondrial targeting signal (e.g., amino acid sequence that forms an amphipathic helix); peroxisome targeting signal (e.g., C-terminal sequence in YFG from S. cerevisiae); and a secretion signal (e.g., N-terminal sequences from invertase, mating factor alpha, PHO5 and SUC2 in S. cerevisiae; multiple N-terminal sequences of B. subtilisi proteins (e.g., Tjalsma et al., Microbiol. Molec. Biol. Rev. 64: 515-547 (2000)); alpha amylase signal sequence (e.g., U.S. Pat. No. 6,288,302); pectate lyase signal sequence (e.g., U.S. Pat. No. 5,846,818); precollagen signal sequence (e.g., U.S. Pat. No. 5,712,114); OmpA signal sequence (e.g., U.S. Pat. No. 5,470,719); lam beta signal sequence (e.g., U.S. Pat. No. 5,389,529); B. brevis signal sequence (e.g., U.S. Pat. No. 5,232,841); and P. pastoris signal sequence (e.g., U.S. Pat. No. 5,268,273)).

A tag sometimes is directly adjacent to the amino acid sequence encoded by an ORF (i.e., there is no intervening sequence) and sometimes a tag is substantially adjacent to an ORF encoded amino acid sequence (e.g., an intervening sequence is present). An intervening sequence sometimes includes a recognition site for a protease, which is useful for cleaving a tag from a target protein or peptide. In some embodiments, the intervening sequence is cleaved by Factor Xa (e.g., recognition site I (E/D)GR), thrombin (e.g., recognition site LVPRGS (SEQ ID NO: 38)), enterokinase (e.g., recognition site DDDDK (SEQ ID NO: 39)), TEV protease (e.g., recognition site ENLYFQG (SEQ ID NO: 40)) or PreScission™ protease (e.g., recognition site LEVLFQGP (SEQ ID NO: 41)), for example.

An intervening sequence sometimes is referred to herein as a "linker sequence," and may be of a suitable length selected by the artisan. A linker sequence between a first and second domain, as described above, is distinct from the linker referred to as an intervening sequence between a promoter and ORF. An intervening sequence sometimes is about 1 to about 20 amino acids in length, and sometimes about 5 to 10 amino acids in length. The artisan may select a linker or an intervening sequence length to substantially preserve target protein or peptide function (e.g., a tag may reduce target protein or peptide function unless separated by a linker), to enhance disassociation of a tag from a target protein or peptide when a protease cleavage site is present (e.g., cleavage may be enhanced when a linker is present), and/or to enhance interaction of a tag/target protein product with a solid phase. A linker can be of a suitable nucleotide or amino acid content, and where an amino acid sequence often includes a higher proportion of amino acids having relatively short side chains (e.g., glycine, alanine, serine and threonine). Thus, a nucleic acid reagent may contain a domain linker (e.g., linker that joins a first and second domain) and an intervening sequence, in some embodiments.

A "linker" also may be a polynucleotide that separates polynucleotides that encode polypeptides in a nucleic acid. A linker can be of a suitable length, and can be, without limitation, about 200 base pairs or less, about 150 base pairs or less, about 100 base pairs or less or about 50 base pairs or less (e.g., about 10, 20, 30, 40, 50, 60, 70, 80, 90, 100, 110, 120, 130, 140, 150, 160, 170, 180 or 190). A linker often does not include a promoter polynucleotide. A nucleic acid in some embodiments can include a single promoter, a single operon and a single terminator, where the operon includes no linker, or includes one or more linkers between polynucleotides that encode polypeptides. A nucleic acid in certain embodiments may include multiple (e.g., two or more) promoter-polynucleotide units (where the polynucleotide encodes a polypeptide) each separated by a linker.

A nucleic acid reagent sometimes includes a stop codon between a tag element and an insertion element or ORF, which can be useful for translating an ORF with or without the tag. Mutant tRNA molecules that recognize stop codons (described above) suppress translation termination and thereby are designated "suppressor tRNAs." Suppressor tRNAs can result in the insertion of amino acids and continuation of translation past stop codons (e.g., U.S. Patent Application No. 60/587,583, filed Jul. 14, 2004, entitled "Production of Fusion Proteins by Cell-Free Protein Synthesis,"; Eggertsson, et al., (1988) Microbiological Review 52(3):354-374, and Engleerg-Kukla, et al. (1996) in *Escherichia coli* and *Salmonella* Cellular and Molecular Biology, Chapter 60, pps 909-921, Neidhardt, et al. eds., ASM Press, Washington, D.C.). A number of suppressor tRNAs are known, including but not limited to, supE, supP, supD, supF and supZ suppressors, which suppress the termination of translation of the amber stop codon; supB, gIT, supL, supN, supC and supM suppressors, which suppress the function of the ochre stop codon and glyT, trpT and Su-9 suppressors, which suppress the function of the opal stop codon. In general, suppressor tRNAs contain one or more mutations in the anti-codon loop of the tRNA that allows the tRNA to base pair with a codon that ordinarily functions as a stop codon. The mutant tRNA is charged with its cognate amino acid residue and the cognate amino acid residue is inserted into the translating polypeptide when the stop codon is encountered. Mutations that enhance the efficiency of termination suppressors (i.e., increase stop codon read-through) have been identified. These include, but are not limited to, mutations in the uar gene (also known as the prfA gene), mutations in the ups gene, mutations in the sueA, sueB and sueC genes, mutations in the rpsD (ramA) and rpsE (spcA) genes and mutations in the rplL gene.

Thus, a nucleic acid reagent comprising a stop codon located between an ORF and a tag can yield a translated ORF alone when no suppressor tRNA is present in the translation system, and can yield a translated ORF-tag fusion when a suppressor tRNA is present in the system. Suppressor tRNA can be generated in cells transfected with a nucleic acid encoding the tRNA (e.g., a replication incompetent adenovirus containing the human tRNA-Ser suppressor gene can be transfected into cells, or a YAC containing a yeast or bacterial tRNA suppressor gene can be transfected into yeast cells, for example). Vectors for synthesizing suppressor tRNA and for translating ORFs with or without a tag are available to the artisan (e.g., Tag-On-Demand™ kit (Invitrogen Corporation, California); Tag-On-Demand™ Suppressor Supernatant Instruction Manual, Version B, 6 Jun. 2003, at http address www.invitrogen.com/content/sfs/manuals/tagondemand_supernatant_man.pdf; Tag-On-Demand™ Gateway® Vector Instruction Manual, Version B, 20 Jun., 2003 at http address www.invitrogen.com/content/sfs/manuals/tagondemand_vectors_man.pdf; and Capone et al., Amber, ochre and opal suppressor tRNA genes derived from a human serine tRNA gene. EMBO J. 4:213, 1985).

A convenient cloning strategy known in the art may be utilized to incorporate an element, such as an ORF, into a nucleic acid reagent, in some embodiments. Known methods can be utilized to insert an element into the template independent of an insertion element, such as (1) cleaving the template at one or more existing restriction enzyme sites and ligating an element of interest and (2) adding restriction enzyme sites to the template by hybridizing oligonucleotide primers that include one or more suitable restriction enzyme sites and amplifying by polymerase chain reaction (described in greater detail herein). Other cloning strategies take advantage of one or more insertion sites present or inserted into the nucleic acid reagent, such as an oligonucleotide primer hybridization site for PCR, for example, and others described hereafter. In some embodiments, a cloning strategy can be combined with genetic manipulation such as recombination (e.g., recombination of a nucleic acid reagent with a nucleotide sequence of interest into the genome of the organism to be modified, as described further below). In some embodiments, the cloned ORF(s) can produce (directly or indirectly) lycopene, by engineering a microorganism with one or more ORFs of interest, which microorganism includes one or more altered activities selected from the group consisting of.

In some embodiments, the nucleic acid reagent includes one or more recombinase insertion sites. A recombinase insertion site is a recognition sequence on a nucleic acid molecule that participates in an integration/recombination reaction by recombination proteins. For example, the recombination site for Cre recombinase is loxP, which is a 34 base pair sequence included of two 13 base pair inverted repeats (serving as the recombinase binding sites) flanking an 8 base pair core sequence (e.g., FIG. 1 of Sauer, B., Curr. Opin. Biotech. 5:521-527 (1994)). Other examples of recombination sites include attB, attP, attL, and attR sequences, and mutants, fragments, variants and derivatives thereof, which are recognized by the recombination protein λ Int and by the auxiliary proteins integration host factor (IHF), FIS and excisionase (Xis) (e.g., U.S. Pat. Nos. 5,888,732; 6,143,557; 6,171,861; 6,270,969; 6,277,608; and 6,720,140; U.S. patent application Ser. No. 09/517,466, filed Mar. 2, 2000, and 09/732,914, filed Aug. 14, 2003, and in U.S. patent publication no. 2002-0007051-A1; Landy, Curr. Opin. Biotech. 3:699-707 (1993)).

Examples of recombinase cloning nucleic acids are in Gateway® systems (Invitrogen, California), which include at least one recombination site for cloning a desired nucleic acid molecules in vivo or in vitro. In some embodiments, the system utilizes vectors that contain at least two different site-specific recombination sites, often based on the bacteriophage lambda system (e.g., att1 and att2), and are mutated from the wild-type (att0) sites. Each mutated site has a unique specificity for its cognate partner att site (i.e., its binding partner recombination site) of the same type (for example attB1 with attP1, or attL1 with attR1) and will not cross-react with recombination sites of the other mutant type or with the wild-type att0 site. Different site specificities allow directional cloning or linkage of desired molecules thus providing desired orientation of the cloned molecules. Nucleic acid fragments flanked by recombination sites are cloned and subcloned using the Gateway® system by replacing a selectable marker (for example, ccdB) flanked by att sites on the recipient plasmid molecule, sometimes termed the Destination Vector. Desired clones are then selected by transformation of a ccdB sensitive host strain and positive selection for a marker on the recipient molecule. Similar strategies for negative selection (e.g., use of toxic genes) can be used in other organisms such as thymidine kinase (TK) in mammals and insects.

A recombination system useful for engineering yeast is outlined briefly. The system makes use of the ura3 gene (e.g., for S. cerevisiae and C. albicans, for example) or ura4 and ura5 genes (e.g., for S. pombe, for example) and toxicity of the nucleotide analogue 5-Fluoroorotic acid (5-FOA). The ura3 or ura4 and ura5 genes encode orotine-5'-monophosphate (OMP) dicarboxylase. Yeast with an active ura3 or ura4 and ura5 gene (phenotypically Ura+) convert 5-FOA to fluorodeoxyuridine, which is toxic to yeast cells. Yeast carrying a mutation in the appropriate gene(s) or having a knock out of the appropriate gene(s) can grow in the presence of 5-FOA, if the media is also supplemented with uracil.

A nucleic acid engineering construct can be made which may include the URA3 gene or cassette (for S. cerevisiae), flanked on either side by the same nucleotide sequence in the same orientation. The ura3 cassette includes a promoter, the ura3 gene and a functional transcription terminator. Target sequences which direct the construct to a particular nucleic acid region of interest in the organism to be engineered are added such that the target sequences are adjacent to and abut the flanking sequences on either side of the ura3 cassette. Yeast can be transformed with the engineering construct and plated on minimal media without uracil. Colonies can be screened by PCR to determine those transformants that have the engineering construct inserted in the proper location in the genome. Checking insertion location prior to selecting for recombination of the ura3 cassette may reduce the number of incorrect clones carried through to later stages of the procedure. Correctly inserted transformants can then be replica plated on minimal media containing 5-FOA to select for recombination of the ura3 cassette out of the construct, leaving a disrupted gene and an identifiable footprint (e.g., nucleotide sequence) that can be use to verify the presence of the disrupted gene. The technique described is useful for disrupting or "knocking out" gene function, but also can be used to insert genes or constructs into a host organisms genome in a targeted, sequence specific manner.

In certain embodiments, a nucleic acid reagent includes one or more topoisomerase insertion sites. A topoisomerase insertion site is a defined nucleotide sequence recognized and bound by a site-specific topoisomerase. For example, the nucleotide sequence 5'-(C/T)CCTT-3' is a topoisomerase recognition site bound specifically by most poxvirus topoisomerases, including vaccinia virus DNA topoisomerase I. After binding to the recognition sequence, the topoisomerase cleaves the strand at the 3'-most thymidine of the recognition site to produce a nucleotide sequence comprising 5'-(C/T)CCTT-PO4-TOPO, a complex of the topoisomerase covalently bound to the 3' phosphate via a tyrosine in the topoisomerase (e.g., Shuman, J. Biol. Chem. 266:11372-11379, 1991; Sekiguchi and Shuman, Nucl. Acids Res. 22:5360-5365, 1994; U.S. Pat. No. 5,766,891; PCT/US95/16099; and PCT/US98/12372). In comparison, the nucleotide sequence 5'-GCAACTT-3' is a topoisomerase recognition site for type IA E. coli topoisomerase III. An element to be inserted often is combined with topoisomerase-reacted template and thereby incorporated into the nucleic acid reagent (e.g., World Wide Web URL invitrogen.com/downloads/F-13512_Topo_Flyer.pdf; invitrogen.com/content/sfs/brochures/710_021849%20_B_TOPOCloning_bro.pdf; TOPO TA Cloning® Kit and Zero Blunt® TOPO® Cloning Kit product information).

A nucleic acid reagent sometimes contains one or more origin of replication (ORI) elements. In some embodiments, a template includes two or more ORIs, where one functions efficiently in one organism (e.g., a bacterium) and another functions efficiently in another organism (e.g., a eukaryote, like yeast for example). In some embodiments, an ORI may function efficiently in one species (e.g., S. cerevisiae, for example) and another ORI may function efficiently in a different species (e.g., S. pombe, for example). A nucleic acid reagent also sometimes includes one or more transcription regulation sites.

A nucleic acid reagent can include one or more selection elements (e.g., elements for selection of the presence of the nucleic acid reagent, and not for activation of a promoter element which can be selectively regulated). Selection elements often are utilized using known processes to determine whether a nucleic acid reagent is included in a cell. In some embodiments, a nucleic acid reagent includes two or more selection elements, where one functions efficiently in one organism and another functions efficiently in another organism. Examples of selection elements include, but are not limited to, (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotics (e.g., β-lactamase), β-galactosidase, green fluorescent protein (GFP), yellow fluorescent protein (YFP), red fluorescent protein (RFP), cyan fluorescent protein (CFP), and cell surface proteins); (5) nucleic acid segments that bind products that are otherwise detrimental to cell survival and/or function; (6) nucleic acid segments that otherwise inhibit the activity of a nucleic acid segment described in Nos. 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, and the like).

A nucleic acid reagent is of a suitable form useful for in vivo and/or in vitro transcription and/or translation. A nucleic acid sometimes is a plasmid, such as a supercoiled plasmid, sometimes is a yeast artificial chromosome (e.g., YAC), sometimes is a linear nucleic acid (e.g., a linear nucleic acid produced by PCR or by restriction digest), sometimes is single-stranded and sometimes is double-stranded. A nucleic acid reagent sometimes is prepared by an amplification process, such as a polymerase chain reaction (PCR) process or transcription-mediated amplification process (TMA). In TMA, two enzymes are used in an isothermal reaction to produce amplification products detected by light emission (see, e.g., Biochemistry 1996 Jun. 25; 35(25):8429-38 and http address www.devicelink.com/ivdt/archive/00/11/007.html). Standard PCR processes are known (e.g., U.S. Pat. Nos. 4,683,202; 4,683,195; 4,965,188; and 5,656,493), and generally are performed in cycles. Each cycle includes heat denaturation, in which hybrid nucleic acids dissociate; cooling, in which primer oligonucleotides hybridize; and extension of the oligonucleotides by a polymerase (i.e., Taq polymerase). An example of a PCR cyclical process is given below. Multiple cycles frequently are performed using a commercially available thermal cycler. PCR amplification products sometimes are stored for a time at a lower temperature (e.g., at 4° C.) and sometimes are frozen (e.g., at −20° C.) before analysis.

In some embodiments, a nucleic acid reagent, protein reagent, protein fragment reagent or other reagent described herein is isolated or purified. A nucleic acid reagent, protein reagent, protein fragment reagent or other reagent described herein can be purified from a cell or organism. The term "isolated" as used herein refers to material removed from its original environment (e.g., the natural environment if it is naturally occurring, or a host cell if expressed exogenously), and thus is altered "by the hand of man" from its original environment. The term "purified" as used herein with reference to molecules does not refer to absolute purity. Rather, "purified" refers to a substance in a composition that contains fewer substance species in the same class (e.g., nucleic acid or protein species) other than the substance of interest in comparison to the sample from which it originated. "Purified," if a nucleic acid or protein for example, refers to a substance in a composition that contains fewer nucleic acid species or protein species other than the nucleic acid or protein of interest in comparison to the sample from which it originated.

Sometimes, a protein or nucleic acid is "substantially pure," indicating that the protein or nucleic acid represents at least 50% of protein or nucleic acid on a mass basis of the composition. Often, a substantially pure protein or nucleic acid is at least 75% on a mass basis of the composition, and sometimes at least 95% on a mass basis of the composition. An isolated nucleic acid generally is provided with fewer non-nucleic acid components (e.g., protein, lipid) than the amount of components present in a source sample. The term "purified" as used herein refers to sample nucleic acid provided that contains fewer nucleic acid species than in the sample source from which the sample nucleic acid is derived.

The term "amplified" as used herein refers to subjecting nucleic acid of a cell, organism or sample to a process that linearly or exponentially generates amplicon nucleic acids having the same or substantially the same nucleotide sequence as the nucleotide sequence of the nucleic acid in the sample, or portion thereof. As noted above, the nucleic acids used to prepare nucleic acid reagents as described herein can be subjected to fragmentation or cleavage.

Amplification of nucleic acids is sometimes necessary when dealing with organisms that are difficult to culture. The terms "amplify", "amplification", "amplification reaction", or "amplifying" as used herein refers to an in vitro process suitable for multiplying the copies of a target sequence of nucleic acid. Amplification sometimes refers to an "exponential" increase in target nucleic acid. However, "amplifying" as used herein can also refer to linear increases in the numbers of a select target sequence of nucleic acid, but is different than a one-time, single primer extension step. In some embodiments, a limited amplification reaction, also known as pre-amplification, can be performed. Pre-amplification is a method in which a limited amount of amplification occurs due to a small number of cycles, for example 10 cycles, being performed. Pre-amplification can allow some amplification, but stops amplification prior to the exponential phase, and typically produces about 500 copies of the desired nucleotide sequence(s). Use of pre-amplification may also limit inaccuracies associated with depleted reactants in standard PCR reactions.

Where amplification may be desired, a suitable amplification technique can be utilized. Non-limiting examples of methods for amplification of polynucleotides include, polymerase chain reaction (PCR); ligation amplification (or ligase chain reaction (LCR)); amplification methods based on the use of Q-beta replicase or template-dependent polymerase (see US Patent Publication Number US20050287592); helicase-dependant isothermal amplification (Vincent et al., "Helicase-dependent isothermal DNA amplification". EMBO reports 5 (8): 795-800 (2004)); strand displacement amplification (SDA); thermophilic SDA nucleotide sequence based amplification (3SR or NASBA) and transcription-associated amplification (TAA). Non-limiting examples of PCR amplification methods include standard PCR, AFLP-PCR, Allele-specific PCR, Alu-PCR, Asymmetric PCR, Colony PCR, Hot start PCR, Inverse PCR (IPCR), In situ PCR (ISH), Intersequence-specific PCR (ISSR-PCR), Long PCR, Multiplex PCR, Nested PCR, Quantitative PCR, Reverse Transcriptase PCR (RT-PCR), Real Time PCR, Single cell PCR, Solid phase PCR, combinations thereof, and the like. Reagents and hardware for conducting PCR are commercially available.

Protocols for conducting the various type of PCR listed above are known in the art. PCR conditions can be dependent upon primer sequences, target abundance, and the desired amount of amplification, and therefore, one of skill in the art may choose from a number of PCR protocols available (see, e.g., U.S. Pat. Nos. 4,683,195 and 4,683,202; and PCR Protocols: A Guide to Methods and Applications, Innis et al., eds, 1990. PCR often is carried out as an automated process with a thermostable enzyme. In this process, the temperature of the reaction mixture is cycled through a denaturing region, a primer-annealing region, and an extension reaction region automatically. Machines specifically adapted for this purpose are commercially available. A non-limiting example of a PCR protocol that may be suitable for embodiments described herein is, treating the sample at 95° C. for 5 minutes; repeating forty-five cycles of 95° C. for 1 minute, 59° C. for 1 minute, 10 seconds, and 72° C. for 1 minute 30 seconds; and then treating the sample at 72° C. for 5 minutes. Additional PCR protocols are described in the example section. Multiple cycles frequently are performed using a commercially available thermal cycler. Suitable isothermal amplification processes known and selected by the person of ordinary skill in the art also may be applied, in certain embodiments. In some embodiments, nucleic acids encoding polypeptides with a desired activity can be isolated by amplifying the desired sequence from an organism having the desired activity using oligonucleotides or primers designed based on sequences described herein Amplified, isolated and/or purified nucleic acids can be cloned into the recombinant DNA vectors described in Figures herein or into suitable commercially available recombinant DNA vectors. Cloning of nucleotide sequences of interest into recombinant DNA vectors can facilitate further manipulations of the nucleic acids for preparation of nucleic acid reagents, (e.g., alteration of nucleotide sequences by mutagenesis, homologous recombination, amplification and the like). Standard cloning procedures (e.g., enzymic digestion, ligation, and the like) are known in the art and can be found in Maniatis, T., E. F. Fritsch and J. Sambrook (1982) Molecular Cloning: a Laboratory Manual; Cold Spring Harbor Laboratory, Cold Spring Harbor, N.Y.

In some embodiments, nucleotide sequences prepared by isolation or amplification can be used, without further modification, to add a nucleic acid encoding a fusion protein described herein to a microorganism and thereby generate a genetically modified or engineered microorganism. In certain embodiments, nucleotide sequences prepared by isolation or amplification can be genetically modified to alter (e.g., increase or decrease, for example) a desired activity. In some embodiments, nucleic acid encoding a fusion protein described herein, sometimes are genetically modified to optimize the heterologous polynucleotide sequence encoding the desired activity (e.g., polypeptide or protein, for example). The term "optimize" as used herein can refer to alteration to increase or enhance expression by preferred codon usage. The term optimize can also refer to modifications to the amino acid sequence to increase the activity of a polypeptide or protein, such that the activity exhibits a higher catalytic activity as compared to the "natural" version of the polypeptide or protein.

Nucleotide sequences of interest can be genetically modified using methods known in the art. Mutagenesis techniques are particularly useful for small scale (e.g., 1, 2, 5, 10 or more nucleotides) or large scale (e.g., 50, 100, 150, 200, 500, or more nucleotides) genetic modification. Mutagenesis allows the artisan to alter the genetic information of an organism in a stable manner, either naturally (e.g., isolation using selection and screening) or experimentally by the use of chemicals, radiation or inaccurate DNA replication (e.g., PCR mutagenesis). In some embodiments, genetic modification can be performed by whole scale synthetic synthesis of nucleic acids, using a native nucleotide sequence as the reference sequence, and modifying nucleotides that can result in the desired alteration of activity. Mutagenesis methods sometimes are specific or targeted to specific regions or nucleotides (e.g., site-directed mutagenesis, PCR-based site-directed mutagenesis, and in vitro mutagenesis techniques such as transplacement and in vivo oligonucleotide site-directed mutagenesis, for example). Mutagenesis methods sometimes are non-specific or random with respect to the placement of genetic modifications (e.g., chemical mutagenesis, insertion element (e.g., insertion or transposon elements) and inaccurate PCR based methods, for example).

A native, heterologous or mutagenized polynucleotide can be introduced into a nucleic acid reagent for introduction into a host organism, thereby generating an engineered microorganism. Standard recombinant DNA techniques (restriction enzyme digests, ligation, and the like) can be used by the artisan to combine the mutagenized nucleic acid of interest into a suitable nucleic acid reagent capable of (i) being stably maintained by selection in the host organism, or (ii) being integrating into the genome of the host organism. As noted above, sometimes nucleic acid reagents include two replication origins to allow the same nucleic acid reagent to be manipulated in bacterial before final introduction of the final product into the host organism (e.g., yeast or fungus for example). Standard molecular biology and recombinant DNA methods available to one of skill in the art can be found in Maniatis, T., E. F. Fritsch and J. Sambrook (1982) Molecular Cloning: a Laboratory Manual; Cold Spring Harbor Laboratory, Cold Spring Harbor, N.Y.

Engineered Organisms

An organism selected often is suitable for genetic manipulation and often can be cultured at cell densities useful for industrial production of a target product. In some embodiments, an organism selected sometimes can be a microorganism. A microorganism selected often can be maintained in a fermentation device. The term "organism" refers to a prokaryotic, archaebacterial or eukaryotic organism, or cells there from, visible to the naked eye or using non-microscopic magnification techniques. The term "microorganism" as used herein refers to a prokaryotic, archaebacterial or eukaryotic organisms or cells there from, visible using microscopic magnification techniques. The terms organism and microorganism can be used interchangeably throughout the document.

The term "engineered organism" or "engineered microorganism" as used herein refers to a modified organism or microorganism that includes one or more activities distinct from an activity present in an organism utilized as a starting point (hereafter a "host microorganism"). An engineered microorganism includes a heterologous polynucleotide in some embodiments, and in certain embodiments, an engineered organism has been subjected to selective conditions that alter an activity, or introduce an activity, relative to the host microorganism. Engineered microorganisms can be prepared by altering, introducing or removing nucleotide sequences in the host genome or in stably maintained epigenetic nucleic acid reagents, as noted above. The nucleic acid reagents used to alter, introduce or remove nucleotide sequences in the host genome or epigenetic nucleic acids can be prepared using the methods described herein or available to the artisan. Thus, an engineered microorganism has been altered directly or indirectly by a human being. A host microorganism sometimes is a native microorganism, and at times is an organism that has been engineered to a certain point.

In some embodiments an engineered microorganism is a single cell organism, often capable of dividing and proliferating. A microorganism can include one or more of the following features: aerobe, anaerobe, filamentous, non-filamentous, monoploid, dipoid, auxotrophic and/or non-auxotrophic. In certain embodiments, an engineered microorganism is a prokaryotic microorganism (e.g., bacterium), and in certain embodiments, an engineered microorganism is a non-prokaryotic microorganism. In some embodiments, an engineered microorganism is a eukaryotic microorganism (e.g., yeast, fungi, amoeba, and algae).

A suitable yeast may be selected as a host microorganism, engineered microorganism or source for a heterologous polynucleotide. Yeast include, but are not limited to, *Yarrowia* yeast (e.g., *Y. lipolytica* (formerly classified as *Candida lipolytica*)), *Candida* yeast (e.g., *C. revkaufi, C. pulcherrima, C. tropicalis, C. utilis*), *Rhodotorula* yeast (e.g., *R. glutinus, R. graminis*), *Rhodosporidium* yeast (e.g., *R. toruloides*), *Saccharomyces* yeast (e.g., *S. cerevisiae, S. bayanus, S. pastorianus, S. carlsbergensis*), *Cryptococcus* yeast, *Trichosporon* yeast (e.g., *T. pullans, T. cutaneum*), *Pichia* yeast (e.g., *P. pastoris*) and *Lipomyces* yeast (e.g., *L. starkeyii, L. lipoferus*). In some embodiments, a yeast is a *S. cerevisiae* strain including, but not limited to, YGR240CBY4742 (ATCC accession number 4015893) and BY4742 (ATCC accession number 201389). In some embodiments, a yeast is a *Y. lipolytica* strain that includes, but is not limited to, ATCC20362, ATCC8862, ATCC18944, ATCC20228, ATCC76982 and LGAM S(7)1 strains (Papanikolaou S., and Aggelis G., Bioresour. Technol. 82(1):43-9 (2002)). In certain embodiments, a yeast is a *C. tropicalis* strain that includes, but is not limited to, ATCC20336, ATCC20913, SU-2 (ura3-/ura3-), ATCC20962, H5343 (beta oxidation blocked; U.S. Pat. No. 5,648,247) strains.

A suitable fungus may be selected as a host microorganism, engineered microorganism or source for a heterologous polynucleotide. Non-limiting examples of fungi include, but are not limited to, *Aspergillus* fungi (e.g., *A. parasiticus, A. nidulans*), *Thraustochytrium* fungi, *Schizochytrium* fungi and *Rhizopus* fungi (e.g., *R. arrhizus, R. oryzae, R. nigricans*). In some embodiments, a fungus is an *A. parasiticus* strain that includes, but is not limited to, strain ATCC24690, and in certain embodiments, a fungus is an *A. nidulans* strain that includes, but is not limited to, strain ATCC38163.

A suitable algae may be selected as a host microorganism, engineered microorganism or source for a heterologous polynucleotide. Non-limiting examples of algae include, but are not limited to, microalgae (e.g., phytoplankton, microphytes, Spirulina, *Chlorella, Chondrus, Mastocarpus, Ulva, Alaria, Cyanobacteria* (e.g., blue-green algae) and the like) and macroalgae (e.g., seaweeds, *Porphyra, Palmaria* and the like).

A suitable prokaryote may be selected as a host microorganism, engineered microorganism or source for a heterologous polynucleotide. A Gram negative or Gram positive bacteria may be selected. Examples of bacteria include, but are not limited to, *Bacillus* bacteria (e.g., *B. subtilis, B. megaterium*), *Acinetobacter* bacteria, *Norcardia* baceteria, *Xanthobacter* bacteria, *Escherichia* bacteria (e.g., *E. coli* (e.g., strains DH10B, Stb12, DH5-alpha, DB3, DB3.1), DB4, DB5, JDP682 and ccdA-over (e.g., U.S. application Ser. No. 09/518,188))), *Streptomyces* bacteria, *Erwinia* bacteria, *Klebsiella* bacteria, *Serratia* bacteria (e.g., *S. marcessans*), *Pseudomonas* bacteria (e.g., *P. aeruginosa*), *Salmonella* bacteria (e.g., *S. typhimurium, S. typhi*). Bacteria also include, but are not limited to, photosynthetic bacteria (e.g., green non-sulfur bacteria (e.g., *Choroflexus* bacteria (e.g., *C. aurantiacus*), *Chloronema* bacteria (e.g., *C. gigateum*)), green sulfur bacteria (e.g., *Chlorobium* bacteria (e.g., *C. limicola*), *Pelodictyon* bacteria (e.g., *P. luteolum*), purple sulfur bacteria (e.g., *Chromatium* bacteria (e.g., *C. okenii*)), and purple non-sulfur bacteria (e.g., *Rhodospirillum* bacteria (e.g., *R. rubrum*), *Rhodobacter* bacteria (e.g., *R. sphaeroides, R. capsulatus*), and *Rhodomicrobium* bacteria (e.g., *R. vanellii*)).

Cells from non-microbial organisms can be utilized as a host microorganism, engineered microorganism or source for a heterologous polynucleotide. Examples of such cells, include, but are not limited to, insect cells (e.g., *Drosophila* (e.g., *D. melanogaster*), *Spodoptera* (e.g., *S. frugiperda* Sf9 or Sf21 cells) and *Trichoplusa* (e.g., High-Five cells); nematode cells (e.g., *C. elegans* cells); avian cells; amphibian cells (e.g., *Xenopus laevis* cells); reptilian cells; and mammalian cells (e.g., NIH3T3, 293, CHO, COS, VERO, C127, BHK, Per-C6, Bowes melanoma and HeLa cells).

Microorganisms or cells used as host organisms or source for a heterologous polynucleotide are commercially available. Microorganisms and cells described herein, and other suitable microorganisms and cells are available, for example, from Invitrogen Corporation, (Carlsbad, Calif.), American Type Culture Collection (Manassas, Va.), and Agricultural Research Culture Collection (NRRL; Peoria, Ill.).

Host microorganisms and engineered microorganisms may be provided in a suitable form. For example, such microorganisms may be provided in liquid culture or solid culture (e.g., agar-based medium), which may be a primary culture or may have been passaged (e.g., diluted and cultured) one or more times. Microorganisms also may be provided in frozen form or dry form (e.g., lyophilized). Microorganisms may be provided at a suitable concentration.

Nucleotide sequences having a desired activity can be isolated from cells of a suitable organism using lysis and nucleic acid purification procedures available in Maniatis, T., E. F. Fritsch and J. Sambrook (1982) Molecular Cloning: a Laboratory Manual; Cold Spring Harbor Laboratory, Cold Spring Harbor, N.Y. or with commercially available cell lysis and DNA purification reagents and kits. In some embodiments, nucleic acids used to engineer microorganisms can be provided for conducting methods described herein after processing of the organism containing the nucleic acid. For example, the nucleic acid of interest may be extracted, isolated, purified or amplified from a sample (e.g., from an organism of interest or culture containing a plurality of organisms of interest, like yeast or bacteria for example). The term "isolated" as used herein refers to nucleic acid removed from its original environment (e.g., the natural environment if it is naturally occurring, or a host cell if expressed exogenously), and thus is altered "by the hand of man" from its original environment.

In certain embodiments, an expression construct comprising a nucleic acid encoding a fusion protein produced using methods described herein can be inserted into an organism. In certain embodiments, an organism may include an isolated expression construct, constructed as described herein. In some embodiments, the method can include inserting nucleic acid encoding a fusion protein described herein into genomic DNA of an organism. In certain embodiments, the methods described above can include inserting nucleic acid encoding a fusion protein described herein into a yeast artificial chromosome.

Nucleic acid reagents can be introduced into microorganisms using various techniques. Non-limiting examples of methods used to introduce heterologous nucleic acids into various organisms include: transformation, transfection, transduction, electroporation, ultrasound-mediated transformation, particle bombardment and the like. In some instances the addition of carrier molecules (e.g., bis-benzimdazolyl compounds, for example, see U.S. Pat. No. 5,595,899) can increase the uptake of DNA in cells typically though to be difficult to transform by conventional methods. Conventional methods of transformation are known in the art and can be found in Maniatis, T., E. F. Fritsch and J. Sambrook (1982) Molecular Cloning: a Laboratory Manual; Cold Spring Harbor Laboratory, Cold Spring Harbor, N.Y.

Kits

Kits include one or more containers, which contain one or more of the compositions and/or components described herein. A kit includes one or more of the components in one or more separate containers, packets, tubes, vials, microtiter plates and the like, or the components may be combined in various combinations in such containers. A kit may include a nucleic acid reagent that encodes a fusion protein described herein, or reagents suitable for generating and expressing fusion proteins described herein.

A kit can include one or more reagents described herein in a suitable combination. A kit may include two, three, four, five or more reagents described herein. For example, a kit can include (i) one or more linker sequences for functionally joining a selected activity and association domain, (ii) a nucleic acid reagent suitable for expressing an activity domain linked to an association domain via one or more linkers (iii) cell-free expression system suitable for expression of a fusion protein from one or more polynucleotides encoding an association and activity domain joined by a linker sequence, (iv) cells capable of replicating and/or for expression of a fusion protein from a nucleic acid reagent comprising a polynucleotide encoding a fusion protein, (v) reagents suitable for conjugating polypeptides comprising association and/or activity domains to linker peptides, and the like, and other combinations of reagents described herein.

A kit sometimes is utilized in conjunction with a method described herein, and sometimes includes instructions for performing one or more methods described herein and/or a description of one or more compositions or reagents described herein. Instructions and/or descriptions may be in printed form and may be included in a kit insert. A kit also may include a written description of an internet location that provides such instructions or descriptions.

EXAMPLES

The examples set forth below illustrate certain embodiments and do not limit the disclosed technology.

Example 1

Selection of a Nucleic Acid Association Domain (e.g., First Domain)

A RNA recognition motif (RRM) nucleic acid association domain can be selected from available nucleic acid databases. For this example the NCBI Nucleotide database is used. The search term entered can be "pumilio RNA binding motif". The mRNA tab is chosen, which indicates there are 29 available sequences. Accession number NM001090603 is selected. Accession number NM001090603 corresponds to a pumilio 1 transcript variant from Xenopus laevis. The amino acid sequence and nucleotide sequence information are presented below.

Amino Acid Sequence:
MAFPLKDDLGRAKDCWGCPSDTPALSTCSNADIFRRINAMLDNSLDFTGV
CTTPNTKGKCEHLQDYQDTEGPAASRMLFSTSHEPLPRGLPDTNDLCLGL
QSLSLTGWDRPWSTQDSEAGGHSSTPTAAQSVFSMLNSPMGKPSPLGFL
TFDPIGSDLMEKYPTPLLRSSRLDSRSILDSRSSSPSDSDTSGFSSGSDH
LSDLISSLRISPPLHFLPLGGGVSRDPLKLGIGSRLDQDHAALAAATVS
PLGITKGWPSTSVWPSWDLLDSAEDPFSIEREARLHRQAAAVNEATCTWS
GQLPPRNYKNPVYSCKVFLGGVPWDITETGLINTFRVFGALSVEWPGKD
GKHPRCPPKGNMPKGYVYLVFESEKSVRALLQACSQDLLSQDGLSEHYF
KMSSRRMACKEVQVIPWVLADSNFVRSPSQRLDPSKTVFVGALHGMLNA
EALASIMNDLFGGVVYAGIDTDKHKYPIGSGRVTFNNQRSYLKAVSAAFV
EIKTAKFTKKVQIDPYLEDSVCQVCNAQPGPFFCRDQVCFKYFCRSCWH
WQHSMEILRHHRPLMRNQKSRDSS (SEQ ID NO: 42)

Nucleotide Sequence:
attccgattg cattgaaatt caatttggca ttaagtttta attacccag tctgaccagg
agcctgcgcc atggccttcc cactgaaaga tgatttaggg agagccaaag attgctgggg
ctgcccatcc gacacccag cccttctac ctgcagcaat gctgatattt cagacgaat
aaacgccatg ctggacaact ctctggattt cactggtgtt tgcaccaccc caaacacaaa
gggcaaatgt gaacaccttc aagactacca agatacagag ggacctgcag ctagcagaat
gctgttttcc acttcacatg aacctcttcc tcgcggcctt ccagatacca atgacttgtg
ccttggtctt cagtctctca gtcttacagg gtgggacaga ccctggagca ctcaggactc
agaagctggt ggacattcaa gtactccaac agctgctcag tctgtcttta gcatgctgaa
cagccccatg gggaagccaa gcccttggg ctttctgaca tttgatccaa ttggttcaga
cctcatggag aagtatccta ctcctttgct gcgtagctct cgattggaca gccgctctat
tttggattct cgctccagca gcccttctga ctctgacact agtggattca gctctggatc
agaccacctt tcagacctaa tttcaagtct tcgcatctct cctccgctgc atttcctccc
acttggaggg ggagtgtcac gggacccgtt gaagctaggt attggctcaa ggctagacca
ggaccatgca gccttggcgg cagcaactgt ctctccactt ggcataacaa agggatggcc
cagtacttca gtctggcctt cctgggatct gctggattct gcagaggacc catttagcat
tgagcgagag gcacgcctac acagacaggc tgcagctgtg aatgaagcaa cctgcacctg
gagtgggcag ctgccccta gaaactacaa aaatcctgtg tattcctgca aagtctttct
cggtggtgtc ccctgggaca taacagaaac tggacttatc aacacgttcc gtgtatttgg
agcacttagt gttgagtggc ctggtaagga tggcaagcat ccccgctgcc ctcccaaagg
taatatgccc aaaggttatg tttatctggt atttgaatca gagaagtcag ttcgtgcttt
gcttcaggcg tgctctcagg acctactaag ccaagatggg ctgagtgaac actacttcaa
aatgtccagt cgcaggatgg cctgcaagga ggtgcaggtc attccttggg tgcttgcaga
cagcaacttt gtgcgtagtc catcacaacg gctggatccc agtaagactg tatttgtggg
agctctacat ggcatgctaa atgctgaagc tttggcttcg atcatgaatg atctgtttgg
tggcgtagtc tatgctggca ttgatactga taagcacaaa tatccaatcg gtccggtcg
tgtgaccttc aataaccagc gcagttacct gaaagctgtg agtgctgctt ttgtggaaat
aaaaactgcc aagtttacaa aaaggttca aattgatccg tatttggaag actctgtttg
ccaggtgtgc aatgctcagc ctgggccatt cttctgcaga gaccaggttt gctttaagta
tttctgccgt tcctgttggc actgcagca ctctatggaa atcctgcgcc accaccgccc
tctcatgcgt aatcagaaaa gtcgtgactc cagctaaaga cattggaaca acattggtcc
aaaaatctga cacaactgga tatgttgggc taacaagagt gttcagaatt ttctccctct
agcactggaa gcactagttt tttttttttt tattccaggg atagatcagc aatcagtgga -continued

```
ttgtggggag aatgtcacta ttttttttgca cttgctgtac cttgtggtag ttttctcaca ctagtgcaca cttgagattt gccaggtttt ttgcttttct tttaaaaaaa aaaaattgag aggatatttc cttctcagga cttaattgca gttcccagac tgggcctaaa caacaattgc tgaaagtaag caatgttcat ggccttgttt tcttaaggtt tatggctaat gatgcctctg cttttggtta acttttttt tttttttatt acaggcactt cttttacatt ccttgcaata ttgctggtga tgatgcaaat tacattaatc ttcccatgtt ttgctgttgc catacagtgc cttccaattt atttgatgtc ccatctgaac tacataaact agtttagctg acatttttac tgtaacaaca atagcagaat ttgctcttta aaccaaatca tatttcatat ttttacccct gtggatttt accagttcct ttttacactc ttaaagacgt tttttaagtc cattatattt tgttttcttt tcctggcagc ttttaacatt attgcaaagt tcagtttctg ggagctgctg gttaagaaaa taaacctaca taaattcctt gtacaacaga gtttataacc aaaaggacag acttaaggcc ttgactgaac cagattatga cagtgtgtgt gtatagtttt aaggaaattt gttgcacttt tttaatttgc acttaagggg atggtagagt ttttaatcac tttctgtttg tatttggctg gacaaaaaag ggctgtgata tgtcttgaga atggggtaga ggcaagagat ggcacaaac ctttctcctg gagggaataa gtgcccatgc tctgttttc ttcttttttt ttgtggaaat aactgactta tgcaaactgt tgcaggcctt tacaattttg tgtccttaat ttttatttat agccccctt aaaattgtaa gctctgtgcc aaagacccca gtttctgta ttccctctta tccagaacat gctgagctaa ttctacttcc tagctgccct aagcagggta tatctgtgaa gctgtgtgta aagtctctac ctcattgtag ttatgcaagc agaagatgca cttaatctat ggatgtggtg tagttttgtt tgtttttctt tgtttttttt ggcacaaaat aaacacgttg aagcaga (SEQ ID NO: 43)
```

Information provided in the nucleotide sequence listing indicates that the two RNA recognition motifs (RRM1 and RRM2) are located in nucleotide positions 1010-1261 and 1364-1603, respectively. Oligonucleotides corresponding to these entire regions can be synthesized, or primers suitable for PCR amplification of the desired nucleotides can be synthesized.

Example 2

Selection of Ribonuclease III Activity Domain (e.g., Second Domain)

A ribonuclease III activity domain is chosen to be functionally combined with the RNA recognition motif to provide a novel RNA cleaving fusion protein. A ribonuclease III activity (e.g., cleavage) domain can be selected from available nucleic acid databases. For this example the NCBI Gene database is used, and the search term entered is "ribonuclease cleavage domain". The database returned about 90 total entries. One selected is RNC1, chloroplast ribonuclease III domain protein [*Zea mays*]. The "nucleotide" link to the right of the worldwide web page is selected. Five nucleotide sequences are displayed, and Accession number NM001112585 is selected, which corresponds to the cDNA sequence of the gene. The amino acid and nucleotide sequence of the gene are displayed below.

```
Amino Acid Sequence:
MGPPAMAFQALTLTPLPFSLHSSSRRVRVLAVAADQTPPPAPPSE

PANSPSRLLRELAQRKKAVSPKKKHPPRRFILKPPLDDERLTRRFLSSPQ

LSLKALPLLSSCLPSAPLSTADRTWMDEYLLEAKQALGYPLAPSETLGEG

DDCPARHFDVLFYLAFQHLDPSSERTRMRHVRNGHSRLWFLGQYVLELA

FCEFFLQRYPRESPGPMRERVFALIGKKVLPRWLKAASLHNLVFPYDDLD

KMIRKDREPPSKAVFWAIFGAIYLCFGMPEVYRVLFEAFGMDPDDESCQP

KLRRQLEDVDYVSVEFEKRQLTWQDVAAYRPPPDALFAHPRLFRACVPP

GMHRFRGNIWDFDSRPKVMTTLGYPLPMNDRIPEITEARNIELGLGLQLC

FLHPSKHKFEHPRFCYERLEYVGQKIQDLVMAERLLMKHLDAPGRWLAE

KHRRTLMNKYCGRYLRDKHLQHYIIYGETVQDRFEHNRRLRNPSTTSVQ

QALHGLAYCVYGKPDVRRLMFEVFDFEQVQPKAV (SEQ ID NO: 44)
```

```
Nucleotide Sequence (from mRNA):
cataattctc gtctgcttat ccgctccctt ctctccctca acttcagcaa gttcccgca aaaccgcagc cggaggtcgc cggtcgccac caccaatggg gccacccgcc atggcgttcc
```

```
                          -continued
aagccctcac cctcacgcca ctccccttct cactccacag ctcgagccgc cgcgtccgcg tgcttgccgt tgcggccgac cagactcctc cgcccgcccc cccttcggag ccggcgaaca gccctagccg cctccttcgc gagctcgcgc agcggaagaa ggccgtatcc cctaagaaga agcatccgcc gcgtcgcttc atcctgaagc cacctctcga tgacgagcgc cttacccggc ggttcctcag cagcccgcag ctgtcgctca aggcgctccc gctgctctct tcctgcctcc cctccgcgcc gctctccacc gccgacagga cctggatgga cgagtacctc ctcgaggcca agcaggcgct cgggtacccg ctcgcgccct cggagacgct cggcgaaggc gatgactgcc ccgcgcgtca tttcgatgtg ctgttctacc tcgcgttcca gcatctggac ccctctagcg agcgcacgcg gatgcggcac gtacggaacg gccactccag gctctggttc ctgggtcagt acgttctgga gctcgcgttc tgcgagttct tcttgcagag gtaccccagg gagtcacctg ggccgatgag ggagcgggtg ttcgctctaa ttgggaagaa agtgttgccc cgatggctca aggcggccag cctgcacaat ttggtcttcc cctatgatga tttggataag atgatacgaa aggaccggga gccaccgtcc aaggctgtat tctgggcaat atttggagct atatatttgt gctttggaat gcctgaagtc tatcgtgtcc tttttgaggc atttgggatg gatccagatg atgagagctg tcagccaaaa ttgcgtcgtc aactagagga tgttgattat gtttcagtgg agttcgaaaa gaggcagctc acttggcagg atgttgctgc ctacaggccg ccaccggatg ctcttttgc tcatcctagg cttttccgag cttgtgtgcc accaggcatg catcggttca gaggaaatat ttgggatttt gacagtagac ccaaggtcat gactaccta ggatatccct tgcccatgaa tgacagaatt ccagaaatca cagaagcaag gaatatagag cttggacttg gtcttcagct gtgttttttg cacccatcaa aacataagtt tgagcatcca agattttgtt atgagcggct tgaatacgtc ggccagaaaa ttcaggatct agtaatggca gagaggctac tcatgaaaca cctcgatgca ccaggcaggt ggctggcgga gaagcatcgg aggacgttga tgaacaagta ttgtggacgg tacctgcggg acaagcacct gcagcactac attatctacg gggagacagt gcaagacaga ttcgaacaca atcgacgtct aaggaatcct tcaacgacct ctgtccagca agcgctacat gggcttgcat actgtgtgta tggcaaacct gacgtgcggc gtttgatgtt cgaggtgttt gacttcgaac aggtccagcc taaagcagtc tgaggatctt ctccattggt accgatgcta gagttgctga atgctgacca acaagacccc aatggcagtg gtacaaatgc tgtagattct tgaagtcgtc cattcgacag gagatctttc gattytgaag cctgaagccc tgaaccctga gctgggacag ctgattagcc actgggtcct gtctctcctg aaaccgtcac tgttccaacc ttcttgtccg tcggaaatgg tagactagtg atgatgtgga tcggaggctg ctgttgtttg aacttacaat tttgataatt cgttgtaaat tcctgtttgg gcagaaacgc aaatagcagc agcatggcag attcatttcc tatcagaatt gtagtccgta atcgagaagc agtaagatga ataatataaa gatattcatt caaaaaaaaa aaaaaaaaa aaaaaaa (SEQ ID NO: 45)
```

The search term used to select the activity domain includes the term "cleavage domain", and therefore it is expected that the sequence identified is the complete nucleotide sequence of the catalytic domain of ribonuclease III. This feature can be verified by nucleotide sequence alignment with the sequence of a known ribonuclease III catalytic domain. An oligonucleotide corresponding to the entire region can be synthesized, or primers suitable for PCR amplification of the desired nucleotides can be synthesized.

Example 3

Joining First and Second Domains

First and second domains are joined via a linker sequence. To allow sufficient separation of the association and activity domains the following two linker sequences are used, GSGGGGSAAGASAS (SEQ ID NO: 1), STSGGSG-GTGGS (SEQ ID NO: 2) giving 26 amino acids of separation, or 78 nucleic acids of separation. In some embodiments, the linker length is selected to allow the activity to occur at a desired location. In certain embodiments, the linker length is selected to reduce or eliminate steric interference between domains. The nucleotide sequence of the aforementioned linker sequences can be deduced by the artisan, manually or using available software tools.

A linker can be synthesized separately and joined via ligation or PCR, or can be synthesized as one oligonucleotide. Using sticky ends, polynucleotides encoding the first domain and second domain can be assembled with the linker, using PCR or ligation of the overhanging ends. The artisan also can synthesize a single oligonucleotide corresponding to the nucleotide sequences chosen for the first, domain, linker sequences, and second domain. The artisan can also assemble peptides or proteins via conjugation methods described herein. Such methods can be used to generate a fusion protein with a RRM1 and/or RRM2 RNA association domain and a ribonuclease III activity domain. A nucleic acid encoding a fusion protein can be inserted into an expression construct and/or operably linked to a transcription promoter for use in a cell-free system, for example.

Example 4

Fusion Protein Expression

A nucleic acid encoding a fusion protein often is transcribed for expression. To allow expression, a nucleic acid encoding a fusion protein is operably linked to a transcription promoter. In some embodiments, a transcription promoter sequence is added to a nucleic acid encoding a fusion protein to allow expression in a cell free system. PCR amplification can be used to replicate the sequences for expression in a cell-free system. In certain embodiments, a nucleic acid encoding a fusion protein is inserted into a nucleic acid reagent. The nucleic acid reagent is capable of replication of the nucleic acid sequence and expression of a fusion protein in a host organism or cell-free system.

Example 5

Assay of Activity

An activity of an expressed fusion protein can be. Functionality of a ribonuclease activity can be assayed by detecting cleaved RNA by gel electrophoresis. Functionality of the association domain can be determined by primer extension sequencing of cleaved RNA or by competitive inhibition of the binding reaction. Saturation of a reaction with a sequence complementary to an association domain recognition sequence could reduce or inhibit cleavage of the target RNA by the activity domain. Additional methods of assaying an activity of a first and second domain can be utilized. Non-limiting examples for determining functionality of an activity domain include detection of cleavage products, detection of loss or gain of function of a gene (or protein encoded by the gene) targeted by a fusion protein (detection of a protein that is expressed at higher or lower levels or during times of the cell cycle the protein is not normally expressed, size discrimination of a cleavage product and the like, for example), detection of knock-ins or knock-outs and the like. The assay selected is based on the type of activity chosen for a second domain.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

The present disclosure is not to be limited in terms of particular embodiments described in this disclosure, which are illustrations of various aspects. Many modifications and variations can be made without departing from the spirit and scope of the disclosure, as will be apparent to those skilled in the art. Functionally equivalent methods and apparatuses within the scope of the disclosure, in addition to those enumerated herein, will be apparent to those skilled in the art from the foregoing descriptions. Such modifications and variations fall within the scope of the appended claims. The present disclosure is to be limited only by the terms of claims (e.g., the claims appended hereto) along with the full scope of equivalents to which such claims are entitled. It is to be understood that this disclosure is not limited to particular methods, reagents, compounds compositions or biological systems, which can, of course, vary. It is also to be understood that terminology used herein is for the purpose of describing particular embodiments only, and is not necessarily limiting.

With respect to the use of substantially any plural and/or singular terms herein, those having skill in the art can translate from the plural to the singular and/or from the singular to the plural as is appropriate to the context and/or application. Various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). It will be further understood by those within the art that virtually any disjunctive word and/or phrase presenting two or more alternative terms, whether in the description, aims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

Thus, it should be understood that although the present technology has been specifically disclosed by representative embodiments and optional features, modification and variation of the concepts herein disclosed may be resorted to by those skilled in the art, and such modifications and variations are considered within the scope of this technology. As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not limiting, with the true scope and spirit of certain embodiments indicated by the following claims.

What is claimed is:

1. A fusion protein comprising two heterologous polypeptide domains connected by a linker, wherein a first polypeptide domain is configured to associate with a nucleic acid, and a second polypeptide domain has RNA cleavage activity;

wherein the first polypeptide domain is:

SEQ ID NO: 7 (pumilio); and wherein the second polypeptide domain is a dicer endoribonuclease, wherein the dicer endoribonuclease comprises two RNase III domains and a PAZ domain, and wherein the dicer endoribonuclease cleaves double-stranded RNA and pre-microRNA.

2. A isolated cell comprising the fusion protein of claim 1.

3. A cell-free system comprising the fusion protein of claim 1.

4. An in vitro method for modifying a target nucleic acid, comprising contacting the target nucleic acid with the fusion protein of claim 1 under modification conditions, whereby the target nucleic acid is modified by the fusion protein.

* * * * *

UNITED STATES PATENT AND TRADEMARK OFFICE
CERTIFICATE OF CORRECTION

PATENT NO. : 8,889,394 B2
APPLICATION NO. : 12/554949
DATED : November 18, 2014
INVENTOR(S) : Chalasani Page 1 of 2

It is certified that error appears in the above-identified patent and that said Letters Patent is hereby corrected as shown below:

On the Title Page, in Item (56), under "OTHER PUBLICATIONS", in Column 2, Line 1, delete "(The" and insert -- The --, therefor.

On the Title Page, in Item (56), under "OTHER PUBLICATIONS", in Column 2, Line 1, delete "Feburary" and insert -- February --, therefor.

On the Title Page, in Item (56), under "OTHER PUBLICATIONS", in Column 2, Line 3, delete "(Biochemistry," and insert -- Biochemistry, --, therefor.

On Title Page 2, in Item (56), under "OTHER PUBLICATIONS", in Column 1, Line 16, delete "condons,"" and insert -- codons," --, therefor.

In the Specification

In Column 5, Lines 33-34, delete "a organism" and insert -- an organism --, therefor.

In Column 6, Line 63, delete "first" and insert -- fist --, therefor.

In Column 10, Line 51, delete "al," and insert -- al., --, therefor.

In Column 12, Line 25, delete "and or" and insert -- and/or --, therefor.

In Column 21, Line 66, delete "glycolsylase" and insert -- glycosylase --, therefor.

In Column 32, Line 22, delete "first" and insert -- fist --, therefor.

In Column 40, Line 15, delete "siRNAs" and insert -- siRNA's --, therefor.

Signed and Sealed this
Fifteenth Day of September, 2015

Michelle K. Lee
*Director of the United States Patent and Trademark Office*

In Column 45, Lines 22-23, delete "Hind III," and insert -- Hind II, --, therefor.

In Column 45, Line 27, delete "glycolsylase" and insert -- glycosylase --, therefor.

In Column 50, Line 59, delete "(ETV);" and insert -- (TEV); --, therefor.

In Column 51, Line 52, delete "(sRNA)," and insert -- (siRNA), --, therefor.

In Column 53, Line 61, delete "subtilisi" and insert -- subtilis --, therefor.

In Column 53, Line 65, delete "precollagen" and insert -- procollagen --, therefor.

In Column 60, Line 26, delete "herein" and insert -- herein. --, therefor.

In Column 62, Line 5, delete "dipoid," and insert -- diploid, --, therefor.

In Column 62, Line 60, delete "Norcardia baceteria," and insert -- Nocardia bacteria, --, therefor.

In Column 63, Line 15, delete "Trichoplusa" and insert -- Trichoplusia, --, therefor.

In the Claims

In Column 144, Line 10, in Claim 2, delete "A isolated" and insert -- An isolated --, therefor.

SEQUENCE LISTING

```
<160> NUMBER OF SEQ ID NOS: 45

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Ser Gly Gly Gly Gly Ser Ala Ala Gly Ala Ser Ala Ser
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Thr Ser Gly Gly Ser Gly Gly Thr Gly Gly Ser
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Thr Gly Gly Thr Gly Gly Ser Gly Gly Thr Gly
```

<210> SEQ ID NO 4
<211> LENGTH: 77
<212> TYPE: PRT
<213> ORGANISM: Bacillus caldolyticus

<400> SEQUENCE: 4

| Met | Ile | Asn | Glu | Ile | Glu | Ile | Lys | Arg | Lys | Phe | Gly | Arg | Thr | Leu | Lys |
|---|---|---|---|---|---|---|---|---|---|---|---|---|---|---|---|
| 1 | | | | 5 | | | | | 10 | | | | | 15 | |

| Lys | Ile | Arg | Thr | Gln | Lys | Gly | Val | Ser | Gln | Glu | Glu | Leu | Ala | Asp | Leu |
|---|---|---|---|---|---|---|---|---|---|---|---|---|---|---|---|
| | | | 20 | | | | | 25 | | | | | 30 | | |

| Ala | Gly | Leu | His | Arg | Thr | Tyr | Ile | Ser | Glu | Val | Glu | Arg | Gly | Asp | Arg |
|---|---|---|---|---|---|---|---|---|---|---|---|---|---|---|---|
| | | 35 | | | | | 40 | | | | | 45 | | | |

| Asn | Ile | Ser | Leu | Ile | Asn | Ile | His | Lys | Ile | Cys | Ala | Ala | Leu | Asp | Ile |
|---|---|---|---|---|---|---|---|---|---|---|---|---|---|---|---|
| 50 | | | | | 55 | | | | | 60 | | | | | |

| Pro | Ala | Ser | Thr | Phe | Phe | Arg | Lys | Met | Glu | Glu | Glu | Asn |
|---|---|---|---|---|---|---|---|---|---|---|---|---|
| 65 | | | | | 70 | | | | | 75 | | |

<210> SEQ ID NO 5
<211> LENGTH: 281
<212> TYPE: PRT
<213> ORGANISM: Saccharomyces cerevisiae

<400> SEQUENCE: 5

| Met | Ser | Glu | Tyr | Gln | Pro | Ser | Leu | Phe | Ala | Leu | Asn | Pro | Met | Gly | Phe |
|---|---|---|---|---|---|---|---|---|---|---|---|---|---|---|---|
| 1 | | | | 5 | | | | | 10 | | | | | 15 | |

| Ser | Pro | Leu | Asp | Gly | Ser | Lys | Ser | Thr | Asn | Glu | Asn | Val | Ser | Ala | Ser |
|---|---|---|---|---|---|---|---|---|---|---|---|---|---|---|---|
| | | | 20 | | | | | 25 | | | | | 30 | | |

| Thr | Ser | Thr | Ala | Lys | Pro | Met | Val | Gly | Gln | Leu | Ile | Phe | Asp | Lys | Phe |
|---|---|---|---|---|---|---|---|---|---|---|---|---|---|---|---|
| | | 35 | | | | | 40 | | | | | 45 | | | |

| Ile | Lys | Thr | Glu | Glu | Asp | Pro | Ile | Ile | Lys | Gln | Asp | Thr | Pro | Ser | Asn |
|---|---|---|---|---|---|---|---|---|---|---|---|---|---|---|---|
| | 50 | | | | | 55 | | | | | 60 | | | | |

| Leu | Asp | Phe | Asp | Phe | Ala | Leu | Pro | Gln | Thr | Ala | Thr | Ala | Pro | Asp | Ala |
|---|---|---|---|---|---|---|---|---|---|---|---|---|---|---|---|
| 65 | | | | | 70 | | | | | 75 | | | | | 80 |

| Lys | Thr | Val | Leu | Pro | Ile | Pro | Glu | Leu | Asp | Asp | Ala | Val | Val | Glu | Ser |
|---|---|---|---|---|---|---|---|---|---|---|---|---|---|---|---|
| | | | | 85 | | | | | 90 | | | | | 95 | |

| Phe | Phe | Ser | Ser | Ser | Thr | Asp | Ser | Thr | Pro | Met | Phe | Glu | Tyr | Glu | Asn |
|---|---|---|---|---|---|---|---|---|---|---|---|---|---|---|---|
| | | | 100 | | | | | 105 | | | | | 110 | | |

| Leu | Glu | Asp | Asn | Ser | Lys | Glu | Trp | Thr | Ser | Leu | Phe | Asp | Asn | Asp | Ile |
|---|---|---|---|---|---|---|---|---|---|---|---|---|---|---|---|
| | | 115 | | | | | 120 | | | | | 125 | | | |

| Pro | Val | Thr | Thr | Asp | Asp | Val | Ser | Leu | Ala | Asp | Lys | Ala | Ile | Glu | Ser |
|---|---|---|---|---|---|---|---|---|---|---|---|---|---|---|---|
| | 130 | | | | | 135 | | | | | 140 | | | | |

| Thr | Glu | Glu | Val | Ser | Leu | Val | Pro | Ser | Asn | Leu | Glu | Val | Ser | Thr | Thr |
|---|---|---|---|---|---|---|---|---|---|---|---|---|---|---|---|
| 145 | | | | | 150 | | | | | 155 | | | | | 160 |

| Ser | Phe | Leu | Pro | Thr | Pro | Val | Leu | Glu | Asp | Ala | Lys | Leu | Thr | Gln | Thr |
|---|---|---|---|---|---|---|---|---|---|---|---|---|---|---|---|
| | | | | 165 | | | | | 170 | | | | | 175 | |

| Arg | Lys | Val | Lys | Lys | Pro | Asn | Ser | Val | Val | Lys | Ser | His | His | Val |
|---|---|---|---|---|---|---|---|---|---|---|---|---|---|---|
| | | | 180 | | | | | 185 | | | | | 190 | |

| Gly | Lys | Asp | Asp | Glu | Ser | Arg | Leu | Asp | His | Leu | Gly | Val | Val | Ala | Tyr |
|---|---|---|---|---|---|---|---|---|---|---|---|---|---|---|---|
| | | 195 | | | | | 200 | | | | | 205 | | | |

| Asn | Arg | Lys | Gln | Arg | Ser | Ile | Pro | Leu | Ser | Pro | Ile | Val | Pro | Glu | Ser |
|---|---|---|---|---|---|---|---|---|---|---|---|---|---|---|---|
| | 210 | | | | | 215 | | | | | 220 | | | | |

| Ser | Asp | Pro | Ala | Ala | Leu | Lys | Arg | Ala | Arg | Asn | Thr | Glu | Ala | Ala | Arg |
|---|---|---|---|---|---|---|---|---|---|---|---|---|---|---|---|
| 225 | | | | | 230 | | | | | 235 | | | | | 240 |

| Arg | Ser | Arg | Ala | Arg | Lys | Leu | Gln | Arg | Met | Lys | Gln | Leu | Glu | Asp | Lys |
|---|---|---|---|---|---|---|---|---|---|---|---|---|---|---|---|

```
                    245                 250                 255
Val Glu Glu Leu Leu Ser Lys Asn Tyr His Leu Glu Asn Glu Val Ala
            260                 265                 270
Arg Leu Lys Lys Leu Val Gly Glu Arg
            275                 280

<210> SEQ ID NO 6
<211> LENGTH: 1824
<212> TYPE: DNA
<213> ORGANISM: Saccharomyces cerevisiae

<400> SEQUENCE: 6
atcttcgggg atataaagtg catgagcata catcttgaaa aaaaagatg  aaaaatttcc      60 gactttaaat acggaagata aatactccaa ccttttttc  caattccgaa attttagtct     120
tctttaaaga agtttcggct cgctgtctta ccttttaaaa tcttctactt cttgacagta    180
cttatcttct tatataatag atatacaaaa caaaacaaaa caaaaactca  caacacaggt     240
tactctcccc cctaaattca aatttttttt gcccatcagt ttcactagcg aattatacaa     300
ctcaccagcc acacagctca ctcatctact tcgcaatcaa acaaaatat  tttattttag     360 ttcagtttat taagttatta tcagtatcgt attaaaaaat taaagatcat tgaaaaatgg     420
cttgctaaac cgattatatt ttgttttttaa agtagattat tattagaaaa ttattaagag     480
aattatgtgt taaatttatt gaaagagaaa atttattttc ccttattaat taaagtcctt     540
tacttttttt gaaaactgtc agttttttga agagttattt gttttgttac caattgctat     600
catgtacccg tagaatttta ttcaagatgt ttccgtaacg ttacctttc  tgtcaaatta     660 tccaggttta ctcgccaata aaaatttccc tatactatca ttaattaaat cattattatt     720
actaaagttt tgtttaccaa tttgtctgct caagaaaata aattaaatac aaataaaatg     780
tccgaatatc agccaagttt atttgcttta aatccaatgg gtttctcacc attggatggt     840
tctaaatcaa ccaacgaaaa tgtatctgct tccacttcta ctgccaaacc aatggttggc     900
caattgattt ttgataaatt catcaagact gaagaggatc caattatcaa acaggatacc     960
ccttcgaacc ttgattttga ttttgctctt ccacaaacgg caactgcacc tgatgccaag    1020
accgttttgc caattccgga gctagatgac gctgtagtgg aatctttctt ttcgtcaagc    1080
actgattcaa ctccaatgtt tgagtatgaa aacctagaag acaactctaa agaatggaca    1140
tccttgtttg acaatgacat tccagttacc actgacgatg tttcattggc tgataaggca    1200
attgaatcca ctgaagaagt ttctctggta ccatccaatc tggaagtctc gacaacttca    1260
ttcttaccca ctcctgttct agaagatgct aaactgactc aaacaagaaa ggttaagaaa    1320
ccaaattcag tcgttaagaa gtcacatcat gttggaaagg atgacgaatc gagactggat    1380
catctaggtg ttgttgctta caaccgcaaa cagcgttcga ttccactttc tccaattgtg    1440
cccgaatcca gtgatcctgc tgctctaaaa cgtgctagaa acactgaagc cgccaggcgt    1500
tctcgtgcga gaaagttgca aagaatgaaa caacttgaag acaaggttga agaattgctt    1560
tcgaaaaatt atcacttgga aaatgaggtt gccagattaa agaaattagt tggcgaacgc    1620
tgatttcatt tacctttat  tttatatttt ttatttcatt ctcgtgtata acgaaataga    1680
tacattcact tagataagaa tttaatcttt tttatgccaa ttttcttaag tagaattta     1740 caccacgcat ttataatctg ccgtatgttc tggtatttac tggttaggaa tagataaaaa    1800
aaacactcac gatgggggtc gaac                                             1824
```

<210> SEQ ID NO 7
<211> LENGTH: 1533
<212> TYPE: PRT
<213> ORGANISM: Drosophila melanogaster

<400> SEQUENCE: 7

```
Met Lys Phe Leu Gly Gly Asn Asp Asp Arg Asn Gly Arg Gly Gly Val
1               5                   10                  15

Gly Val Gly Thr Asp Ala Ile Val Gly Ser Arg Gly Val Ser Gln
            20                  25                  30

Asp Ala Asp Ala Ala Gly Ala Ala Ala Ala Ala Val Gly Tyr
        35                  40                  45

Val Phe Gln Gln Arg Pro Ser Pro Gly Gly Val Gly Val Gly
    50                  55                  60

Gly Val Gly Gly Val Pro Gly Val Gly Ala Val Gly Ser Thr Leu
65                  70                  75                  80

His Glu Ala Ala Ala Glu Tyr Ala Ala His Phe Ala Gln Lys Gln
                85                  90                  95

Gln Gln Thr Arg Trp Ala Cys Gly Asp Asp Gly His Gly Ile Asp Asn
            100                 105                 110

Pro Asp Lys Trp Lys Tyr Asn Pro Pro Met Asn Pro Ala Asn Ala Ala
            115                 120                 125

Pro Gly Gly Pro Pro Gly Asn Gly Ser Asn Gly Gly Pro Gly Ala Ile
        130                 135                 140

Gly Thr Ile Gly Met Gly Ser Gly Leu Gly Gly Gly Gly Gly Gly
145                 150                 155                 160

Ala Gly Gly Gly Asn Asn Gly Gly Ser Gly Thr Asn Gly Gly Leu His
                165                 170                 175

His Gln Ser Met Ala Ala Ala Ala Asn Met Ala Ala Met Gln Gln
            180                 185                 190

Ala Ala Ala Leu Ala Lys His Asn His Met Ile Ser Gln Ala Ala Ala
        195                 200                 205

Ala Val Ala Ala Gln Gln Gln His Gln His Pro His Gln Gln His Pro
    210                 215                 220

Gln Gln Gln Gln Gln Gln Gln Ala Gln Asn Gln Gly His Pro His
225                 230                 235                 240

His Leu Met Gly Gly Gly Asn Gly Leu Gly Asn Gly Asn Gly Leu Gly
                245                 250                 255

Ile Gln His Pro Gly Gln Gln Gln Gln Gln Gln Gln Gln Gln Gln
            260                 265                 270

Gln Gln His Pro Gly Gln Tyr Asn Ala Asn Leu Leu Asn His Ala Ala
        275                 280                 285

Ala Leu Gly His Met Ser Ser Tyr Ala Gln Ser Gly Gly Ser Met Tyr
    290                 295                 300

Asp His His Gly Gly Ala Met His Pro Gly Met Asn Gly Gly Met Pro
305                 310                 315                 320

Lys Gln Gln Pro Leu Gly Pro Pro Gly Ala Gly Gly Pro Gln Asp Tyr
                325                 330                 335

Val Tyr Met Gly Gly Gln Thr Thr Val Pro Met Gly Ala Ala Met Met
            340                 345                 350

Pro Pro Gln Asn Gln Tyr Met Asn Ser Ala Ala Val Ala Ala Ala Asn
        355                 360                 365

Arg Asn Ala Ala Ile Thr Thr Ser Thr Ala Lys Lys Leu Trp Glu Lys
    370                 375                 380
```

-continued

```
Ser Asp Gly Lys Gly Val Ser Ser Thr Pro Gly Gly Pro Leu His
385                 390                 395                 400

Pro Leu Gln Ile Pro Gly Ile Gly Asp Pro Ser Ser Val Trp Lys Asp
            405                 410                 415

His Thr Trp Ser Thr Gln Gly Glu Asn Ile Leu Val Pro Pro Pro Ser
        420                 425                 430

Arg Ala Tyr Ala His Gly Gly Ala Ser Asp Thr Ser Asn Ser Gly Asn
    435                 440                 445

Ala Gly Ile Leu Ser Pro Arg Asp Ser Thr Cys Ala Lys Val Val Glu
450                 455                 460

Tyr Val Phe Ser Gly Ser Pro Thr Asn Lys Asp Ser Ser Leu Ser Gly
465                 470                 475                 480

Leu Glu Pro His Leu Arg Asn Leu Lys Phe Asp Asp Asn Asp Lys Ser
            485                 490                 495

Arg Asp Asp Lys Glu Lys Ala Asn Ser Pro Phe Asp Thr Asn Gly Leu
        500                 505                 510

Lys Lys Asp Asp Gln Val Thr Asn Ser Asn Gly Val Val Asn Gly Ile
    515                 520                 525

Asp Asp Asp Lys Gly Phe Asn Arg Thr Pro Gly Ser Arg Gln Pro Ser
530                 535                 540

Pro Ala Glu Glu Ser Gln Pro Arg Pro Pro Asn Leu Leu Phe Pro Pro
545                 550                 555                 560

Leu Pro Phe Asn His Met Leu Met Asp His Gly Gln Gly Met Gly Gly
            565                 570                 575

Gly Leu Gly Gly Val Val Gly Ser Gly Asn Gly Val Gly Gly Gly Ser
        580                 585                 590

Gly Gly Gly Gly Ala Gly Gly Ala Tyr Ala Ala His Gln Gln Met Ala
    595                 600                 605

Ala Gln Met Ser Gln Leu Gln Pro Pro Met Met Asn Gly Val Gly Gly
610                 615                 620

Gly Met Pro Met Ala Ala Gln Ser Pro Met Leu Asn His Gln Ala Ala
625                 630                 635                 640

Gly Pro Asn His Met Glu Ser Pro Gly Asn Leu Leu Gln Gln Gln Asn
            645                 650                 655

Phe Asp Val Gln Gln Leu Phe Arg Ser Gln Asn Pro Gly Leu Ala Ala
        660                 665                 670

Val Ala Thr Asn Ala Ala Ala Ala Ala Ala Ala Ala Ala Ala Ala Thr
    675                 680                 685

Ser Ala Ala Ser Ala Ala Ala Ala Val Gly Ala Pro Pro Val Pro Asn
690                 695                 700

Gly Ser Leu Gln Gln Ser Gln Gln Gln Gln Gln Gln Gln Gln Gln Gln
705                 710                 715                 720

Gln Gln Gln Gln Gln Met His Met Ala Ala Ala Ser Gln Gln Phe Leu
            725                 730                 735

Ala Ala Gln Gln Gln Ala Gln Asn Ala Ala Tyr Ala Ala Gln Gln Ala
        740                 745                 750

Thr Ser Tyr Val Ile Asn Pro Gly Gln Glu Ala Ala Pro Tyr Met Gly
    755                 760                 765

Met Ile Ala Ala Ala Gln Met Pro Tyr Tyr Gly Val Ala Pro Trp Gly
770                 775                 780

Met Tyr Pro Gly Asn Leu Ile Pro Gln Gln Gly Thr Gln Pro Arg Arg
785                 790                 795                 800

Pro Leu Thr Pro Ser Gln Gln Gly Ala Glu Asn Gln Pro Tyr Gln Val
```

```
            805                 810                 815
Ile Pro Ala Phe Leu Asp His Thr Gly Ser Leu Leu Met Gly Gly Pro
            820                 825                 830

Arg Thr Gly Thr Pro Met Arg Leu Val Ser Pro Ala Pro Val Leu Val
            835                 840                 845

Pro Pro Gly Ala Thr Arg Ala Gly Pro Pro Pro Gln Gly Pro Gln
850                 855                 860

Leu Tyr Gln Pro Gln Pro Gln Thr Ala Gln Gln Asn Leu Tyr Ser Gln
865                 870                 875                 880

Gln Asn Gly Ser Ser Val Gly Gly Leu Ala Leu Asn Thr Ser Ser Leu
            885                 890                 895

Thr Gly Arg Arg Asp Ser Phe Asp Arg Ser Thr Ser Ala Phe Ser Pro
            900                 905                 910

Ser Thr Met Asp Tyr Thr Ser Ser Gly Val Ala Ala Ala Ala Asn Ala
            915                 920                 925

Val Asn Ser Thr Val Ala Gln Ala Ala Ala Ala Ala Ala Ala Ala
930                 935                 940

Ala Ala Arg Gly Lys Trp Pro Gly Ala Met Ser Gly Ala Ala Ser Gly
945                 950                 955                 960

Ala Tyr Gly Ala Leu Gly Ala Gly Asn Ala Ser Ala Ser Pro Leu Gly
            965                 970                 975

Ala Pro Ile Thr Pro Pro Ser Ala Gln Ser Cys Leu Leu Gly Ser
            980                 985                 990

Arg Ala Pro Gly Ala Glu Ser Arg  Gln Arg Gln Gln Gln  Gln Gln Gln
            995                 1000                1005

Leu Ala  Ala Val Gly Leu Pro  Ala Thr Ala Ala Ala  Ala Gln Ala
    1010                1015                1020

Ala Val  Ala Ala Ala Ala Asn  Asn Met Phe Gly Ser  Asn Ser Ser
    1025                1030                1035

Ile Phe  Ser Asn Pro Leu Ala  Ile Pro Gly Thr Ala  Ala Val Ala
    1040                1045                1050

Ala Ala  Ala Ala Ala Ala Ala  Ala Ala Asn Ser Arg  Gln Val Ala
    1055                1060                1065

Ala Thr  Ala Ala Ala Ala Ala  Ala Val Ala Ala Ala  Ala Gly Gly
    1070                1075                1080

Val Gly  Gly Ala Pro Gln Pro  Gly Arg Ser Arg Leu  Leu Glu Asp
    1085                1090                1095

Phe Arg  Asn Gln Arg Tyr Pro  Asn Leu Gln Leu Arg  Asp Leu Ala
    1100                1105                1110

Asn His  Ile Val Glu Phe Ser  Gln Asp Gln His Gly  Ser Arg Phe
    1115                1120                1125

Ile Gln  Gln Lys Leu Glu Arg  Ala Thr Ala Ala Glu  Lys Gln Met
    1130                1135                1140

Val Phe  Ser Glu Ile Leu Ala  Ala Ala Tyr Ser Leu  Met Thr Asp
    1145                1150                1155

Val Phe  Gly Asn Tyr Val Ile  Gln Lys Phe Phe Glu  Phe Gly Thr
    1160                1165                1170

Pro Glu  Gln Lys Asn Thr Leu  Gly Met Gln Val Lys  Gly His Val
    1175                1180                1185

Leu Gln  Leu Ala Leu Gln Met  Tyr Gly Cys Arg Val  Ile Gln Lys
    1190                1195                1200

Ala Leu  Glu Ser Ile Ser Pro  Glu Gln Gln Gln Glu  Ile Val His
    1205                1210                1215
```

Glu Leu Asp Gly His Val Leu Lys Cys Val Lys Asp Gln Asn Gly
1220                1225                1230

Asn His Val Val Gln Lys Cys Ile Glu Cys Val Asp Pro Val Ala
1235                1240                1245

Leu Gln Phe Ile Ile Asn Ala Phe Lys Gly Gln Val Tyr Ser Leu
1250                1255                1260

Ser Thr His Pro Tyr Gly Cys Arg Val Ile Gln Arg Ile Leu Glu
1265                1270                1275

His Cys Thr Ala Glu Gln Thr Thr Pro Ile Leu Asp Glu Leu His
1280                1285                1290

Glu His Thr Glu Gln Leu Ile Gln Asp Gln Tyr Gly Asn Tyr Val
1295                1300                1305

Ile Gln His Val Leu Glu His Gly Lys Gln Glu Asp Lys Ser Ile
1310                1315                1320

Leu Ile Asn Ser Val Arg Gly Lys Val Leu Val Leu Ser Gln His
1325                1330                1335

Lys Phe Ala Ser Asn Val Val Glu Lys Cys Val Thr His Ala Thr
1340                1345                1350

Arg Gly Glu Arg Thr Gly Leu Ile Asp Glu Val Cys Thr Phe Asn
1355                1360                1365

Asp Asn Ala Leu His Val Met Met Lys Asp Gln Tyr Ala Asn Tyr
1370                1375                1380

Val Val Gln Lys Met Ile Asp Val Ser Glu Pro Thr Gln Leu Lys
1385                1390                1395

Lys Leu Met Thr Lys Ile Arg Lys Asn Met Ala Ala Leu Arg Lys
1400                1405                1410

Tyr Thr Tyr Gly Lys His Ile Asn Ala Lys Leu Glu Lys Tyr Tyr
1415                1420                1425

Met Lys Ile Thr Asn Pro Ile Thr Val Gly Thr Gly Ala Gly Gly
1430                1435                1440

Val Pro Ala Ala Ser Ser Ala Ala Ala Val Ser Ser Gly Ala Thr
1445                1450                1455

Ser Ala Ser Val Thr Ala Cys Thr Ser Gly Ser Ser Thr Thr Thr
1460                1465                1470

Thr Ser Thr Thr Asn Ser Leu Ala Ser Pro Thr Ile Cys Ser Val
1475                1480                1485

Gln Glu Asn Gly Ser Ala Met Val Val Glu Pro Ser Ser Pro Asp
1490                1495                1500

Ala Ser Glu Ser Ser Ser Ser Val Val Ser Gly Ala Val Asn Ser
1505                1510                1515

Ser Leu Gly Pro Ile Gly Pro Pro Thr Asn Gly Asn Val Val Leu
1520                1525                1530

<210> SEQ ID NO 8
<211> LENGTH: 6120
<212> TYPE: DNA
<213> ORGANISM: Drosophila melanogaster

<400> SEQUENCE: 8
agtgttgcaa aacgcgcgtg tggttccttg tgctgcaagt taaatacaa ttcaagttgg      60 caatacgcgc aaaattgtca gctgcgatag ctaggaaaag cctccaaaat tgagctccta     120
accgcgccca caattgccat atcgacgccc tcgccgcagc agcaacacca acagcagcag     180
cagcagcagc agcagcaact ctatcagcaa catcaacagc agcagcagca acattacggt     240

```
ccaccaccgc cctactttca acagctacac cagcaacacc aacagcagca gcaacaacag    300
cagcagcagc aacaccagca acacatgaag tttttgggtg gtaacgatga tcgcaatggc    360
cgcggaggcg tcggcgttgg cacggatgcc attgtaggat ctcgaggtgg cgtctctcag    420
gatgccgcca tgcagctgg tgccgccgca gccgccgccg tcggctatgt cttccagcag     480
cgtccatcgc ctggtggggt tggcgtcggc gtgggcggag tgggtggcgg tgtgccaggg    540
gtcggagccg taggctcgac cttgcacgag gccgccgccg ccgagtacgc cgcccacttt    600
gcccagaagc aacagcagac ccgatgggcg tgcggcgacg acggccatgg gatcgataac    660
ccggacaaat ggaagtacaa tccgccgatg aatccggcca atgccgctcc tggcggtcca    720
ccgggaaatg gcagtaatgg tgggcccggc gccattggaa ccattggcat gggcagcgga    780
ttgggtggtg gtgcggcgg cggagctggc ggcggaaata atggcggctc tggtacgaat    840
ggcggtctgc atcatcaatc gatggccgct gcagctgcga atatggcagc catgcaacag    900
gcggcggcgt tggccaagca caatcacatg atatcacagg cagcagccgc agttgcagcc    960
cagcaacaac atcagcatcc acaccagcag catccccagc agcagcagca acagcagcag   1020
gcgcagaacc aggggcatcc acatcaccTT atgggcggtg gcaatggact gggcaacggc   1080
aatggattgg gcatacaaca tcccggccag caacagcagc agcagcagca acaacagcag   1140
cagcaacatc ccgccagta caacgcgaat ctgcttaacc atgcggctgc cttgggtcac   1200
atgtcatctt atgcccaatc gggtggcagc atgtacgacc atcatggtgg agccatgcac   1260 ccggaatga acgcggcat gcccaagcaa cagccattgg gtccacccgg agccggagga    1320
ccccaggact atgtctacat gggtggccag accactgtgc ccatgggagc cgcaatgatg   1380
ccgccacaga atcaatatat gaacagcgct gctgttgcag ctgccaatcg gaatgcagcg   1440
attaccacat ccactgccaa gaaattgtgg gagaaatccg atggcaaggg cgtatcctcg   1500
agcactcccg gtggaccgtt gcatcccctg cagatcccg gcatcgggga tccctcctcc    1560
gtgtggaagg atcacacctg gtccacacag ggcgagaata tattggtgcc gccccctcg   1620 cgagcctacg cccatggagg cgcctccgat acttcaaaca gcggcaatgc gggcatactg   1680
agtccccgcg attcgacttg cgccaaagtg gttgaatatg ttttcagtgg ctcgcccacc   1740
aacaaagata gctcgctttc cggattggaa ccgcatttgc ggaatctaaa gtttgacgac   1800
aacgataagt cacgcgacga taaggagaaa gcaaactctc cgtttgacac aaacggtttg   1860
aagaaagacg atcaggtcac aaactcaaat ggtgttgtca acggcattga cgatgacaag   1920
ggcttcaatc gcactcctgg ttcacgtcaa ccatcacctg cagaggagtc ccagccacgt   1980 cccccaatc tactctttcc tccactgccc ttcaatcaca tgctcatgga tcatggccaa   2040
ggcatgggag gcggcttggg cggagttgtt ggatctggca acggagtcgg cggtggcagc   2100
ggcggaggcg gggcaggcgg cgcttatgcg gcccaccagc agatggccgc ccagatgagt   2160
caattgcaac cgccgatgat gaacggcgtt ggcggcggaa tgccaatggc agcacagtca   2220
ccaatgttga atcaccaggc agctggaccc aatcacatgg aatctcccgg aaatctcttg   2280
cagcagcaaa atttttgatgt tcagcaactg tttcgctcgc agaatccggg cctagcagca   2340
gttgccacaa atgcagcggc cgcagcagca gccgcagcag ctgccacatc ggcagcgagt   2400
gctgcggcag cggtgggcgc accacccgtt cccaacggat cgctgcagca gtcgcagcag   2460
caacagcagc agcagcaaca acagcagcag caacaacaga tgcacatggc ggccgcgtcg   2520
caacaatttt tggccgccca gcagcaggcg caaaatgcgg cctatgccgc ccaacaggcc   2580
```

```
acgtcctacg tcatcaatcc gggccaggag gctgccccgt atatgggcat gattgccgcc    2640
gcccagatgc cgtactatgg cgtagcacca tggggcatgt atccgggcaa tctgattccg    2700
caacagggaa cgcagccgcg ccgccccctc acccctcgc agcagggtgc cgagaatcag     2760
ccgtatcagg tcatcccggc attcctcgat cacacgggct ccttgctgat gggaggacct    2820
cgcaccggga cgccgatgcg tctggttagc cccgcccccg ttctggtgcc cccgggcgct    2880
acccgtgccg gccccccgcc ccgcagggc ccacagctgt atcagccgca gccgcagacg     2940
gcccaacaga atctctactc gcagcagaat ggatccagtg tcggaggcct cgccttgaac    3000
acgagctcgt tgacgggtcg ccgcgactcc ttcgaccgca gcacctccgc cttcagtccc    3060
tcgaccatgg actacaccag cagcggtgtg gcagcggccg ccaatgcggt gaacagcaca    3120
gtggcccagg cagcagcagc tgccgcagca gccgccgcag cgcgtggcaa gtggccggga    3180
gcgatgtcgg gagcggccag tggagcctac ggagccctgg gagcgggcaa tgcttcggcc    3240
agtcccctgg gcgcaccaat cacgccgccg ccatcggcgc aatcctgtct cctgggcagt    3300
cgggcacctg gagccgagtc ccgccagcgg cagcagcaac aacagcagct ggccgccgtt    3360
ggtctgccgg cgactgcagc agctgctcag gcagcggtgg ccgcggctgc caacaatatg    3420
ttcggatcca acagctcgat cttctcgaat cccctgccaa ttccgggtac cgcagctgtg    3480
gcagctgcag cggcagcagc agcggccgcc aactcgcgtc aggtggctgc cacggcagcg    3540
gcagcagcgg cggtggcagc agcagccggc ggagtgggag gtgccccaca gccaggaaga    3600
tctcgccttc tcgaagattt ccgcaaccag cggtatccaa atcttcagct acgcgatctc    3660
gctaaccaca ttgtggagtt ctcacaggat cagcacggct cgcggtttat ccaacagaag    3720
ttggagcggg ccaccgccgc cgagaagcaa atggtgttca gcgagatcct ggcggcagcc    3780
tatagcctga tgaccgatgt ctttggcaac tatgtcatcc agaagttctt tgagttcggc    3840
actcccgagc agaagaacac gctgggcatg caggtcaagg gtcatgtgct gcagctggcg    3900
ctgcaaatgt atggctgccg agtgattcag aaggctctgg agagcatctc gccggagcag    3960
cagcaggaaa tcgtccacga actggacgga catgtgctga atgcgtcaa ggatcagaat     4020
ggcaatcatg tggtgcaaaa gtgcattgag tgcgtggacc ccgtggcgct gcagttcatc    4080
atcaatgctt tcaagggtca ggtttactcg ctaagcaccc atccgtatgg atgccgggtg    4140
atccagagaa tccttgagca ttgcactgcc gaacagacca cgcccatttt ggacgaactg    4200
catgagcaca ccgaacagtt gattcaggac caatatggca actatgttat tcagcatgtg    4260
cttgaacacg gcaagcagga ggataagtcg attcttatca acagcgtgcg cggcaaagtt    4320
ctggtgctat cacagcacaa gttcgcctca aacgttgtgg agaaatgtgt tacccatgcc    4380
actcgcggag aacgcactgg tctcatagac gaggtctgca ccttcaacga caacgcgttg    4440
cacgtgatga tgaaggatca gtatgccaac tatgtggtcc aaaaaatgat cgatgtatcg    4500
gagccgacgc agctcaagaa gctgatgacc aagatccgga aaaacatggc cgccttgcgc    4560
aagtacacct acggcaagca catcaatgcc aagttggaga agtactacat gaagataacc    4620
aatcccatta cggtgggcac aggagctgga ggagtgccgg cagcctcgtc ggcggccgca    4680
gtcagcagtg gtgccacctc ggcatcggta accgcctgca ccagtggcag cagcaccacc    4740
acgaccagca ctaccaacag cctggcctca cccaccattt gttcggtgca ggagaacggc    4800
agcgccatgg ttgtggagcc ctcctccccg gacgcctccg agtcctcgtc ctcggtggtg    4860
tcaggcgctg tcaacagcag cttgggtccc attggacccc cgaccaacgg caacgttgtg    4920
ctgtaaagga ataacaaat taagccaggc agtcaaagga aacttccttc tcgaatcgca     4980
```

```
gtatagtttt tagaagctgt agagcttaac ataaacaaca agtacatata aatgtaatct    5040
tatttattgg aaaagcagcg ataaatggag ctgcactcga agatttgcaa agaggatagt    5100
aaaacacaca tgcgccaatc tagagaaaca aatagcaaac aaagaagcac actggcaagc    5160
aaaaaagcaa aagagcttaa cagctaaaac taaaagaaat ttgtattttt acgaacaaaa    5220
ctaataacgt tctcatgaaa aaagatttca aaatatttgt aaaatgcgct cgcataatta    5280
atttgtaaaa aaaaggcatg aaccgcaaag atgaaagaaa acaaaaatgc gtagtaaatc    5340
gcgatcaaga aaaaaataa tgaatgtaat gtaaatgtc aatgaaacag atttgtctgc     5400
gtacattttc gttgtaactt tgtataaatt aattattata tagcaagtct atctgtaaat    5460
gattaatgtt tcgactgtaa attaataaga agacaactga agagccggcg agctgaaaaa    5520
aaataaagta aaaagagcgg gctgcatgaa ttagcctacg atttataagt tcagacagag    5580
gaaccatttc taatatacaa acatatatac gagggataac agcagaagcc gcacttagtg    5640
tagaatgtag agtaataatg tttttggagc cagcagctac aaagacacaa tgaaaacaga    5700
gacacacgag acacgcccac gcccctcac gcacactcgg ttgcatacac ccacacaatg     5760
aacgactctt cagcccattc acgttgcttt tgcactatgt aaaaattttg tataaaaaaa    5820
aaccccaaac aacaaaccat gtaaaccatg taattttcaa atgtttcact gtaaaatgta    5880
tacatacttt attttgtaaa ttttttttaa gtcgcaagta actcatacat attctattct    5940
aaacctcacg catgtattta taatttata cacattagct ggtgaccacc gatcgacgat     6000
ctgcatggat gttggtcagc tggtggccag ctaaaagaac ctgttagcca agtaagccaa    6060
aaatgataat aattggattt taaaacaata accatcaaaa taaccaatt tttttcaaaa     6120
```

<210> SEQ ID NO 9
<211> LENGTH: 61
<212> TYPE: RNA
<213> ORGANISM: Xenopus laevis

<400> SEQUENCE: 9

```
gccggccaca ccuacggggc cugguuagua ccugggaaac cugggaauac caggugccgg    60
c                                                                    61
```

<210> SEQ ID NO 10
<211> LENGTH: 87
<212> TYPE: PRT
<213> ORGANISM: Xenopus laevis

<400> SEQUENCE: 10

Met Tyr Val Cys His Phe Glu Asn Cys Gly Lys Ala Phe Lys Lys His
1               5                   10                  15

Asn Gln Leu Lys Val His Gln Phe Ser His Thr Gln Leu Pro Tyr
            20                  25                  30

Glu Cys Pro His Glu Gly Cys Asp Lys Arg Phe Ser Leu Pro Ser Arg
        35                  40                  45

Leu Lys Arg His Glu Lys Val His Ala Gly Tyr Pro Cys Lys Lys Asp
    50                  55                  60

Asp Ser Cys Ser Phe Val Gly Lys Thr Trp Thr Leu Tyr Leu Lys His
65                  70                  75                  80

Val Ala Glu Cys His Gln Asp
                85

<210> SEQ ID NO 11

```
<211> LENGTH: 97
<212> TYPE: PRT
<213> ORGANISM: Homo sapiens

<400> SEQUENCE: 11

Ala Val Pro Glu Thr Arg Pro Asn His Thr Ile Tyr Ile Asn Asn Leu
1               5                   10                  15

Asn Glu Lys Ile Lys Lys Asp Glu Leu Lys Lys Ser Leu His Ala Ile
                20                  25                  30

Phe Ser Arg Phe Gly Gln Ile Leu Asp Ile Leu Val Ser Arg Ser Leu
            35                  40                  45

Lys Met Arg Gly Gln Ala Phe Val Ile Phe Lys Glu Val Ser Ser Ala
50                  55                  60

Thr Asn Ala Leu Arg Ser Met Gln Gly Phe Pro Phe Tyr Asp Lys Pro
65                  70                  75                  80

Met Arg Ile Gln Tyr Ala Lys Thr Asp Ser Asp Ile Ile Ala Lys Met
                85                  90                  95

Lys

<210> SEQ ID NO 12
<211> LENGTH: 21
<212> TYPE: RNA
<213> ORGANISM: Homo sapiens

<400> SEQUENCE: 12
aauccauugc acuccggauu u                                       21

<210> SEQ ID NO 13
<211> LENGTH: 87
<212> TYPE: PRT
<213> ORGANISM: Homo sapiens

<400> SEQUENCE: 13

Met Lys Glu Leu Val Glu Ile Ala Val Pro Glu Asn Leu Val Gly Ala
1               5                   10                  15

Ile Leu Gly Lys Gly Gly Lys Thr Leu Val Glu Tyr Gln Glu Leu Thr
                20                  25                  30

Gly Ala Arg Ile Gln Ile Ser Lys Lys Gly Glu Phe Leu Pro Gly Thr
            35                  40                  45

Arg Asn Arg Arg Val Thr Ile Thr Gly Ser Pro Ala Ala Thr Gln Ala
50                  55                  60

Ala Gln Tyr Leu Ile Ser Gln Arg Val Thr Tyr Glu Gln Gly Val Arg
65                  70                  75                  80

Ala Ser Asn Pro Gln Lys Val
                85

<210> SEQ ID NO 14
<211> LENGTH: 20
<212> TYPE: RNA
<213> ORGANISM: Homo sapiens

<400> SEQUENCE: 14
gaggaccuag aucaccccuc                                         20

<210> SEQ ID NO 15
<211> LENGTH: 251
<212> TYPE: PRT
<213> ORGANISM: Mycobacterium tuberculosis

<400> SEQUENCE: 15
```

Gly Glu Phe Ser Thr Arg Glu Gly Glu Ile Val Ala Gly Val Ile Gln
1               5                   10                  15

Arg Asp Ser Arg Ala Asn Ala Arg Gly Leu Val Val Arg Ile Gly
            20                  25                  30

Thr Glu Thr Lys Ala Ser Glu Gly Val Ile Pro Ala Ala Glu Gln Val
        35                  40                  45

Pro Gly Glu Ser Tyr Glu His Gly Asn Arg Leu Arg Cys Tyr Val Val
    50                  55                  60

Gly Val Thr Arg Gly Ala Arg Glu Pro Leu Ile Thr Leu Ser Arg Thr
65                  70                  75                  80

His Pro Asn Leu Val Arg Lys Leu Phe Ser Leu Glu Val Pro Glu Ile
                85                  90                  95

Ala Asp Gly Ser Val Glu Ile Val Ala Val Ala Arg Glu Ala Gly His
            100                 105                 110

Arg Ser Lys Ile Ala Val Arg Ser Asn Val Ala Gly Leu Asn Ala Lys
        115                 120                 125

Gly Ala Cys Ile Gly Pro Met Gly Gln Arg Val Arg Asn Val Met Ser
130                 135                 140

Glu Leu Ser Gly Glu Lys Ile Asp Ile Ile Asp Tyr Asp Asp Pro
145                 150                 155                 160

Ala Arg Phe Val Ala Asn Ala Leu Ser Pro Ala Lys Val Val Ser Val
            165                 170                 175

Ser Val Ile Asp Gln Thr Ala Arg Ala Ala Arg Val Val Pro Asp
        180                 185                 190

Phe Gln Leu Ser Leu Ala Ile Gly Lys Glu Gly Gln Asn Ala Arg Leu
                195                 200                 205

Ala Ala Arg Leu Thr Gly Trp Arg Ile Asp Ile Arg Gly Asp Ala Pro
210                 215                 220

Pro Pro Pro Pro Gly Gln Pro Glu Pro Gly Val Ser Arg Gly Met Ala
225                 230                 235                 240

His Asp Arg Leu Glu His His His His His His
                245                 250

<210> SEQ ID NO 16
<211> LENGTH: 11
<212> TYPE: RNA
<213> ORGANISM: Mycobacterium tuberculosis

<400> SEQUENCE: 16
gaacucaaua g                                                                11

<210> SEQ ID NO 17
<211> LENGTH: 76
<212> TYPE: PRT
<213> ORGANISM: Drosophila melanogaster

<400> SEQUENCE: 17

Met Asp Glu Gly Asp Lys Lys Ser Pro Ile Ser Gln Val His Glu Ile
1               5                   10                  15

Gly Ile Lys Arg Asn Met Thr Val His Phe Lys Val Leu Arg Glu Glu
            20                  25                  30

Gly Pro Ala His Met Lys Asn Phe Ile Thr Ala Cys Ile Val Gly Ser
        35                  40                  45

Ile Val Thr Glu Gly Glu Gly Asn Gly Lys Lys Val Ser Lys Lys Arg
    50                  55                  60

Ala Ala Glu Lys Met Leu Val Glu Leu Gln Lys Leu
65                  70                  75

<210> SEQ ID NO 18
<211> LENGTH: 30
<212> TYPE: RNA
<213> ORGANISM: Drosophila melanogaster

<400> SEQUENCE: 18
ggacagcugu cccuucgggg acagcugucc                                       30

<210> SEQ ID NO 19
<211> LENGTH: 245
<212> TYPE: PRT
<213> ORGANISM: Escherichia coli

<400> SEQUENCE: 19

Met Ser Leu Arg Ser Asp Leu Ile Asn Ala Leu Tyr Asp Glu Asn Gln
1               5                   10                  15

Lys Tyr Asp Val Cys Gly Ile Ile Ser Ala Glu Gly Lys Ile Tyr Pro
            20                  25                  30

Leu Gly Ser Asp Thr Lys Val Leu Ser Thr Ile Phe Glu Leu Phe Ser
        35                  40                  45

Arg Pro Ile Ile Asn Lys Ile Ala Glu Lys His Gly Tyr Ile Val Glu
    50                  55                  60

Glu Pro Lys Gln Gln Asn His Tyr Pro Asp Phe Thr Leu Tyr Lys Pro
65                  70                  75                  80

Ser Glu Pro Asn Lys Lys Ile Ala Ile Asp Ile Lys Thr Thr Tyr Thr
                85                  90                  95

Asn Lys Glu Asn Glu Lys Ile Lys Phe Thr Leu Gly Gly Tyr Thr Ser
            100                 105                 110

Phe Ile Arg Asn Asn Thr Lys Asn Ile Val Tyr Pro Phe Asp Gln Tyr
        115                 120                 125

Ile Ala His Trp Ile Ile Gly Tyr Val Tyr Thr Arg Val Ala Thr Arg
    130                 135                 140

Lys Ser Ser Leu Lys Thr Tyr Asn Ile Asn Glu Leu Asn Glu Ile Pro
145                 150                 155                 160

Lys Pro Tyr Lys Gly Val Lys Val Phe Leu Gln Asp Lys Trp Val Ile
                165                 170                 175

Ala Gly Asp Leu Ala Gly Ser Gly Asn Thr Thr Asn Ile Gly Ser Ile
            180                 185                 190

His Ala His Tyr Lys Asp Phe Val Glu Gly Lys Gly Ile Phe Asp Ser
        195                 200                 205

Glu Asp Glu Phe Leu Asp Tyr Trp Arg Asn Tyr Glu Arg Thr Ser Gln
    210                 215                 220

Leu Arg Asn Asp Lys Tyr Asn Asn Ile Ser Glu Tyr Arg Asn Trp Ile
225                 230                 235                 240

Tyr Arg Gly Arg Lys
                245

<210> SEQ ID NO 20
<211> LENGTH: 738
<212> TYPE: DNA
<213> ORGANISM: Escherichia coli

<400> SEQUENCE: 20
atgagtcttc gttctgattt aattaatgca ctatatgatg aaaatcaaaa atatgatgta    60

```
tgcggaataa tatctgcaga aggaaaaata tacccattgg gaagtgacac aaaagttcta    120
agcacaatat ttgagttatt ctcaagacca ataataaata aaatagcaga aaacatggg     180 tatattgtag aagaacctaa acaacaaat cattatcctg actttactct ttacaaacca    240
agcgaaccaa ataaaaaaat tgcaatagat ataaaaacaa catatacaaa caagaaaac    300 gaaaaaatca agttcactct tggtgggtat accagcttta tacgaaacaa cacaaaaat    360 attgtttatc catttgacca atatatcgcc cattggataa tcggatatgt atatacaaga    420
gttgccacaa gaaaatcatc tttaaaaaca tataatataa atgaactcaa tgaaatccct    480
aaaccataca aaggcgtaaa ggttttctta caagataaat gggttattgc tggagatttg    540
gcaggatctg gaaacacaac aaatataggt agcattcatg cccactataa agactttgta    600
gaaggaaaag gaatatttga ctcagaggat gagttttag actattggag aaattatgaa    660
agaaccagtc aattaagaaa tgacaagtat aataatataa gcgaatacag aaactggata    720
taccgaggaa gaaaataa                                                  738

<210> SEQ ID NO 21
<211> LENGTH: 1611
<212> TYPE: PRT
<213> ORGANISM: Bos taurus

<400> SEQUENCE: 21

Met Pro Ala Arg Thr Ala Pro Ala Arg Val Pro Ala Leu Ala Ser Arg
1               5                   10                  15

Ala Phe Ser Leu Pro Asp Asp Val Arg Arg Leu Lys Asp Leu Glu
            20                  25                  30

Arg Asp Ser Leu Thr Glu Lys Glu Cys Val Lys Glu Lys Leu Asn Leu
        35                  40                  45

Leu His Glu Phe Leu Arg Thr Glu Ile Lys Asn Gln Leu Cys Asp Leu
    50                  55                  60

Glu Thr Lys Leu His Lys Glu Glu Leu Ser Glu Glu Gly Tyr Leu Ala
65                  70                  75                  80

Lys Val Lys Ser Leu Leu Asn Lys Asp Leu Ser Leu Glu Asn Gly Ala
                85                  90                  95

His Ala Phe Ser Arg Glu Ala Asn Gly Cys Leu Glu Asn Gly Ser Gln
            100                 105                 110

Thr Ser Gly Glu Asp Cys Arg Val Val Met Ala Glu Lys Gly Lys Pro
        115                 120                 125

Pro Lys Pro Val Ser Arg Leu Tyr Thr Pro Arg Arg Ser Lys Ser Asp
    130                 135                 140

Gly Glu Thr Lys Ser Glu Val Ser Ser Ser Pro Arg Ile Thr Arg Lys
145                 150                 155                 160

Thr Thr Arg Gln Thr Thr Ile Thr Ser His Phe Pro Arg Gly Pro Ala
                165                 170                 175

Lys Arg Lys Pro Glu Glu Glu Pro Glu Lys Val Lys Ser Asp Asp Ser
            180                 185                 190

Val Asp Glu Glu Lys Asp Gln Glu Glu Lys Arg Arg Val Thr Ser
        195                 200                 205

Arg Glu Arg Val Ala Gly Leu Leu Pro Ala Glu Pro Gly Arg Val
    210                 215                 220

Arg Pro Gly Thr His Met Glu Glu Glu Gly Arg Asp Asp Lys Glu Glu
225                 230                 235                 240

Lys Arg Leu Arg Ser Gln Thr Lys Glu Pro Thr Pro Lys His Lys Ala
                245                 250                 255
```

-continued

Lys Glu Glu Pro Asp Arg Asp Val Arg Pro Gly Gly Ala Gln Ala Glu
            260                 265                 270

Met Asn Glu Gly Glu Asp Lys Asp Glu Lys Arg His Arg Ser Gln Pro
            275                 280                 285

Lys Asp Leu Ala Ser Lys Arg Arg Pro Glu Glu Lys Glu Pro Glu Arg
            290                 295                 300

Val Lys Pro Gln Val Ser Asp Glu Lys Asp Glu Asp Glu Lys Glu Glu
305                 310                 315                 320

Lys Arg Arg Arg Thr Thr Tyr Arg Glu Leu Thr Lys Lys Met Thr
                325                 330                 335

Arg Thr Lys Ile Ala Val Val Ser Lys Thr Asn Pro Lys Cys Thr
                340                 345                 350

Glu Cys Leu Gln Tyr Leu Asp Asp Pro Glu Leu Arg Tyr Glu Gln His
            355                 360                 365

Pro Pro Asp Ala Val Glu Glu Ile Gln Ile Leu Thr Asn Glu Arg Leu
            370                 375                 380

Ser Ile Phe Asp Ala Asn Glu Ser Gly Phe Glu Ser Tyr Glu Asp Leu
385                 390                 395                 400

Pro Gln His Lys Leu Thr Cys Phe Ser Val Tyr Cys Lys Arg Gly His
                405                 410                 415

Leu Cys Pro Ile Asp Thr Gly Leu Ile Glu Lys Asp Val Glu Leu Leu
                420                 425                 430

Phe Ser Gly Ser Ala Lys Pro Ile Tyr Glu Asp Asp Pro Ser Pro Glu
            435                 440                 445

Gly Gly Ile Asn Gly Lys Asn Phe Gly Pro Ile Asn Glu Trp Trp Ile
            450                 455                 460

Ala Gly Phe Asp Gly Gly Glu Lys Ala Leu Leu Gly Phe Ser Thr Ser
465                 470                 475                 480

Phe Ala Glu Tyr Ile Leu Met Asp Pro Ser Pro Glu Tyr Ala Pro Leu
                485                 490                 495

Phe Ser Val Met Gln Glu Lys Ile Tyr Ile Ser Lys Ile Val Val Glu
                500                 505                 510

Phe Leu Gln Ser Asn Pro Asp Ser Thr Tyr Glu Asp Leu Ile Asn Lys
            515                 520                 525

Ile Glu Thr Thr Val Pro Pro Cys Met Leu Asn Leu Asn Arg Phe Thr
            530                 535                 540

Glu Asp Ser Leu Leu Arg His Ala Gln Phe Val Val Glu Gln Val Glu
545                 550                 555                 560

Ser Tyr Asp Arg Ala Gly Asp Ser Asp Glu Gln Pro Ile Phe Leu Ser
                565                 570                 575

Pro Cys Met Arg Asp Leu Ile Lys Leu Ala Gly Val Thr Leu Gly Lys
                580                 585                 590

Arg Arg Ala Glu Arg Arg Gln Thr Ile Arg Gln Pro Ala Lys Glu Lys
            595                 600                 605

Asp Lys Gly Pro Thr Lys Ala Thr Thr Thr Lys Leu Val Tyr Gln Ile
            610                 615                 620

Phe Asp Thr Phe Phe Ala Glu Gln Ile Glu Lys Asp Asp Lys Glu Asp
625                 630                 635                 640

Lys Glu Asn Ala Phe Lys Arg Arg Cys Gly Val Cys Glu Ile Cys
                645                 650                 655

Gln Gln Pro Glu Cys Gly Lys Cys Lys Ala Cys Lys Asp Met Val Lys
            660                 665                 670

```
Phe Gly Gly Ser Gly Arg Ser Lys Gln Ala Cys Gln Lys Arg Arg Cys
            675                 680                 685

Pro Asn Met Ala Met Lys Glu Ala Asp Asp Glu Glu Val Asp Asp
690                 695                 700

Asn Ile Pro Glu Met Pro Ser Pro Lys Met His Gln Gly Lys Lys
705                 710                 715                 720

Lys Lys Gln Asn Lys Asn Arg Ile Ser Trp Val Gly Asp Ala Val Lys
                725                 730                 735

Thr Asp Gly Lys Lys Ser Tyr Tyr Lys Val Cys Ile Asp Ser Glu
            740                 745                 750

Thr Leu Glu Val Gly Asp Cys Val Ser Val Ile Pro Asp Asp Ser Ser
            755                 760                 765

Lys Pro Leu Tyr Leu Ala Arg Val Thr Ala Leu Trp Glu Asp Ser Ser
770                 775                 780

Asn Gly Gln Met Phe His Ala His Trp Phe Cys Ala Gly Thr Asp Thr
785                 790                 795                 800

Val Leu Gly Ala Thr Ser Asp Pro Leu Glu Leu Phe Leu Val Asp Glu
            805                 810                 815

Cys Glu Asp Met Gln Leu Ser Tyr Ile His Ser Lys Val Gln Val Ile
            820                 825                 830

Tyr Lys Ala Pro Ser Glu Asn Trp Ala Met Glu Gly Gly Val Asp Pro
            835                 840                 845

Glu Ala Leu Met Ser Glu Asp Gly Lys Thr Tyr Phe Tyr Gln Leu
            850                 855                 860

Trp Tyr Asp Gln Asp Tyr Ala Arg Phe Glu Ser Pro Pro Lys Thr Gln
865                 870                 875                 880

Pro Thr Glu Asp Asn Lys Tyr Lys Phe Cys Ala Ser Cys Ala Arg Leu
                885                 890                 895

Ala Glu Met Arg Gln Lys Glu Ile Pro Arg Val Val Glu Gln Leu Gln
                900                 905                 910

Asp Leu Glu Gly Arg Val Leu Tyr Ser Leu Ala Thr Lys Asn Gly Val
            915                 920                 925

Gln Tyr Arg Val Gly Asp Gly Val Tyr Leu Pro Pro Glu Ala Phe Thr
930                 935                 940

Phe Asn Ile Lys Leu Ser Ser Pro Val Lys Arg Pro Arg Lys Glu Pro
945                 950                 955                 960

Val Asp Glu Ala Leu Tyr Pro Glu His Tyr Arg Lys Tyr Ser Asp Tyr
                965                 970                 975

Ile Lys Gly Ser Asn Leu Asp Ala Pro Glu Pro Tyr Arg Ile Gly Arg
            980                 985                 990

Ile Lys Glu Ile Phe Cys Ser Lys Lys Ser Asn Gly Arg Pro Asn Glu
            995                 1000                1005

Thr Asp Ile Lys Ile Arg Val Asn Lys Phe Tyr Arg Pro Glu Asn
    1010                1015                1020

Thr His Lys Ser Thr Pro Ala Ser Tyr His Ala Asp Ile Asn Leu
    1025                1030                1035

Leu Tyr Trp Ser Asp Glu Glu Ala Val Val Asp Phe Lys Ala Val
    1040                1045                1050

Gln Gly Arg Cys Thr Val Glu Tyr Gly Glu Asp Leu Pro Gln Cys
    1055                1060                1065

Leu Gln Asp Phe Ser Ala Gly Gly Pro Asp Arg Phe Tyr Phe Leu
    1070                1075                1080

Glu Ala Tyr Asn Ala Lys Ser Lys Ser Phe Glu Asp Pro Pro Asn
```

```
                1085                1090                1095
    His Ala Arg Ser Thr Gly Asn Lys Gly Lys Gly Lys Gly
        1100                1105                1110

Lys Asn Arg Thr Lys Ser Gln Thr Cys Glu Pro Ser Glu Leu Glu
        1115                1120                1125

Thr Glu Ile Lys Leu Pro Lys Leu Arg Thr Leu Asp Val Phe Ser
        1130                1135                1140

Gly Cys Gly Gly Leu Ser Glu Gly Phe His Gln Ala Gly Ile Ser
        1145                1150                1155

Glu Thr Leu Trp Ala Ile Glu Met Trp Asp Pro Ala Ala Gln Ala
        1160                1165                1170

Phe Arg Leu Asn Asn Pro Gly Ser Thr Val Phe Thr Glu Asp Cys
        1175                1180                1185

Asn Val Leu Leu Lys Leu Val Met Ala Gly Glu Val Thr Asn Ser
        1190                1195                1200

Arg Gly Gln Lys Leu Pro Gln Lys Gly Asp Val Glu Met Leu Cys
        1205                1210                1215

Gly Gly Pro Pro Cys Gln Gly Phe Ser Gly Met Asn Arg Phe Asn
        1220                1225                1230

Ser Arg Thr Tyr Ser Lys Phe Lys Asn Ser Leu Val Val Ser Phe
        1235                1240                1245

Leu Ser Tyr Cys Asp Tyr Tyr Arg Pro Arg Tyr Phe Leu Leu Glu
        1250                1255                1260

Asn Val Arg Asn Phe Val Ser Phe Lys Arg Ser Met Val Leu Lys
        1265                1270                1275

Leu Thr Leu Arg Cys Leu Val Arg Met Gly Tyr Gln Cys Thr Phe
        1280                1285                1290

Gly Val Leu Gln Ala Gly Gln Tyr Gly Val Ala Gln Thr Arg Arg
        1295                1300                1305

Arg Ala Ile Ile Leu Ala Ala Ala Pro Gly Glu Pro Leu Pro Leu
        1310                1315                1320

Phe Pro Glu Pro Leu His Val Phe Ala Pro Arg Ala Cys Gln Leu
        1325                1330                1335

Ser Val Val Val Asp Asp Lys Lys Phe Val Ser Asn Ile Thr Arg
        1340                1345                1350

Leu Ser Ser Gly Pro Phe Arg Thr Ile Thr Val Arg Asp Thr Met
        1355                1360                1365

Ser Asp Leu Pro Glu Ile Arg Asn Gly Ala Ser Ala Leu Glu Ile
        1370                1375                1380

Ser Tyr Asn Gly Glu Pro Gln Ser Trp Phe Gln Arg Gln Leu Arg
        1385                1390                1395

Gly Ser Gln Tyr Gln Pro Ile Leu Arg Asp His Ile Cys Lys Asp
        1400                1405                1410

Met Ser Ala Leu Val Ala Ala Arg Met Arg His Ile Pro Leu Ala
        1415                1420                1425

Pro Gly Ser Asp Trp Arg Asp Leu Pro Asn Ile Glu Val Arg Leu
        1430                1435                1440

Ser Asp Gly Thr Leu Ala Arg Lys Leu Arg Tyr Asn Tyr His Asp
        1445                1450                1455

Lys Lys Asn Gly Cys Ser Ser Ser Gly Ala Leu Arg Gly Val Cys
        1460                1465                1470

Ser Cys Val Glu Gly Lys Pro Cys Glu Pro Ala Ala Arg Gln Phe
        1475                1480                1485
```

```
Asn Thr Leu Ile Pro Trp Cys Leu Pro His Thr Gly Asn Arg His
    1490                1495                1500

Asn His Trp Ala Gly Leu Tyr Gly Arg Leu Glu Trp Asp Gly Phe
    1505                1510                1515

Phe Ser Thr Thr Val Thr Asn Pro Glu Pro Met Gly Lys Gln Gly
    1520                1525                1530

Arg Val Leu His Pro Glu Gln His Arg Val Val Ser Val Arg Glu
    1535                1540                1545

Cys Ala Arg Ser Gln Gly Phe Pro Asp Thr Tyr Arg Leu Phe Gly
    1550                1555                1560

Asn Ile Leu Asp Lys His Arg Gln Val Gly Asn Ala Val Pro Pro
    1565                1570                1575

Pro Leu Ala Lys Ala Ile Gly Leu Glu Ile Lys Arg Cys Met Leu
    1580                1585                1590

Ala Lys Ala Arg Glu Ser Ala Ser Ala Lys Ile Lys Glu Glu Ala
    1595                1600                1605

Ala Lys Asp
    1610

<210> SEQ ID NO 22
<211> LENGTH: 5192
<212> TYPE: DNA
<213> ORGANISM: Bos taurus
<220> FEATURE:
<221> NAME/KEY: modified_base
<222> LOCATION: (5013)..(5013)
<223> OTHER INFORMATION: a, c, t, g, unknown or other
<220> FEATURE:
<221> NAME/KEY: modified_base
<222> LOCATION: (5077)..(5077)
<223> OTHER INFORMATION: a, c, t, g, unknown or other
<220> FEATURE:
<221> NAME/KEY: modified_base
<222> LOCATION: (5100)..(5100)
<223> OTHER INFORMATION: a, c, t, g, unknown or other
<220> FEATURE:
<221> NAME/KEY: modified_base
<222> LOCATION: (5119)..(5119)
<223> OTHER INFORMATION: a, c, t, g, unknown or other
<220> FEATURE:
<221> NAME/KEY: modified_base
<222> LOCATION: (5132)..(5132)
<223> OTHER INFORMATION: a, c, t, g, unknown or other

<400> SEQUENCE: 22
aagatgcctg cccgaaccgc cccggcgcgg gtgcctgcgc tggcctcccg ggccttctca      60
ctgcctgacg atgtccgcag gcggctcaaa gatttggaaa gagatagttt gacagaaaag     120
gaatgtgtga aggagaaact gaatctcttg cacgaatttc tgcggacaga aataaagaat     180
cagttatgtg atttggaaac caaattgcat aaagaagaat tatctgagga gggctacctg     240
gctaaagtca atccttttt aaataaagat ttgtccttgg agaacggagc tcatgctttc     300
agtcgggaag cgaatggatg tctagagaac gggagccaga caagtggtga ggattgcaga     360
gtggtaatgg cagagaaagg caagcccccc aaacctgtct ccagacttta cacgcccagg     420
agaagcaagt ctgatggaga aacaaagtct gaagtctctt ctagccccag gattacaagg     480
aagactacca ggcagaccac catcacatct catttcccac ggggccctgc caaacgaaaa     540
cctgaggaag aacctgaaaa agtgaagtca gacgattctg ttgatgaaga aaaagaccag     600
gaggaaagaa gacgtcgagt tacatccaga gaacgagttg ctgggctgct ccctgcagaa     660
gaaccaggaa gagtaagacc aggaacacac atggaagaag aaggaagaga tgataaagaa     720
```

```
gaaaagagac tcagaagtca aaccaaagaa ccgacaccta acacaaagc taaggaggag      780 ccagacagag atgtgaggcc tggaggagct caggctgaaa tgaatgaagg agaagacaaa      840
gatgaaaaga ggcacagaag tcaacccaaa gatctagcta gcaaacggag accagaagaa      900
aaagaacctg aaagagtaaa gccacaagtt tctgatgaga agatgaaga tgaaaaggag       960 gagaagagac gcagaactac atacagagaa ctaaccgaga agaaaatgac tcgaaccaaa     1020
atagccgtag tgtccaagac caatcctccg aagtgcaccg agtgcttgca gtacctggac     1080
gaccctgagc tgagatacga gcagcacccc cccgatgcgg tggaagagat acagatactg     1140
accaacgaga ggttgtccat ctttgatgcc aacgaatctg gctttgagag ttacgaggat     1200
ttgcctcagc acaaactaac ctgcttcagc gtgtactgta aacgcggtca cctttgcccg     1260
atcgacaccg gcctcattga aaggatgtc gagctcctct tttctggttc agcaaagccg      1320
atatatgagg atgacccatc tcccgaaggt ggtattaatg caaaaattt tggccccata      1380 aacgaatggt ggattgctgg ttttgatgga ggtgaaaagg ctcttcttgg ctttagcacc     1440
tcatttgccg agtatatctt gatggatccc agcccagagt acgcaccact attcagcgtg     1500
atgcaggaga agatctatat aagtaagata gtggttgagt tcctgcagag caaccctgac     1560
tccacctacg aagacctgat caataagatt gagaccaccg ttcctccttg tatgctcaac     1620
ttgaatcgat tcacagagga ttctctcctg cggcatgccc agttcgtggt ggagcaagta     1680
gagagttatg atcgggctgg ggacagtgac gagcagccca tcttcctgag cccctgcatg     1740
agagacctca tcaagctggc cggggtcacc ctgggaaaaa ggcgagccga gaggcggcag     1800
accatccggc aaccgccaa agagaaggac aagggcccca ccaaggccac caccaccaag      1860
ctggtctacc agatctttga cactttcttt gcggagcaaa ttgaaaaaga tgacaaggaa     1920
gacaaggaga atgccttcaa gcgccggcgc tgtggcgtct gtgagatttg tcaacagccc     1980
gagtgtggaa agtgtaaggc ctgtaaggat atggttaaat ttggtggtag cggacggagc     2040
aagcaggctt gccaaaagag gaggtgtccc aacatggcca tgaaggaggc agacgatgac     2100
gaggaagtgg atgacaatat tccagagatg ccatcaccca aaagatgca tcaggggaag      2160 aaaaagaagc agaataagaa tcggatctct tgggttggcg atgccgtcaa gactgacggg     2220
aagaagagtt actacaagaa ggtatgcatc gactcggaaa ccctggaagt gggggactgt     2280
gtttctgtaa ttccagacga ctcttcaaaa ccactgtatc tagcaagggt cacggcgctg     2340
tgggaggaca gcagcaatgg gcagatgttc catgcccact ggttctgtgc tgggacggac     2400
acggtcctcg gggccacatc ggaccccctg gagctgttcc tggttgacga gtgtgaggac     2460
atgcagctct cgtacatcca gcaaggtg caggtcattt ataaggcgcc ctcagagaac       2520
tgggccatgg agggaggcgt ggaccccgag gccctgatgt cagaggacga cgggaagacc     2580
tacttctacc agctgtggta cgaccaagac tacgcgagat tgagtccccc tccgaaaact     2640
cagccgacgg aggacaacaa gtacaagttc tgccaagct gtgcacgtct ggccgaaatg      2700
aggcagaagg aaatccccag ggtcgtggag cagctccagg acctggaagg ccgcgtcctc     2760
tacagcctcg ccaccaagaa cggcgtccag taccgggtgg cgatggcgt gtacctccct      2820 cccgaggcct tcaccttcaa catcaagctg tccagtcctg tgaaacgccc ccggaaggag     2880
cctgtggacg aagctctgta tccagaacac taccggaagt actctgacta catcaagggc     2940
agcaacctgg atgcccctga gcctaccgt attggccgca taaggagat cttctgcagc      3000 aagaagagca acggccggcc caatgagaca gacatcaaga tcagggtcaa caagttctac     3060
```

| | | | | | |
|---|---|---|---|---|---|
| aggccggaga | acacacacaa | gtctacccca | gccagttacc | acgcagacat | caacctgctt | 3120 |
| tactggagcg | atgaggaggc | cgtggtggac | ttcaaggccg | tgcagggccg | ctgcaccgtg | 3180 |
| gagtacggag | aggacctgcc | tcagtgcctc | caggacttct | ccgctggtgg | ccccgatcgc | 3240 |
| ttctattttc | tcgaggccta | taacgccaag | agcaaaagct | tgaagatcc | tccgaaccac | 3300 |
| gcccggagca | ccggaaataa | agggaaaggg | aaggggaaag | gaaaaaacag | gacgaaatct | 3360 |
| cagacgtgtg | agccgagtga | actggagaca | gaaatcaaac | tgccgaagct | gcggaccctg | 3420 |
| gacgtgtttt | ccggctgtgg | gggattgtcg | gaaggcttcc | accaagcagg | catctcggaa | 3480 |
| acactttggg | ccatcgagat | gtgggaccct | gcggcccagg | cgttccggtt | caacaaccct | 3540 |
| gggtccacgg | tgttcacaaa | ggactgcaac | gtcctggtga | agctggtcat | ggccggggag | 3600 |
| gtgaccaact | cccgcggcca | gaagctgctt | caaaagggag | atgtggagat | gttgtgcggc | 3660 |
| gggccgccct | gccagggctt | tagcggcatg | aaccgcttca | actctcgaac | ctactccaaa | 3720 |
| ttcaagaact | ccctggtggt | ctcttttcctc | agctactgtg | actactaccg | gccccgctac | 3780 |
| ttcctcttgg | agaacgttcg | gaacttcgtc | tccttcaagc | gctccatggt | cctgaagctg | 3840 |
| acgctgcgct | gcctggtccg | caggggggtac | cagtgcacct | ttggcgtgct | gcaggctggt | 3900 |
| cagtacggcg | tggcccagac | tcggaggcga | gccatcatcc | tggctgcagc | cctggggag | 3960 |
| ccactcccgc | tgttcccgga | gccgttgcat | gtgttcgcac | ccgggcctg | ccagctgagc | 4020 |
| gtcgtagtgg | acgacaagaa | gtttgtcagc | aacatcacca | ggttgagctc | gggtcccttc | 4080 |
| cgaaccatca | ccgtgcggga | caccatgtct | gacctccctg | agatccggaa | cggggcctcg | 4140 |
| gcactggaga | tttcatacaa | ccgggagccc | cagtcctggt | tccagaggca | gctccggggc | 4200 |
| tcgcagtacc | agcccatcct | cagggatcat | atttgcaagg | acatgagcgc | cttggtggct | 4260 |
| gcccgcatgc | ggcacatccc | cctggccccg | ggctcggact | ggcgtgacct | gcccaacatt | 4320 |
| gaggtgcggc | tctctgacgg | caccctggcc | cggaagctgc | ggtacaacta | ccacgacaag | 4380 |
| aagaacggct | gcagcagcag | cggcgccctc | cgtggggtct | gctcctgtgt | ggaaggcaag | 4440 |
| ccctgtgagc | ctgcggcccg | acagtttaac | acccttatcc | cctggtgcct | gccccacact | 4500 |
| gggaacaggc | acaaccactg | gccggcctc | tacgggcgtc | tcgagtggga | cggcttcttc | 4560 |
| agcacaactg | tcaccaaccc | cgagcccatg | ggcaagcagg | gccgcgtgct | ccaccccgag | 4620 |
| cagcaccgag | tggtgagcgt | ccgggagtgc | cccgctccc | agggcttccc | cgacacctat | 4680 |
| cggctgttcg | gcaacatcct | agacaagcac | cggcaggtgg | gtaatgctgt | gccgccgcca | 4740 |
| ctggccaaag | ccatcggctt | ggagatcaag | cgctgcatgt | tggccaaagc | gcgcgagagc | 4800 |
| gcctcagcta | aaatcaagga | ggaggctgcc | aaggactagt | tctctcctcc | tatcacccat | 4860 |
| gtttctgcca | ccagagatcc | ccaacgtgca | ctgatattgg | tgtattttc | acatgtcaat | 4920 |
| cagtcaattc | agatgtgtcg | tatgcggtgt | ttgtggcctt | ggctgacatg | aaactcttca | 4980 |
| gtgagatttg | cctatcggct | aatttggact | tantgatcaa | actgtgcagt | actttgtcca | 5040 |
| ttctggattt | taaaagttttt | tttttacgca | ttatatnaaa | tttaccactg | tttgagtggn | 5100 |
| aattaagact | ttatgtagnt | tttatatgtt | gnaatatttc | ttcaaaaaat | ctcttcttaa | 5160 |
| aaacaaaaaa | aaaaaaaaaa | aaaaaaaaaa | aa | | | 5192 |

<210> SEQ ID NO 23
<211> LENGTH: 1241
<212> TYPE: PRT
<213> ORGANISM: Micromonas sp.

<400> SEQUENCE: 23

```
Met Trp His Lys Asp Thr Arg Ala Pro Leu Thr Ile Glu Arg Cys Leu
1               5                   10                  15

Ser Ser Met Pro Ser Asp Thr Ala Asp Leu Ala Arg Glu Ser His Ala
            20                  25                  30

Trp Leu Gln Lys His Gly Ala Ile Asn Tyr Gly Ala Ile Asp Val Pro
        35                  40                  45

Pro Pro Lys Pro Pro Thr Pro Glu Pro Glu Pro Ala Pro Glu Asn Ala
50                  55                  60

Glu Pro Glu Asp Ala Ser Pro Pro Thr Thr Ile Thr Asp Glu Leu Leu
65                      70                  75                  80

Thr Glu Arg Thr Val Ala Tyr Leu Arg Thr Ala Asp Met Asn Thr Thr
                85                  90                  95

Thr Glu Lys Gln Ile Arg Lys Ala Ile Glu Ala Glu Leu Gly Ala Asp
                100                 105                 110

Leu Thr Glu Lys Lys Leu Val Val Arg Ala Ile Val Thr Gly Phe Leu
            115                 120                 125

Glu Asp Pro Asp Lys Tyr Arg Asp Val Gly Lys Gly Lys Gly Ala Glu
130                 135                 140

Glu Arg Arg Glu Asp Ala Ala Lys Ala Lys Ala Val Ala Lys Ala
145                 150                 155                 160

Lys Ala Glu Ile Glu Ala Ala Lys Pro Lys Pro Thr Lys Pro Val Ile
                165                 170                 175

Ile Val Gly Ala Gly Pro Ala Gly Leu Ala Ala Ala Arg Met Leu Thr
                180                 185                 190

Ser His Gly His Ala Cys Val Val Leu Glu Ala Arg Asp Arg Val Gly
            195                 200                 205

Gly Arg Val His Thr Asp Ser Ser Ser Leu Ser Val Pro Val Asp Met
210                 215                 220

Gly Ala Ser Ile Ile Thr Gly Cys Ala Ala Asp Ala Lys Arg Arg Thr
225                 230                 235                 240

Gly Leu Pro Trp Leu Gly Val Arg Ala Asp Pro Ser Ala Thr Ile Ala
                245                 250                 255

Ala Gln Leu Gly Leu Gly Leu Lys Thr Leu Gly Asn Lys Leu Pro Leu
            260                 265                 270

Tyr Asp Gly Val Thr Gly Glu Leu Val Ser Asp Glu Leu Asp Ala Arg
            275                 280                 285

Val Glu Arg His Arg Asp Ala Leu Met Asp Arg Ala Arg Leu Arg Val
            290                 295                 300

Asp Arg Glu Gly Asp Ala Thr Ala Lys Met Ser Leu Ala Glu Val
305                 310                 315                 320

Ile Glu Asp Glu Leu Glu Gln Ala Phe Gly Glu Asn Val Ala Pro Ser
                325                 330                 335

Pro Ala Ala Ala Ala Ala Asp Gly Ala Gly Glu Gly Glu Asp
            340                 345                 350

Gly Glu Lys Arg Glu Lys Val Thr Leu Thr Ala Arg Glu Arg Arg Leu
            355                 360                 365

Leu Gly Trp His Trp Ala Asn Leu Glu Tyr Gly Cys Ser Ala Pro Leu
            370                 375                 380

Ser Lys Ile Ser Met Ala His Trp Asn Gln Asp Glu Pro Tyr Gly Gly
385                 390                 395                 400

Phe Gly Gly Pro His Cys Met Val Arg Gly Tyr Gly Gln Ile Thr
                405                 410                 415
```

```
Asp Ala Leu Ala Ala Gly Leu Glu Ile Arg Phe Lys Ile Val Val Lys
                420                 425                 430

Lys Val Glu His Phe Gly Gly Glu Gly Asp Ala Gly Val Val Val
            435                 440                 445

His Val Ala Asn Gly Glu Arg Phe Glu Gly Ser Ala Cys Ile Val Thr
        450                 455                 460

Ala Pro Leu Gly Cys Leu Lys Ser Gly Asp Ile Glu Phe Val Pro Arg
465                 470                 475                 480

Leu Ser Glu Ala Lys Ser Val Ala Ile Gln Arg Leu Gly Phe Gly Arg
                485                 490                 495

Leu Asn Lys Val Val Met Glu Phe Glu Lys Ser Phe Trp Asp Asp Gly
                500                 505                 510

Val Asp Tyr Phe Gly Ala Ala Arg Glu His Tyr Ala Pro Asp Ala Gln
            515                 520                 525

Ala Thr Gly Asp Asp Pro Ile Gly Gly Arg Gly Arg Met Phe Met Phe
530                 535                 540

Trp Asn Leu Lys Glu Ala Cys Gly Gly Ala Ser Val Leu Val Ala Leu
545                 550                 555                 560

Val Ala Gly Ser Ala Ala Glu Ala Met Glu Ser Gly Asp Glu Ser Glu
                565                 570                 575

Ser Ser Leu Val Ala Ser Ala Met Gly Val Leu Arg Arg Ile Phe Ser
            580                 585                 590

Asp Arg Ala Ser Asp Val Thr Thr Pro Lys Lys Val Ala Val Ser Arg
            595                 600                 605

Trp Gly Ser Asp Pro Tyr Ala Lys Gly Ser Tyr Ser Tyr Val Ala Val
610                 615                 620

Gly Ala Ser Ala Asp Asp Tyr Asp Glu Leu Gly Arg Pro Glu Glu Ser
625                 630                 635                 640

Ser Gly Gly Arg Leu Leu Phe Ala Gly Glu His Thr Cys Lys Glu His
                645                 650                 655

Pro Asp Thr Val Gly Gly Ala Met Leu Thr Gly Trp Arg Ala Ala Arg
            660                 665                 670

His Ala Leu His Val Met Asn Gly Ala Ser Gly Leu Pro Phe Asp Glu
            675                 680                 685

Val Phe Lys Leu Val Ser Leu Glu Asp Ile Ala Gly Ser Asp Asp Ser
690                 695                 700

Glu Asp Ser Asp Val Ser Gly Ser Ser Asp Asp Ser Asp Asp Glu Asp
705                 710                 715                 720

Asp Ala Asp Arg Gly Lys Lys Arg Lys Lys Glu Thr Lys Lys Glu Thr
                725                 730                 735

Lys Lys Arg Arg Gly Lys Lys Gly Arg Arg Val Asp Gly Glu Asp Gly
            740                 745                 750

Pro Glu Asp Asp Glu Lys Ala Arg Glu Arg Val Arg Arg Leu Glu
            755                 760                 765

Lys Glu Lys Gln Glu Arg Met Glu Gln Leu Ala Arg Glu Gln Lys Glu
            770                 775                 780

Met Thr Asp Gly Lys Glu Glu Val Lys Arg Val Leu Arg Leu Val Ser
785                 790                 795                 800

Ala Cys Pro Asp Gly Ala Ser Ala Pro Val Asp Ala Val Thr Phe Asp
                805                 810                 815

Gly Met Leu Glu Met Met Pro Ser Leu Glu Thr Ala Ser Gly Arg Gly
            820                 825                 830

Ala Phe Cys Gln Cys Ala Val Ala Lys Met Pro Arg Ala Gln Leu Ala
```

```
                835                 840                 845
Ser Leu Ala Leu Lys Asp Glu Gly Ala Cys Leu Ala Val Leu Ala Thr
    850                 855                 860
Trp Leu Glu Gln Val Pro Ser Lys Pro Ser Gly Lys Glu Leu Ser Ser
865                 870                 875                 880
Lys Met Leu Lys Leu Leu Ala Leu Asp Thr Asp Ala Val Asp Ala
                885                 890                 895
Arg Ala Leu Lys Glu Ser Gly Val Ala Arg Val Val Ala Asp Arg Phe
            900                 905                 910
Asn Ala His Ala Ile Pro Glu Ile Arg Leu Leu Ala Arg Arg Cys Ala
            915                 920                 925
His His Trp Ser Lys Ala Ala Ser Ala Ala Lys Ala Arg Arg Asp Ala
        930                 935                 940
Gln Ser Ser Lys Ala Gly Leu Ala Pro Glu Asp Thr Pro Leu Gly Asp
945                 950                 955                 960
Phe Ile Asp Asp Asp Ala Ser Met Asp Asp Ser Asp Ser Glu Arg
                965                 970                 975
Glu Tyr Asp Pro Asp Gly Lys Arg Arg Lys Arg Ala Glu Gln Lys
            980                 985                 990
Pro Pro Pro Lys Pro Met Thr Val  Glu Glu Ile Ile Glu  Ser Ala Ala
                995                1000                  1005
Gly Leu Gln Glu Gly Phe Ala  Ala Ala Glu Ala Gln  Arg Leu Lys
    1010                1015                  1020
Leu Glu  Ala Asp Ala Ala Leu  Ala Ala Ala His Ala  Ala Ala Ala
    1025                1030                  1035
Asp Ala  Lys Ala Glu Ala Ile  Arg Ala Glu Glu Val  Ala Lys Glu
    1040                1045                  1050
Arg Leu  Arg Gly Val Trp Asp  Ala Ala Pro Arg Val  Gly Lys Lys
    1055                1060                  1065
Gln Lys  Leu Arg Met Lys Thr  Phe Glu Asp Phe Ala  Lys His Lys
    1070                1075                  1080
Thr Ala  Lys Arg Glu His Lys  Lys Arg Gln Arg Leu  Glu Arg Glu
    1085                1090                  1095
Arg Glu  Asp Ala Glu Asp Ala  Arg Met Glu Ala Glu  Glu Ala Ala
    1100                1105                  1110
Ala Ala  Glu Arg Gly Ala Gly  Gly Ser Pro Gly Gly  Gly Asp Thr
    1115                1120                  1125
Ala Gly  Gly Gly Gly Val Asp  Leu Ala Ala Ala Ala  Ala Glu Ala
    1130                1135                  1140
Ala Arg  Val Ala Ser Leu Gly  Pro Glu Glu Arg Tyr  Arg Glu Asn
    1145                1150                  1155
Val Lys  Lys Ala Val Arg Phe  Tyr Val Arg Lys Gln  Leu Lys Gln
    1160                1165                  1170
Gly Ile  Lys Glu Lys Lys Leu  Arg Gly Leu Asn Lys  Glu Leu Cys
    1175                1180                  1185
Gly Lys  Ile Glu Glu Lys Ile  Ala Ala Lys Val Val  Glu Gly Ser
    1190                1195                  1200
Thr Ser  Leu Gly Ala Pro Gly  Asp Ser Val Glu Ala  Phe Leu Ser
    1205                1210                  1215
Lys Gln  Arg Arg Glu Lys Val  Lys Lys Met Val Glu  Ser Tyr Ala
    1220                1225                  1230
Ala Ser  Tyr Ala Lys Ala Lys  Lys
    1235                1240
```

<210> SEQ ID NO 24
<211> LENGTH: 278
<212> TYPE: PRT
<213> ORGANISM: Drosophila melanogaster

<400> SEQUENCE: 24

Met Ser Ala Glu Lys Ser Asp Lys Ala Lys Ile Ser Ala Gln Ile Lys
1               5                   10                  15

His Val Pro Lys Asp Ala Gln Val Ile Met Ser Ile Leu Lys Glu Leu
            20                  25                  30

Asn Val Gln Glu Tyr Glu Pro Arg Val Val Asn Gln Leu Leu Glu Phe
        35                  40                  45

Thr Phe Arg Tyr Val Thr Cys Ile Leu Asp Asp Ala Lys Val Tyr Ala
    50                  55                  60

Asn His Ala Arg Lys Lys Thr Ile Asp Leu Asp Asp Val Arg Leu Ala
65                  70                  75                  80

Thr Glu Val Thr Leu Asp Lys Ser Phe Thr Gly Pro Leu Glu Arg His
                85                  90                  95

Val Leu Ala Lys Val Ala Asp Val Arg Asn Ser Met Pro Leu Pro Pro
            100                 105                 110

Ile Lys Pro His Cys Gly Leu Arg Leu Pro Pro Asp Arg Tyr Cys Leu
        115                 120                 125

Thr Gly Val Asn Tyr Lys Leu Arg Ala Thr Asn Gln Pro Lys Lys Met
    130                 135                 140

Thr Lys Ser Ala Val Glu Gly Arg Pro Leu Lys Thr Val Val Lys Pro
145                 150                 155                 160

Val Ser Ser Ala Asn Gly Pro Lys Arg Pro His Ser Val Val Ala Lys
                165                 170                 175

Gln Gln Val Val Thr Ile Pro Lys Pro Val Ile Lys Phe Thr Thr Thr
            180                 185                 190

Thr Thr Thr Lys Thr Val Gly Ser Ser Gly Ser Gly Gly Gly
        195                 200                 205

Gly Gln Glu Val Lys Ser Glu Ser Thr Gly Ala Gly Gly Asp Leu Lys
    210                 215                 220

Met Glu Val Asp Ser Asp Ala Ala Val Gly Ser Ile Ala Gly Ala
225                 230                 235                 240

Ser Gly Ser Gly Ala Gly Ser Ala Ser Gly Gly Gly Gly Gly Gly
                245                 250                 255

Ser Ser Gly Val Gly Val Ala Val Lys Arg Glu Arg Glu Glu Glu
            260                 265                 270

Phe Glu Phe Val Thr Asn
        275

<210> SEQ ID NO 25
<211> LENGTH: 1107
<212> TYPE: DNA
<213> ORGANISM: Drosophila melanogaster

<400> SEQUENCE: 25
ccgatatgta cgtgcacaat ttcaatggaa taaacaatct tcttgcagca aagccgacgt      60
aaacataata actatagaag tatgagcgca gagaagtccg ataaggccaa gatcagtgcc     120
caaatcaagc acgtgccgaa ggacgcgcag gtgatcatgt ccatcctgaa ggagctgaat     180
gtccaggagt acgagccgcg cgtggtcaac caactgctgg agttcacctt ccgctatgtc     240

```
acctgcattc tggacgacgc caaggtatac gccaaccatg cgcgcaagaa gaccatcgac    300
ttggacgacg tgcgtctggc caccgaggtt acgctggaca agagcttcac cgggccgttg    360
gagcgccacg ttctagccaa ggtggccgac gtgcgcaaca gcatgcccct gccacccatt    420
aagccgcact gcggtctccg actgccgccc gaccgctact gtctcaccgg cgtcaactac    480
aaactgcggg ccactaatca gcccaagaaa atgaccaagt cggcggtgga gggccgtcca    540
ctgaagaccg tcgttaagcc cgtctccagc gccaatggtc cgaagaggcc acactccgtg    600
gtggccaagc agcaggtggt gaccattccc aagcccgtca tcaagtttac caccactacg    660
acaacgaaaa cggtgggcag ctccggcgga tctgggggcg gcggtggtca ggaggttaag    720
agcgagagca ccggcgccgg cggagatctc aagatggagg tggacagcga tgcggcggcc    780
gtgggcagca tcgctggcgc atccggttcg ggagcaggaa gtgccagcgg aggaggagga    840
ggaggaggat catctggcgt tggagtggcc gtcaagcggg aacgtgagga ggaggagttt    900
gagtttgtga ccaactagcg aaacgacatc atttaccttt aattaatatt cttaaatcag    960
accaaagcac ttgcatttgg ttgagcgaac tgggggtcta aatttcaact cgaatgtgaa    1020
gtcccaaaaa ccttagtata gattcgcccg ttaatcatta tgaaatctac gttttataca    1080
caaatacaac taccagattt tcatatt                                        1107
```

<210> SEQ ID NO 26  
<211> LENGTH: 264  
<212> TYPE: PRT  
<213> ORGANISM: Homo sapiens

<400> SEQUENCE: 26

```
Met Glu Ser Gly Lys Thr Ala Ser Pro Lys Ser Met Pro Lys Asp Ala
1               5                   10                  15

Gln Met Met Ala Gln Ile Leu Lys Asp Met Gly Ile Thr Glu Tyr Glu
            20                  25                  30

Pro Arg Val Ile Asn Gln Met Leu Glu Phe Ala Phe Arg Tyr Val Thr
        35                  40                  45

Thr Ile Leu Asp Asp Ala Lys Ile Tyr Ser Ser His Ala Lys Lys Ala
    50                  55                  60

Thr Val Asp Ala Asp Val Arg Leu Ala Ile Gln Cys Arg Ala Asp
65                  70                  75                  80

Gln Ser Phe Thr Ser Pro Pro Arg Asp Phe Leu Leu Asp Ile Ala
            85                  90                  95

Arg Gln Arg Asn Gln Thr Pro Leu Pro Leu Ile Lys Pro Tyr Ser Gly
        100                 105                 110

Pro Arg Leu Pro Pro Asp Arg Tyr Cys Leu Thr Ala Pro Asn Tyr Arg
    115                 120                 125

Leu Lys Ser Leu Gln Lys Lys Ala Ser Thr Ser Ala Gly Arg Ile Thr
    130                 135                 140

Val Pro Arg Leu Ser Val Gly Ser Val Thr Ser Arg Pro Ser Thr Pro
145                 150                 155                 160

Thr Leu Gly Thr Pro Thr Pro Gln Thr Met Ser Val Ser Thr Lys Val
            165                 170                 175

Gly Thr Pro Met Ser Leu Thr Gly Gln Arg Phe Thr Val Gln Met Pro
        180                 185                 190

Thr Ser Gln Ser Pro Ala Val Lys Ala Ser Ile Pro Ala Thr Ser Ala
    195                 200                 205

Val Gln Asn Val Leu Ile Asn Pro Ser Leu Ile Gly Ser Lys Asn Ile
    210                 215                 220
```

```
Leu Ile Thr Thr Asn Met Met Ser Ser Gln Asn Thr Ala Asn Glu Ser
225                 230                 235                 240

Ser Asn Ala Leu Lys Arg Lys Arg Glu Asp Asp Asp Asp Asp Asp
                245                 250                 255

Asp Asp Asp Asp Tyr Asp Asn Leu
                260

<210> SEQ ID NO 27
<211> LENGTH: 551
<212> TYPE: PRT
<213> ORGANISM: Homo sapiens

<400> SEQUENCE: 27

Met Asp Glu Leu Phe Pro Leu Ile Phe Pro Ala Glu Pro Ala Gln Ala
1               5                   10                  15

Ser Gly Pro Tyr Val Glu Ile Ile Glu Gln Pro Lys Gln Arg Gly Met
            20                  25                  30

Arg Phe Arg Tyr Lys Cys Glu Gly Arg Ser Ala Gly Ser Ile Pro Gly
        35                  40                  45

Glu Arg Ser Thr Asp Thr Thr Lys Thr His Pro Thr Ile Lys Ile Asn
    50                  55                  60

Gly Tyr Thr Gly Pro Gly Thr Val Arg Ile Ser Leu Val Thr Lys Asp
65                  70                  75                  80

Pro Pro His Arg Pro His Pro His Glu Leu Val Gly Lys Asp Cys Arg
                85                  90                  95

Asp Gly Phe Tyr Glu Ala Glu Leu Cys Pro Asp Arg Cys Ile His Ser
            100                 105                 110

Phe Gln Asn Leu Gly Ile Gln Cys Val Lys Lys Arg Asp Leu Glu Gln
        115                 120                 125

Ala Ile Ser Gln Arg Ile Gln Thr Asn Asn Asn Pro Phe Gln Val Pro
    130                 135                 140

Ile Glu Glu Gln Arg Gly Asp Tyr Asp Leu Asn Ala Val Arg Leu Cys
145                 150                 155                 160

Phe Gln Val Thr Val Arg Asp Pro Ser Gly Arg Pro Leu Arg Leu Pro
                165                 170                 175

Pro Val Leu Ser His Pro Ile Phe Asp Asn Arg Ala Pro Asn Thr Ala
            180                 185                 190

Glu Leu Lys Ile Cys Arg Val Asn Arg Asn Ser Gly Ser Cys Leu Gly
        195                 200                 205

Gly Asp Glu Ile Phe Leu Leu Cys Asp Lys Val Gln Lys Glu Asp Ile
    210                 215                 220

Glu Val Tyr Phe Thr Gly Pro Gly Trp Glu Ala Arg Gly Ser Phe Ser
225                 230                 235                 240

Gln Ala Asp Val His Arg Gln Val Ala Ile Val Phe Arg Thr Pro Pro
                245                 250                 255

Tyr Ala Asp Pro Ser Leu Gln Ala Pro Val Arg Val Ser Met Gln Leu
            260                 265                 270

Arg Arg Pro Ser Asp Arg Glu Leu Ser Glu Pro Met Glu Phe Gln Tyr
        275                 280                 285

Leu Pro Asp Thr Asp Asp Arg His Arg Ile Glu Glu Lys Arg Lys Arg
    290                 295                 300

Thr Tyr Glu Thr Phe Lys Ser Ile Met Lys Lys Ser Pro Phe Ser Gly
305                 310                 315                 320

Pro Thr Asp Pro Arg Pro Pro Arg Arg Ile Ala Val Pro Ser Arg
```

```
              325                 330                 335
Ser Ser Ala Ser Val Lys Pro Ala Pro Gln Pro Tyr Pro Phe Thr
            340                 345                 350

Ser Ser Leu Ser Thr Ile Asn Tyr Asp Glu Phe Pro Thr Met Val Phe
            355                 360                 365

Pro Ser Gly Gln Ile Ser Gln Ala Ser Ala Leu Ala Pro Ala Pro Pro
        370                 375                 380

Gln Val Leu Pro Gln Ala Pro Ala Pro Ala Pro Ala Met Val
385                 390                 395                 400

Ser Ala Leu Ala Gln Ala Pro Ala Pro Val Pro Val Leu Ala Pro Gly
                405                 410                 415

Pro Pro Gln Ala Val Ala Pro Pro Ala Pro Lys Pro Thr Gln Ala Gly
            420                 425                 430

Glu Gly Thr Leu Ser Glu Ala Leu Leu Gln Leu Gln Phe Asp Asp Glu
            435                 440                 445

Asp Leu Gly Ala Leu Leu Gly Asn Ser Thr Asp Pro Ala Val Phe Thr
450                 455                 460

Asp Leu Ala Ser Val Asp Asn Ser Glu Phe Gln Gln Leu Leu Asn Gln
465                 470                 475                 480

Gly Ile Pro Val Ala Pro His Thr Thr Glu Pro Met Leu Met Glu Tyr
                485                 490                 495

Pro Glu Ala Ile Thr Arg Leu Val Thr Gly Ala Gln Arg Pro Pro Asp
            500                 505                 510

Pro Ala Pro Ala Pro Leu Gly Ala Pro Gly Leu Pro Asn Gly Leu Leu
            515                 520                 525

Ser Gly Asp Glu Asp Phe Ser Ser Ile Ala Asp Met Asp Phe Ser Ala
        530                 535                 540

Leu Leu Ser Gln Ile Ser Ser
545                 550

<210> SEQ ID NO 28
<211> LENGTH: 1767
<212> TYPE: DNA
<213> ORGANISM: Homo sapiens

<400> SEQUENCE: 28
gaattccggc gaatggctcg tctgtagtgc acgccgcggg cccagctgcg accccggccc      60
cgccccgggg accccggcca tggacgaact gttccccctc atcttcccgg cagagccagc     120
ccaggcctct ggcccctatg tggagatcat tgagcagccc aagcagcggg gcatgcgctt     180
ccgctacaag tgcgaggggc gctccgcggg cagcatccca ggcgagagga gcacagatac     240
caccaagacc caccccacca tcaagatcaa tggctacaca ggaccaggga cagtgcgcat     300
ctccctggtc accaaggacc ctcctcaccg gcctcacccc cacgagcttg taggaaagga     360
ctgccgggat ggcttctatg aggctgagct ctgcccggac cgctgcatcc acagtttcca     420
gaacctggga atccagtgtg tgaagaagcg ggacctggag caggctatca gtcagcgcat     480
ccagaccaac aacaaccccc tccaagttcc tatagaagag cagcgtgggg actacgacct     540
gaatgctgtg cggctctgct tccaggtgac agtgcgggac ccatcaggca ggcccctccg     600
cctgccgcct gtccttcctc atcccatctt tgacaatcgt gccccaacaa ctgccgagct     660
caagatctgc cgagtgaacc gaaactctgg cagctgcctc ggtggggatg agatcttcct     720
actgtgtgac aaggtgcaga aagaggacat tgaggtgtat ttcacgggac caggctggga     780
ggcccgaggc tccttttcgc aagctgatgt gcaccgacaa gtggccattg tgttccggac     840
```

```
ccctccctac gcagaccccca gcctgcaggc tcctgtgcgt gtctccatgc agctgcggcg    900
gccttccgac cgggagctca gtgagcccat ggaattccag tacctgccag atacagacga    960
tcgtcaccgg attgaggaga aacgtaaaag gacatatgag accttcaaga gcatcatgaa   1020
gaagagtcct ttcagcggac ccaccgaccc ccggcctcca cctcgacgca ttgctgtgcc   1080
ttcccgcagc tcagcttctg tccccaagcc agcaccccag ccctatccct ttacgtcatc   1140
cctgagcacc atcaactatg atgagtttcc caccatggtg tttccttctg ggcagatcag   1200
ccaggcctcg gccttggccc cggcccctcc ccaagtcctg ccccaggctc cagcccctgc   1260
ccctgctcca gccatggtat cagctctggc ccaggcccca gcccctgtcc cagtcctagc   1320
cccaggccct cctcaggctg tggccccacc tgccccccaag cccacccagg ctggggaagg   1380
aacgctgtca gaggccctgc tgcagctgca gtttgatgat gaagacctgg gggccttgct   1440
tggcaacagc acagacccag ctgtgttcac agacctggca tccgtcgaca actccgagtt   1500
tcagcagctg ctgaaccagg gcatacctgt ggccccccac acaactgagc ccatgctgat   1560 ggagtacccct gaggctataa ctcgcctagt gacaggggcc cagaggcccc ccgacccagc   1620
tcctgctcca ctgggggccc cggggctccc caatggcctc ctttcaggag atgaagactt   1680
ctcctccatt gcggacatgg acttctcagc cctgctgagt cagatcagct cctaagggg   1740 tgacgcctgc cctccccaga gcactgg                                       1767

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Tyr Lys Asp Asp Asp Asp Lys Gly
1               5

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Lys Pro Ile Pro Asn Pro Leu Leu Gly Leu Asp Ser Thr
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Glu Gln Lys Leu Ile Ser Glu Glu Asp Leu
1               5                   10

<210> SEQ ID NO 32
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 32

Gln Pro Glu Leu Ala Pro Glu Asp Pro Glu Asp
1               5                   10

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Tyr Pro Tyr Asp Val Pro Asp Tyr Ala
1               5

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Tyr Thr Asp Ile Glu Met Asn Arg Leu Gly Lys
1               5                   10

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 35

His His His His His His
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Any amino acid; this region may encompass 1-3
      residues

<400> SEQUENCE: 36

Cys Cys Xaa Xaa Xaa Cys Cys
1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 37

Cys Cys Pro Gly Cys Cys
1               5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Leu Val Pro Arg Gly Ser
1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asp Asp Asp Asp Lys
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Glu Asn Leu Tyr Phe Gln Gly
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Leu Glu Val Leu Phe Gln Gly Pro
1               5

<210> SEQ ID NO 42
<211> LENGTH: 568
<212> TYPE: PRT
<213> ORGANISM: Xenopus laevis

<400> SEQUENCE: 42

Met Ala Phe Pro Leu Lys Asp Asp Leu Gly Arg Ala Lys Asp Cys Trp
1               5                   10                  15

Gly Cys Pro Ser Asp Thr Pro Ala Leu Ser Thr Cys Ser Asn Ala Asp
                20                  25                  30

Ile Phe Arg Arg Ile Asn Ala Met Leu Asp Asn Ser Leu Asp Phe Thr
            35                  40                  45

```
Gly Val Cys Thr Thr Pro Asn Thr Lys Gly Lys Cys Glu His Leu Gln
     50                  55                  60

Asp Tyr Gln Asp Thr Glu Gly Pro Ala Ala Ser Arg Met Leu Phe Ser
 65              70                  75                      80

Thr Ser His Glu Pro Leu Pro Arg Gly Leu Pro Asp Thr Asn Asp Leu
                 85                  90                  95

Cys Leu Gly Leu Gln Ser Leu Ser Leu Thr Gly Trp Asp Arg Pro Trp
                100                 105                 110

Ser Thr Gln Asp Ser Glu Ala Gly Gly His Ser Ser Thr Pro Thr Ala
            115                 120                 125

Ala Gln Ser Val Phe Ser Met Leu Asn Ser Pro Met Gly Lys Pro Ser
    130                 135                 140

Pro Leu Gly Phe Leu Thr Phe Asp Pro Ile Gly Ser Asp Leu Met Glu
145                 150                 155                 160

Lys Tyr Pro Thr Pro Leu Leu Arg Ser Ser Arg Leu Asp Ser Arg Ser
                165                 170                 175

Ile Leu Asp Ser Arg Ser Ser Pro Ser Asp Ser Thr Ser Gly
            180                 185                 190

Phe Ser Ser Gly Ser Asp His Leu Ser Asp Leu Ile Ser Ser Leu Arg
        195                 200                 205

Ile Ser Pro Pro Leu His Phe Leu Pro Leu Gly Gly Val Ser Arg
210                 215                 220

Asp Pro Leu Lys Leu Gly Ile Gly Ser Arg Leu Asp Gln Asp His Ala
225                 230                 235                 240

Ala Leu Ala Ala Ala Thr Val Ser Pro Leu Gly Ile Thr Lys Gly Trp
                245                 250                 255

Pro Ser Thr Ser Val Trp Pro Ser Trp Asp Leu Leu Asp Ser Ala Glu
            260                 265                 270

Asp Pro Phe Ser Ile Glu Arg Glu Ala Arg Leu His Arg Gln Ala Ala
        275                 280                 285

Ala Val Asn Glu Ala Thr Cys Thr Trp Ser Gly Gln Leu Pro Pro Arg
    290                 295                 300

Asn Tyr Lys Asn Pro Val Tyr Ser Cys Lys Val Phe Leu Gly Gly Val
305                 310                 315                 320

Pro Trp Asp Ile Thr Glu Thr Gly Leu Ile Asn Thr Phe Arg Val Phe
                325                 330                 335

Gly Ala Leu Ser Val Glu Trp Pro Gly Lys Asp Gly Lys His Pro Arg
            340                 345                 350

Cys Pro Pro Lys Gly Asn Met Pro Lys Gly Tyr Val Tyr Leu Val Phe
        355                 360                 365

Glu Ser Glu Lys Ser Val Arg Ala Leu Leu Gln Ala Cys Ser Gln Asp
    370                 375                 380

Leu Leu Ser Gln Asp Gly Leu Ser Glu His Tyr Phe Lys Met Ser Ser
385                 390                 395                 400

Arg Arg Met Ala Cys Lys Glu Val Gln Val Ile Pro Trp Val Leu Ala
                405                 410                 415

Asp Ser Asn Phe Val Arg Ser Pro Ser Gln Arg Leu Asp Pro Ser Lys
            420                 425                 430

Thr Val Phe Val Gly Ala Leu His Gly Met Leu Asn Ala Glu Ala Leu
        435                 440                 445

Ala Ser Ile Met Asn Asp Leu Phe Gly Val Val Tyr Ala Gly Ile
    450                 455                 460

Asp Thr Asp Lys His Lys Tyr Pro Ile Gly Ser Gly Arg Val Thr Phe
```

```
                465                 470                 475                 480

Asn Asn Gln Arg Ser Tyr Leu Lys Ala Val Ser Ala Ala Phe Val Glu
                    485                 490                 495

Ile Lys Thr Ala Lys Phe Thr Lys Lys Val Gln Ile Asp Pro Tyr Leu
                500                 505                 510

Glu Asp Ser Val Cys Gln Val Cys Asn Ala Gln Pro Gly Pro Phe Phe
            515                 520                 525

Cys Arg Asp Gln Val Cys Phe Lys Tyr Phe Cys Arg Ser Cys Trp His
        530                 535                 540

Trp Gln His Ser Met Glu Ile Leu Arg His His Arg Pro Leu Met Arg
545                 550                 555                 560

Asn Gln Lys Ser Arg Asp Ser Ser
                565

<210> SEQ ID NO 43
<211> LENGTH: 3137
<212> TYPE: DNA
<213> ORGANISM: Xenopus laevis

<400> SEQUENCE: 43
attccgattg cattgaaatt caatttggca ttaagtttta attacccag  tctgaccagg      60 agcctgcgcc atggccttcc cactgaaaga tgatttaggg agagccaaag attgctgggg     120
ctgcccatcc gacaccccag cccttttctac ctgcagcaat gctgatattt tcagacgaat    180
aaacgccatg ctggacaact ctctggattt cactggtgtt tgcaccaccc caaacacaaa     240
gggcaaatgt gaacaccttc aagactacca agatacagag gacctgcag  ctagcagaat    300 gctgttttcc acttcacatg aacctcttcc tcgcggcctt ccagatacca atgacttgtg     360
ccttggtctt cagtctctca gtcttacagg gtgggacaga ccctggagca ctcaggactc     420
agaagctggt ggacattcaa gtactccaac agctgctcag tctgtctta  gcatgctgaa    480 cagccccatg gggaagccaa gcccttggg  ctttctgaca tttgatccaa ttggttcaga    540
cctcatggag aagtatccta ctcctttgct gcgtagctct cgattggaca gccgctctat     600
tttggattct cgctccagca gcccttctga ctctgacact agtggattca gctctggatc     660
agaccacctt tcagacctaa tttcaagtct tcgcatctct cctccgctgc atttcctccc     720
acttggaggg ggagtgtcac gggacccgtt gaagctaggt attggctcaa ggctagacca     780
ggaccatgca gccttggcgg cagcaactgt ctctccactt ggcataacaa agggatggcc     840
cagtacttca gtctggcctt cctgggatct gctggattct gcagaggacc catttagcat     900
tgagcgagag gcacgcctac acagacaggc tgcagctgtg aatgaagcaa cctgcacctg     960
gagtgggcag ctgcccccta gaaactacaa aaatcctgtg tattcctgca agtctttct   1020 cggtggtgtc ccctgggaca taacagaaac tggacttatc aacacgttcc gtgtatttgg    1080
agcacttagt gttgagtggc ctggtaagga tggcaagcat ccccgctgcc ctcccaaagg    1140
taatatgccc aaaggttatg tttatctggt atttgaatca gagaagtcag ttcgtgcttt    1200
gcttcaggcg tgctctcagg acctactaag ccaagatggg ctgagtgaac actacttcaa    1260
aatgtccagt cgcaggatgg cctgcaagga ggtgcaggtc attccttggg tgcttgcaga    1320
cagcaacttt gtgcgtagtc catcacaacg gctggatccc agtaagactg tatttgtggg    1380
agctctacat ggcatgctaa atgctgaagc tttggcttcg atcatgaatg atctgtttgg    1440
tggcgtagtc tatgctggca ttgatactga taagcacaaa tatccaatcg ggtccggtcg    1500
tgtgaccttc aataaccagc gcagttacct gaaagctgtg agtgctgctt ttgtggaaat    1560
```

```
aaaaactgcc aagtttacaa aaaaggttca aattgatccg tatttggaag actctgtttg    1620
ccaggtgtgc aatgctcagc ctgggccatt cttctgcaga gaccaggttt gctttaagta    1680
tttctgccgt tcctgttggc actggcagca ctctatggaa atcctgcgcc accaccgccc    1740
tctcatgcgt aatcagaaaa gtcgtgactc cagctaaaga cattgaaaca acattggtcc    1800
aaaaatctga cacaactgga tatgttgggc taacaagagt gttcagaatt ttctccctct    1860
agcactggaa gcactagttt ttttttttt tattccaggg atagatcagc aatcagtgga    1920
ttgtggggag aatgtcacta ttttttgca cttgctgtac cttgtggtag ttttctcaca    1980
ctagtgcaca cttgagattt gccaggtttt ttgcttttct tttaaaaaaa aaaaattgag    2040
aggatatttc cttctcagga cttaattgca gttcccagac tgggcctaaa caacaattgc    2100
tgaaagtaag caatgttcat ggccttgttt tcttaaggtt tatggctaat gatgcctctg    2160
cttttggtta actttttttt tttttttatt acaggcactt cttttacatt ccttgcaata    2220
ttgctggtga tgatgcaaat tacattaatc ttcccatgtt ttgctgttgc catacagtgc    2280
cttccaattt atttgatgtc ccatctgaac tacataaact agtttagctg acattttttac   2340 tgtaacaaca atagcagaat ttgctcttta aaccaaatca tatttcatat ttttacccct    2400
gtggattttt accagttcct ttttacactc ttaaagacgt tttttaagtc cattatattt    2460
tgttttcttt tcctggcagc ttttaacatt attgcaaagt tcagtttctg ggagctgctg    2520
gttaagaaaa taaacctaca taaattcctt gtacaacaga gtttataacc aaaaggacag    2580
acttaaggcc ttgactgaac cagattatga cagtgtgtgt gtatagtttt aaggaaattt    2640
gttgcacttt tttaatttgc acttaagggg atggtagagt ttttaatcac tttctgtttg    2700
tatttggctg acaaaaaag ggctgtgata tgtcttgaga atggggtaga ggcaagagat    2760
ggcacaacac ctttctcctg gagggaataa gtgcccatgc tctgtttttc ttctttttt    2820 ttgtggaaat aactgactta tgcaaactgt tgcaggcctt tacaattttg tgtccttaat    2880
ttttatttat agcccccctt aaaattgtaa gctctgtgcc aaagaccca gttttctgta    2940 ttccctctta tccagaacat gctgagctaa ttctacttcc tagctgccct aagcagggta    3000
tatctgtgaa gctgtgtgta aagtctctac ctcattgtag ttatgcaagc agaagatgca    3060
cttaatctat ggatgtggtg tagttttgtt tgttttcctt tgtttttttt ggcacaaaat    3120
aaacacgttg aagcaga                                                   3137
```

<210> SEQ ID NO 44
<211> LENGTH: 525
<212> TYPE: PRT
<213> ORGANISM: Zea mays

<400> SEQUENCE: 44

```
Met Gly Pro Pro Ala Met Ala Phe Gln Ala Leu Thr Leu Thr Pro Leu
1               5                   10                  15

Pro Phe Ser Leu His Ser Ser Ser Arg Arg Val Arg Val Leu Ala Val
            20                  25                  30

Ala Ala Asp Gln Thr Pro Pro Ala Pro Pro Ser Glu Pro Ala Asn
        35                  40                  45

Ser Pro Ser Arg Leu Leu Arg Glu Leu Ala Gln Arg Lys Lys Ala Val
    50                  55                  60

Ser Pro Lys Lys Lys His Pro Pro Arg Arg Phe Ile Leu Lys Pro Pro
65                  70                  75                  80

Leu Asp Asp Glu Arg Leu Thr Arg Arg Phe Leu Ser Ser Pro Gln Leu
```

```
            85                  90                  95
Ser Leu Lys Ala Leu Pro Leu Leu Ser Ser Cys Leu Pro Ser Ala Pro
            100                 105                 110

Leu Ser Thr Ala Asp Arg Thr Trp Met Asp Glu Tyr Leu Leu Glu Ala
            115                 120                 125

Lys Gln Ala Leu Gly Tyr Pro Leu Ala Pro Ser Glu Thr Leu Gly Glu
            130                 135                 140

Gly Asp Asp Cys Pro Ala Arg His Phe Asp Val Leu Phe Tyr Leu Ala
145                 150                 155                 160

Phe Gln His Leu Asp Pro Ser Ser Glu Arg Thr Arg Met Arg His Val
                165                 170                 175

Arg Asn Gly His Ser Arg Leu Trp Phe Leu Gly Gln Tyr Val Leu Glu
                180                 185                 190

Leu Ala Phe Cys Glu Phe Phe Leu Gln Arg Tyr Pro Arg Glu Ser Pro
                195                 200                 205

Gly Pro Met Arg Glu Arg Val Phe Ala Leu Ile Gly Lys Lys Val Leu
                210                 215                 220

Pro Arg Trp Leu Lys Ala Ala Ser Leu His Asn Leu Val Phe Pro Tyr
225                 230                 235                 240

Asp Asp Leu Asp Lys Met Ile Arg Lys Asp Arg Glu Pro Pro Ser Lys
                245                 250                 255

Ala Val Phe Trp Ala Ile Phe Gly Ala Ile Tyr Leu Cys Phe Gly Met
                260                 265                 270

Pro Glu Val Tyr Arg Val Leu Phe Glu Ala Phe Gly Met Asp Pro Asp
                275                 280                 285

Asp Glu Ser Cys Gln Pro Lys Leu Arg Arg Gln Leu Glu Asp Val Asp
                290                 295                 300

Tyr Val Ser Val Glu Phe Glu Lys Arg Gln Leu Thr Trp Gln Asp Val
305                 310                 315                 320

Ala Ala Tyr Arg Pro Pro Asp Ala Leu Phe Ala His Pro Arg Leu
                325                 330                 335

Phe Arg Ala Cys Val Pro Pro Gly Met His Arg Phe Arg Gly Asn Ile
                340                 345                 350

Trp Asp Phe Asp Ser Arg Pro Lys Val Met Thr Thr Leu Gly Tyr Pro
                355                 360                 365

Leu Pro Met Asn Asp Arg Ile Pro Glu Ile Thr Glu Ala Arg Asn Ile
                370                 375                 380

Glu Leu Gly Leu Gly Leu Gln Leu Cys Phe Leu His Pro Ser Lys His
385                 390                 395                 400

Lys Phe Glu His Pro Arg Phe Cys Tyr Glu Arg Leu Glu Tyr Val Gly
                405                 410                 415

Gln Lys Ile Gln Asp Leu Val Met Ala Glu Arg Leu Leu Met Lys His
                420                 425                 430

Leu Asp Ala Pro Gly Arg Trp Leu Ala Glu Lys His Arg Arg Thr Leu
                435                 440                 445

Met Asn Lys Tyr Cys Gly Arg Tyr Leu Arg Asp Lys His Leu Gln His
                450                 455                 460

Tyr Ile Ile Tyr Gly Glu Thr Val Gln Asp Arg Phe Glu His Asn Arg
465                 470                 475                 480

Arg Leu Arg Asn Pro Ser Thr Thr Ser Val Gln Gln Ala Leu His Gly
                485                 490                 495

Leu Ala Tyr Cys Val Tyr Gly Lys Pro Asp Val Arg Arg Leu Met Phe
                500                 505                 510
```

Glu Val Phe Asp Phe Glu Gln Val Gln Pro Lys Ala Val
        515                 520                 525

<210> SEQ ID NO 45
<211> LENGTH: 2107
<212> TYPE: DNA
<213> ORGANISM: Zea mays

<400> SEQUENCE: 45

| | | | | | |
|---|---|---|---|---|---|
| cataattctc | gtctgcttat | ccgctccctt | ctctccctca | acttcagcaa | gttccccgca | 60 |
| aaaccgcagc | cggaggtcgc | cggtcgccac | caccaatggg | gccacccgcc | atggcgttcc | 120 |
| aagccctcac | cctcacgcca | ctcccttct | cactccacag | ctcgagccgc | cgcgtccgcg | 180 |
| tgcttgccgt | tgcggccgac | cagactcctc | cgcccgcccc | ccttcggag | ccggcgaaca | 240 |
| gccctagccg | cctccttcgc | gagctcgcgc | agcggaagaa | ggccgtatcc | cctaagaaga | 300 |
| agcatccgcc | gcgtcgcttc | atcctgaagc | cacctctcga | tgacgagcgc | cttaccggc | 360 |
| ggttcctcag | cagcccgcag | ctgtcgctca | aggcgctccc | gctgctctct | tcctgcctcc | 420 |
| cctccgcgcc | gctctccacc | gccgacagga | cctggatgga | cgagtacctc | ctcgaggcca | 480 |
| agcaggcgct | cgggtacccg | ctcgcgccct | cggagacgct | cggcgaaggc | gatgactgcc | 540 |
| ccgcgcgtca | tttcgatgtg | ctgttctacc | tcgcgttcca | gcatctggac | ccctctagcg | 600 |
| agcgcacgcg | gatgcggcac | gtacggaacg | gccactccag | gctctggttc | ctgggtcagt | 660 |
| acgttctgga | gctcgcgttc | tgcgagttct | tcttgcagag | gtaccccagg | gagtcacctg | 720 |
| ggccgatgag | ggagcgggtg | ttcgctctaa | ttgggaagaa | agtgttgccc | cgatggctca | 780 |
| aggcggccag | cctgcacaat | ttggtcttcc | cctatgatga | tttggataag | atgatacgaa | 840 |
| aggacccgga | gccaccgtcc | aaggctgtat | tctgggcaat | atttggagct | atatatttgt | 900 |
| gctttggaat | gcctgaagtc | tatcgtgtcc | ttttgaggc | atttgggatg | gatccagatg | 960 |
| atgagagctg | tcagccaaaa | ttgcgtcgtc | aactagagga | tgttgattat | gtttcagtgg | 1020 |
| agttcgaaaa | gaggcagctc | acttggcagg | atgttgctgc | ctacaggccg | ccaccggatg | 1080 |
| ctcttttgc | tcatcctagg | cttttccgag | cttgtgtgcc | accaggcatg | catcggttca | 1140 |
| gaggaaatat | ttgggatttt | gacagtagac | ccaaggtcat | gactacccta | ggatatccct | 1200 |
| tgcccatgaa | tgcagaatt | ccagaaatca | cagaagcaag | gaatatagag | cttgacttg | 1260 |
| gtcttcagct | gtgttttttg | cacccatcaa | acataagtt | tgagcatcca | agattttgtt | 1320 |
| atgagcggct | tgaatacgtc | ggccagaaaa | ttcaggatct | agtaatggca | gagaggctac | 1380 |
| tcatgaaaca | cctcgatgca | ccaggcaggt | ggctggcgga | gaagcatcgg | aggacgttga | 1440 |
| tgaacaagta | ttgtggacgg | tacctgcggg | acaagcacct | gcagcactac | attatctacg | 1500 |
| gggagacagt | gcaagacaga | ttcgaacaca | atcgacgtct | aaggaatcct | tcaacgacct | 1560 |
| ctgtccagca | agcgctacat | gggcttgcat | actgtgtgta | tggcaaacct | gacgtgcggc | 1620 |
| gtttgatgtt | cgaggtgttt | gacttcgaac | aggtccagcc | taaagcagtc | tgaggatctt | 1680 |
| ctccattggt | accgatgcta | gagttgctga | atgctgacca | caagacccc | aatggcagtg | 1740 |
| gtacaaatgc | tgtagattct | tgaagtcgtc | cattcgacag | gagatctttc | gattytgaag | 1800 |
| cctgaagccc | tgaaccctga | gctgggacag | ctgattagcc | actgggtcct | gtctctcctg | 1860 |
| aaaccgtcac | tgttccaacc | ttcttgtccg | tcggaaatgg | tagactagtg | atgatgtgga | 1920 |
| tcggaggctg | ctgttgtttg | aacttacaat | tttgataatt | cgttgtaaat | tcctgttgg | 1980 |
| gcagaaacgc | aaatagcagc | agcatggcag | attcatttcc | tatcagaatt | gtagtccgta | 2040 |

```
atcgagaagc agtaagatga ataatataaa gatattcatt caaaaaaaaa aaaaaaaaaa    2100
aaaaaaa                                                              2107
```